(12) United States Patent
Mochizuki et al.

(10) Patent No.: US 9,896,708 B2
(45) Date of Patent: Feb. 20, 2018

(54) HEPAROSAN-GLUCURONIC ACID-5-EPIMERASE, AND METHOD FOR PRODUCING POLYSACCHARIDE USING SAME

(71) Applicant: SEIKAGAKU CORPORATION, Tokyo (JP)

(72) Inventors: Hideo Mochizuki, Tokyo (JP); Kiwamu Yamagishi, Tokyo (JP); Kiyoshi Suzuki, Tokyo (JP); Yeong Shik Kim, Seoul (KR)

(73) Assignee: SEIKAGAKU CORPORATION, Tokyo (JP)

( * ) Notice: Subject to any disclaimer, the term of this patent is extended or adjusted under 35 U.S.C. 154(b) by 20 days.

(21) Appl. No.: 14/897,667

(22) PCT Filed: Jun. 12, 2014

(86) PCT No.: PCT/JP2014/065533
§ 371 (c)(1),
(2) Date: Dec. 11, 2015

(87) PCT Pub. No.: WO2014/200045
PCT Pub. Date: Dec. 18, 2014

(65) Prior Publication Data
US 2016/0115511 A1    Apr. 28, 2016

(30) Foreign Application Priority Data

Jun. 12, 2013  (JP) ................. 2013-123435

(51) Int. Cl.
| | |
|---|---|
| *C12P 19/24* | (2006.01) |
| *C12N 9/90* | (2006.01) |
| *C08B 37/00* | (2006.01) |
| *C12P 19/04* | (2006.01) |

(52) U.S. Cl.
CPC .......... *C12P 19/24* (2013.01); *C08B 37/0075* (2013.01); *C12N 9/90* (2013.01); *C12P 19/04* (2013.01); *C12Y 501/03* (2013.01)

(58) Field of Classification Search
CPC ............................................... C12Y 501/0317
See application file for complete search history.

(56) References Cited

U.S. PATENT DOCUMENTS

| | | | |
|---|---|---|---|
| 6,764,844 B1 | 7/2004 | Lindahl et al. | |
| 7,399,626 B2 | 7/2008 | Jalkanen et al. | |
| 2004/0191867 A1 | 9/2004 | Lindahl et al. | |
| 2005/0181434 A1 | 8/2005 | Jalkanen et al. | |
| 2009/0280502 A1 | 11/2009 | Suzuki et al. | |

FOREIGN PATENT DOCUMENTS

| | | |
|---|---|---|
| JP | 2007-297336 A | 11/2007 |
| WO | 98/48006 A1 | 10/1998 |
| WO | 02/46379 A2 | 6/2002 |
| WO | 2006/023487 A2 | 3/2006 |

OTHER PUBLICATIONS

Munoz et al. 2006; Enzymatic synthesis of heparin related polysaccharides on sensor chips: rapid screening of heparin-protein interactions. Biochemical and Biophysical Research Communications. 339: 597-602.*
Chavaroche et al. published 2013 and online May 14, 2012; Production methods for heparosan, a precursor of heparin and heparin sulfate. Carbohydrate polymers. 93: 38-47.*
Li et al. 2001; Characterization of the D-glycuronyl C5-epimerase involved in the biosynthesis of heparin and heparan sulfate. J. Biol. Chem. 276(23):20069-20077.*
Li. 2010; Glucuronyl C5-epimerase: An enzyme converting glucuronic acid to iduronic acid in heparaon sulfate/heparin biosynthesis. Progress in Molecular Biology and Translational Science 93: 59-78.*
Mochizuki et al. 2015; Heparosan-glucuronate 5-epimerase: Molecular cloning and characterization of a novel enzyme. Glycobiology. 25(7): 735-744.*
Chavaroche et al., "Production methods for heparosan, a precursor of heparin and heparan sulfate", Carbohydrate Polymers, 2013, vol. 93, pp. 38-47.
Mochizuki et al., "Heparosan-glucuronate 5-epimerase: Molecular cloning and characterization of a novel enzyme", Glycobiology, 2015, vol. 25, No. 7, pp. 735-744.
Communication dated Jan. 18, 2017 from the European Patent Office in corresponding Application No. 14811007.5.
International Preliminary Report on Patentability dated Dec. 23, 2015 from the International Bureau in counterpart International Application No. PCT/JP2014/065533.
Masayuki Ishihara et al., "Importance of 2-O-Sulfate Groups of Uronate Residues in Heparin for Activation of FGF-1 and FGF-2", J. Biochem., 1997, pp. 345-349, vol. 121, No. 2.
Database Uniprot[Online],Accession No. H2Q9P8 http://www.uniprot.org/uniprot/H2Q9P8 Mar. 21, 2012 uploaded, [retrieved on Sep. 5, 2014], Definition: Glucuronic acid epimerase.
Lianli Chi et al., "Preparation and structural determination of large oligosaccharides derived from acharan sulfate", Carbohydrate Research, 2006, pp. 864-869, vol. 341.
J.T. Gallagher et al., "Patterns of Sulphation in Heparan Sulphate: Polymorphism Based on a Common Structural Theme", Int. J. Biochem., 1992, pp. 553-560, vol. 24, No. 4.

(Continued)

*Primary Examiner* — Karen Cochrane Carlson
(74) *Attorney, Agent, or Firm* — Sughrue Mion, PLLC

(57) ABSTRACT

To provide a polypeptide having heparosan-glucuronate 5-epimerase activity, whereby means for producing a polysaccharide in which hexuronic acid residues has been epimerized is provided. Through screening of *Achatina fulica* cDNA library, a DNA encoding a polypeptide of heparosan-glucuronate 5-epimerase is obtained. The epimerase acts on glucuronic acid residues of N-acetyl heparosan and/or iduronic acid residues of completely desulfated N-acetylated heparin. The polypeptide encoded by the DNA is expressed by insect cells, to thereby yield the polypeptide having heparosan-glucuronate 5-epimerase activity. By bringing the polypeptide into contact with N-acetyl heparosan or completely desulfated N-acetylated heparin, a polysaccharide in which hexuronic acid residues has been epimerized is yielded.

8 Claims, 3 Drawing Sheets

(56) References Cited

OTHER PUBLICATIONS

Yeong S. Kim et al., "A New Glycosaminoglycan from the Giant African Snail *Achatina fulica*", The Journal of Biological Chemistry, May 17, 1996, pp. 11750-11755, vol. 271, No. 20.
Yeong Shik Kim et al., "Determination of the structure of oligosaccharides prepared from acharan sulfate", Glycobiology, 1998, pp. 869-877, vol. 8, No. 9.
Ulf Lindahl et al., "Regulated Diversity of Heparan Sulfate", The Journal of Biological Chemistry, Sep. 25, 1998, pp. 24979-24982, vol. 273, No. 39.
Jeffrey D. Esko et al., "Molecular diversity of heparan sulfate", J. Clin. Invest., 2001, pp. 169-173, vol. 108, No. 2.
Patrick Campbell et al., "Biosynthesis of Heparin/Heparan Sulfate", The Journal of Biological Chemistry, Oct. 28, 1994, pp. 26953-26958, vol. 269, No. 43.
Jin-Ping Li et al., "Biosynthesis of Heparin/Heparan Sulfate", The Journal of Biological Chemistry, Oct. 31, 1997, pp. 28158-28163, vol. 272, No. 44.
Asa Hagner-McWhirter et al., "Biosynthesis of heparin/heparan sulphate: mechanism of epimerization of glucuronyl C-5", Biochem J., 2000, pp. 69-75, vol. 347, Pt. 1.
Jin-Ping Li et al., "Characterization of the D-Glucuronyl C5-epimerase Involved in the Biosynthesis of Heparin and Heparan Sulfate", The Journal of Biological Chemistry, Jun. 8, 2001, pp. 20069-20077, vol. 276, No. 23.
Brett E. Crawford et al., "Cloning, Golgi Localization, and Enzyme Activity of the Full-length Heparin/Heparan Sulfate-Glucuronic Acid C5-epimerase", The Journal of Biological Chemistry, Jun. 15, 2001, pp. 21538-21543, vol. 276, No. 24.
Tarsis F. Gesteira et al., "A novel approach for the characterisation of proteoglycans and biosynthetic enzymes in a snail model", Biochimica et Biophysica Acta, 2011, pp. 1862-1869, vol. 1814, No. 12.
International Search Report for PCT/JP2014/065533 dated Sep. 16, 2014.
Masayuki Ishihara et al., "2-*O*-Sulfate Groups of Uronate Residues in Herapin for Activation of FGF-1 and FGF-2", J. Biochem., 1997, pp. 345-349, vol. 121, No. 2.
Communication dated Feb. 7, 2017 issued by the State Intellectual Property Office of People's Republic of China in corresponding application No. 201480033636.4.

\* cited by examiner

[Fig. 1]
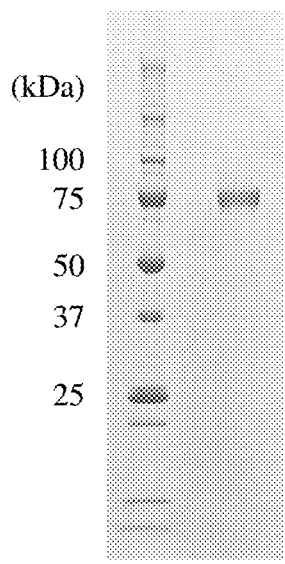
[Fig. 2]
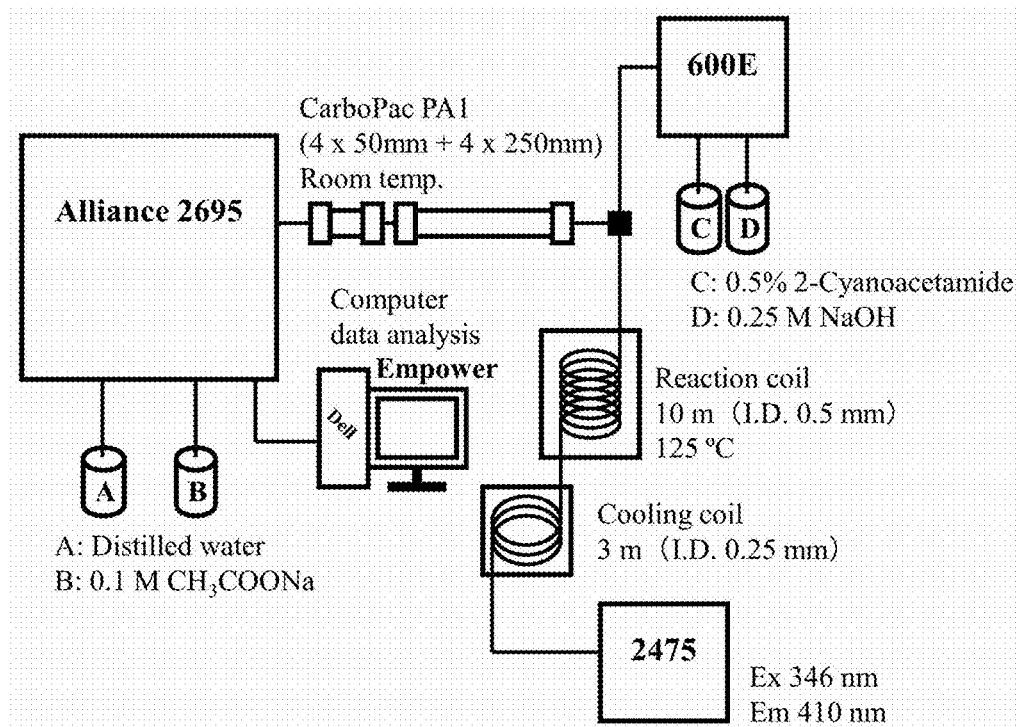

[Fig. 3]
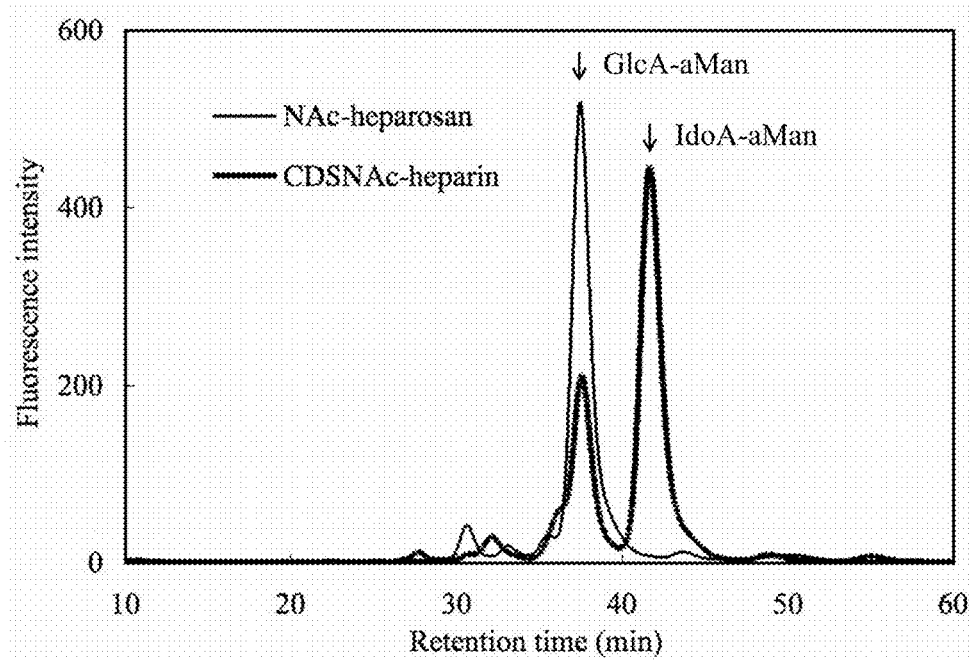
[Fig. 4]
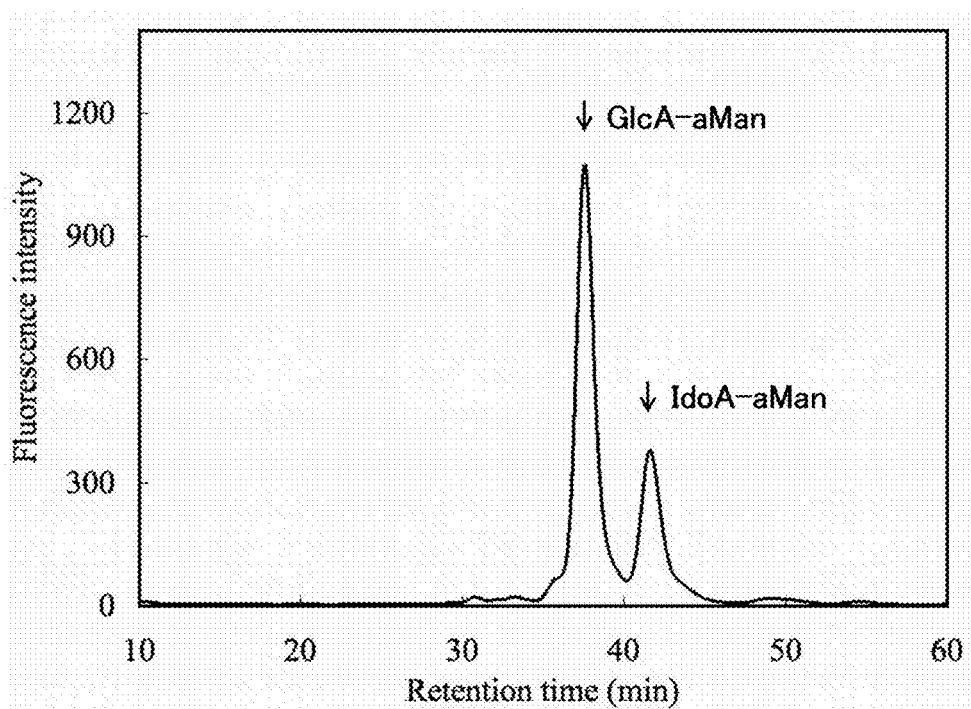

[Fig. 5]
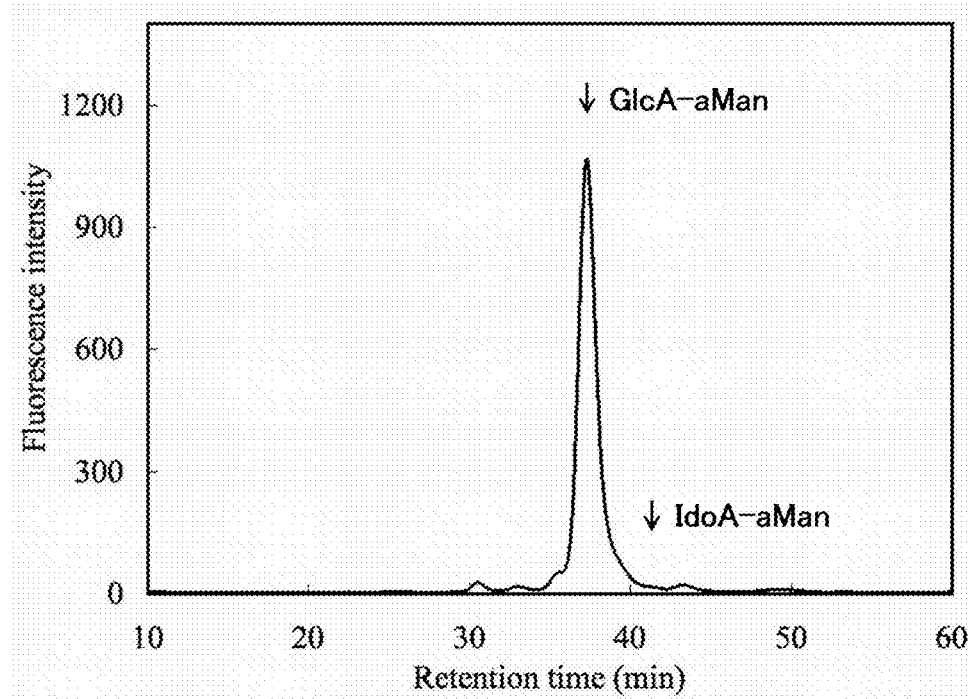
[Fig. 6]
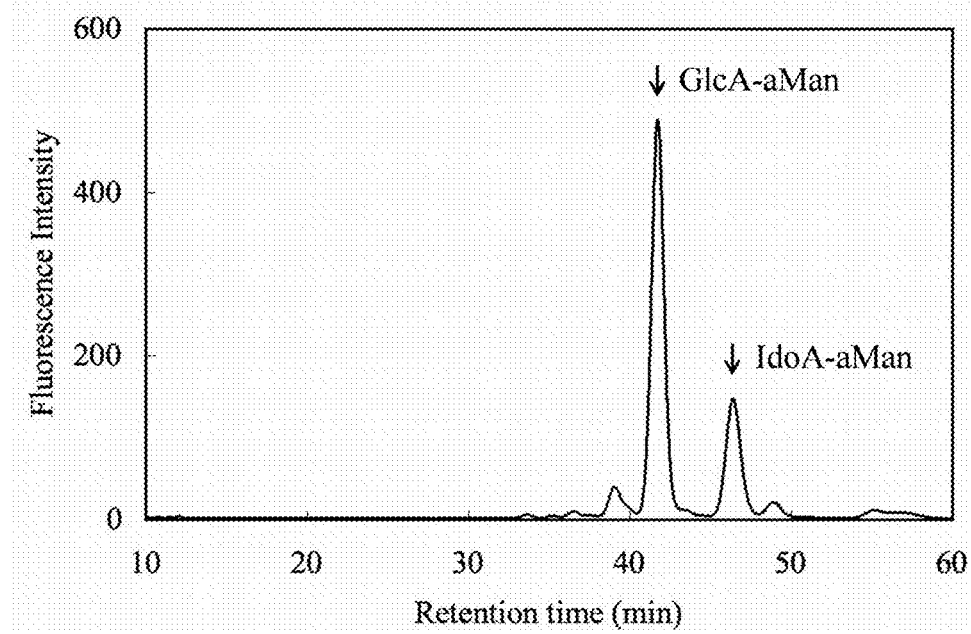

```
                           SEQUENCE LISTING

<160> NUMBER OF SEQ ID NOS: 42

<210> SEQ ID NO 1
   <211> LENGTH: 1806
   <212> TYPE: DNA
   <213> ORGANISM: Achatina fulica
   <220> FEATURE:
   <221> NAME/KEY: CDS
   <222> LOCATION: (1)..(1806)

<400> SEQUENCE: 1 atg cac ctt aca tgt gta aga aga gcc ttt cgt aaa gtt aac tgg ctg       48
   Met His Leu Thr Cys Val Arg Arg Ala Phe Arg Lys Val Asn Trp Leu
   1               5                   10                  15 ctt cgt tct gtt gtt cta ctt ttg acc gga gga tgt ttg aca ata ttg       96
   Leu Arg Ser Val Val Leu Leu Leu Thr Gly Gly Cys Leu Thr Ile Leu
                   20                  25                  30 gtg aac tgg caa tgg ccc aat agt aga cca tat tat tgg ctc aga tca      144
   Val Asn Trp Gln Trp Pro Asn Ser Arg Pro Tyr Tyr Trp Leu Arg Ser
               35                  40                  45 gat gca gag ttt gct gga cag ttt gta tca acg gcc gac agc tct cag      192
   Asp Ala Glu Phe Ala Gly Gln Phe Val Ser Thr Ala Asp Ser Ser Gln
           50                  55                  60 ttg ttc gaa gat caa aca gtc tct tgt ccg ccg tgt cca agt ata gac      240
   Leu Phe Glu Asp Gln Thr Val Ser Cys Pro Pro Cys Pro Ser Ile Asp
   65                  70                  75                  80 gac ttt cct cag tca gca caa act ttg gac ctg cag ata att aac tgt      288
   Asp Phe Pro Gln Ser Ala Gln Thr Leu Asp Leu Gln Ile Ile Asn Cys
                   85                  90                  95 tcg ata aat gaa gca gag aca att gaa tgt aga caa gac aaa gga gaa      336
   Ser Ile Asn Glu Ala Glu Thr Ile Glu Cys Arg Gln Asp Lys Gly Glu
                  100                 105                 110 gtc tac atg cca gtc tcc ttc atc aac aac tat ttt gag gtc ttt gga      384
   Val Tyr Met Pro Val Ser Phe Ile Asn Asn Tyr Phe Glu Val Phe Gly
              115                 120                 125 gat gtg aaa cgt gac ggc acc agt aaa ctg tac aat ttt cag cat gct      432
   Asp Val Lys Arg Asp Gly Thr Ser Lys Leu Tyr Asn Phe Gln His Ala
          130                 135                 140 tac ggc aag atc cat ccg ccc cag cct gtc tat cac cca gga ggg gta      480
   Tyr Gly Lys Ile His Pro Pro Gln Pro Val Tyr His Pro Gly Gly Val
   145                 150                 155                 160 ttc cta aat ttt gag aag tac aat gta gcg gct aga gaa aag att ctt      528
   Phe Leu Asn Phe Glu Lys Tyr Asn Val Ala Ala Arg Glu Lys Ile Leu
                   165                 170                 175 tgt gtg aca gct tct gat ggc gtg cca tta gcc aaa cag tgg gat ccc      576
   Cys Val Thr Ala Ser Asp Gly Val Pro Leu Ala Lys Gln Trp Asp Pro
                  180                 185                 190 gct ggg tac tac tac gcc att tca gtt gca cag tat ggt ctg agt cat      624
   Ala Gly Tyr Tyr Tyr Ala Ile Ser Val Ala Gln Tyr Gly Leu Ser His
              195                 200                 205 cat gcc aag ggt att cta gaa gga aac cca acg ccc agg ctg atg gct      672
   His Ala Lys Gly Ile Leu Glu Gly Asn Pro Thr Pro Arg Leu Met Ala
          210                 215                 220 ggt ggc cag gtg gaa gag tca agg tgg gaa aat aca ggc cct gag atg      720
   Gly Gly Gln Val Glu Glu Ser Arg Trp Glu Asn Thr Gly Pro Glu Met
   225                 230                 235                 240
```

```
gaa gtt aat atc gca gag aca act gta gat gga gaa atg atg agg gta    768
Glu Val Asn Ile Ala Glu Thr Thr Val Asp Gly Glu Met Met Arg Val
            245                 250                 255 ctg tcg ttc agt gct cca gaa tca tat act gcc cct ggt cct gtt ctt    816
Leu Ser Phe Ser Ala Pro Glu Ser Tyr Thr Ala Pro Gly Pro Val Leu
        260                 265                 270 cgt ttg agc acg caa gag cag aca atc tgt ttt gac tta caa ctg act    864
Arg Leu Ser Thr Gln Glu Gln Thr Ile Cys Phe Asp Leu Gln Leu Thr
    275                 280                 285 gga cct ggt ggg gtc act gta caa ata aag acc agg aac ggc aga aca    912
Gly Pro Gly Gly Val Thr Val Gln Ile Lys Thr Arg Asn Gly Arg Thr
290                 295                 300 ggc tac ata cat ttt atc ctt gat gac aga tac atg gag gtt aac gga    960
Gly Tyr Ile His Phe Ile Leu Asp Asp Arg Tyr Met Glu Val Asn Gly
305                 310                 315                 320 agc cac gtt tta tat gga ata ggc acg aag aat ctt gga aaa tgg gta   1008
Ser His Val Leu Tyr Gly Ile Gly Thr Lys Asn Leu Gly Lys Trp Val
            325                 330                 335 cat cta aca aga gat atc ttt gtg gac tgg atg aaa acc ctg cat aac   1056
His Leu Thr Arg Asp Ile Phe Val Asp Trp Met Lys Thr Leu His Asn
        340                 345                 350 gca caa ttc agc tca ccg acg caa ttc aaa gag ata gtg gat gtg aca   1104
Ala Gln Phe Ser Ser Pro Thr Gln Phe Lys Glu Ile Val Asp Val Thr
    355                 360                 365 ctg cat gga act ggg tat ctt gat aac tta aca tta tct aca tct gcg   1152
Leu His Gly Thr Gly Tyr Leu Asp Asn Leu Thr Leu Ser Thr Ser Ala
370                 375                 380 cac aac gac cat ctt atc cat gct gcg aac tgg cta gtt aat aat caa   1200
His Asn Asp His Leu Ile His Ala Ala Asn Trp Leu Val Asn Asn Gln
385                 390                 395                 400 gac agt gct gga ggc tgg cca act agc att gga atg aaa acc ggt gaa   1248
Asp Ser Ala Gly Gly Trp Pro Thr Ser Ile Gly Met Lys Thr Gly Glu
            405                 410                 415 aac atc gaa ctg aaa cct ggc tgg tac tcc gct atg ggt caa ggc caa   1296
Asn Ile Glu Leu Lys Pro Gly Trp Tyr Ser Ala Met Gly Gln Gly Gln
        420                 425                 430 gca atg tct aca ctt gtc cga gca tat aac ctg act gcg cat aaa tat   1344
Ala Met Ser Thr Leu Val Arg Ala Tyr Asn Leu Thr Ala His Lys Tyr
    435                 440                 445 tac ctg gat acc gcc gta cga gct tta cat tta tat gag ttg gga tct   1392
Tyr Leu Asp Thr Ala Val Arg Ala Leu His Leu Tyr Glu Leu Gly Ser
450                 455                 460 gat gtt ggt ggt gtt cga gct cgt ttc ctg gga caa ctt gat tgg tat   1440
Asp Val Gly Gly Val Arg Ala Arg Phe Leu Gly Gln Leu Asp Trp Tyr
465                 470                 475                 480 gag gag tat cca acc acg ccg acc agt acc ttc gtt ctc aat ggt ttt   1488
Glu Glu Tyr Pro Thr Thr Pro Thr Ser Thr Phe Val Leu Asn Gly Phe
            485                 490                 495 att ttt gcc atg ctt gga ctt tac gac gtt atg aaa aca gct gat ggc   1536
Ile Phe Ala Met Leu Gly Leu Tyr Asp Val Met Lys Thr Ala Asp Gly
        500                 505                 510 gaa gga cag cga gta gct gag aag tta tgg atg tca gga ttg cac tca   1584
Glu Gly Gln Arg Val Ala Glu Lys Leu Trp Met Ser Gly Leu His Ser
    515                 520                 525 cta aaa gtg atg ttg ggt atg tat gat tcc ggc aca gga acg ctt tat   1632
Leu Lys Val Met Leu Gly Met Tyr Asp Ser Gly Thr Gly Thr Leu Tyr
530                 535                 540 gat ctt cgt cac ata atc aac cac gaa cag cct aat cgg gcc aga tgg   1680
Asp Leu Arg His Ile Ile Asn His Glu Gln Pro Asn Arg Ala Arg Trp
545                 550                 555                 560
```

```
gat tat cat act aca cat att gcg ctt atc cag gaa atg gcc atc att    1728
Asp Tyr His Thr Thr His Ile Ala Leu Ile Gln Glu Met Ala Ile Ile
                565                 570                 575 gac ggt gac cct ctg ttt gac acc act gct aaa aga tgg ata gat tat    1776
Asp Gly Asp Pro Leu Phe Asp Thr Thr Ala Lys Arg Trp Ile Asp Tyr
            580                 585                 590 ttt tac ggc aaa aga tct aag cac aat taa                            1806
Phe Tyr Gly Lys Arg Ser Lys His Asn
        595                 600

<210> SEQ ID NO 2
<211> LENGTH: 601
<212> TYPE: PRT
<213> ORGANISM: Achatina fulica

<400> SEQUENCE: 2

Met His Leu Thr Cys Val Arg Arg Ala Phe Arg Lys Val Asn Trp Leu
1               5                   10                  15

Leu Arg Ser Val Val Leu Leu Thr Gly Gly Cys Leu Thr Ile Leu
            20                  25                  30

Val Asn Trp Gln Trp Pro Asn Ser Arg Pro Tyr Tyr Trp Leu Arg Ser
            35                  40                  45

Asp Ala Glu Phe Ala Gly Gln Phe Val Ser Thr Ala Asp Ser Ser Gln
    50                  55                  60

Leu Phe Glu Asp Gln Thr Val Ser Cys Pro Pro Cys Pro Ser Ile Asp
65                  70                  75                  80

Asp Phe Pro Gln Ser Ala Gln Thr Leu Asp Leu Gln Ile Ile Asn Cys
                85                  90                  95

Ser Ile Asn Glu Ala Glu Thr Ile Glu Cys Arg Gln Asp Lys Gly Glu
            100                 105                 110

Val Tyr Met Pro Val Ser Phe Ile Asn Asn Tyr Phe Glu Val Phe Gly
        115                 120                 125

Asp Val Lys Arg Asp Gly Thr Ser Lys Leu Tyr Asn Phe Gln His Ala
    130                 135                 140

Tyr Gly Lys Ile His Pro Pro Gln Pro Val Tyr His Pro Gly Gly Val
145                 150                 155                 160

Phe Leu Asn Phe Glu Lys Tyr Asn Val Ala Ala Arg Glu Lys Ile Leu
                165                 170                 175

Cys Val Thr Ala Ser Asp Gly Val Pro Leu Ala Lys Gln Trp Asp Pro
            180                 185                 190

Ala Gly Tyr Tyr Tyr Ala Ile Ser Val Ala Gln Tyr Gly Leu Ser His
        195                 200                 205

His Ala Lys Gly Ile Leu Glu Gly Asn Pro Thr Pro Arg Leu Met Ala
    210                 215                 220

Gly Gly Gln Val Glu Glu Ser Arg Trp Glu Asn Thr Gly Pro Glu Met
225                 230                 235                 240

Glu Val Asn Ile Ala Glu Thr Thr Val Asp Gly Glu Met Met Arg Val
                245                 250                 255

Leu Ser Phe Ser Ala Pro Glu Ser Tyr Thr Ala Pro Gly Pro Val Leu
            260                 265                 270

Arg Leu Ser Thr Gln Glu Gln Thr Ile Cys Phe Asp Leu Gln Leu Thr
        275                 280                 285

Gly Pro Gly Gly Val Thr Val Gln Ile Lys Thr Arg Asn Gly Arg Thr
    290                 295                 300

Gly Tyr Ile His Phe Ile Leu Asp Asp Arg Tyr Met Glu Val Asn Gly
```

```
            305                 310                 315                 320
        Ser His Val Leu Tyr Gly Ile Gly Thr Lys Asn Leu Gly Lys Trp Val
                        325                 330                 335

His Leu Thr Arg Asp Ile Phe Val Asp Trp Met Lys Thr Leu His Asn
                    340                 345                 350

Ala Gln Phe Ser Ser Pro Thr Gln Phe Lys Glu Ile Asp Val Thr
                355                 360                 365

Leu His Gly Thr Gly Tyr Leu Asp Asn Leu Thr Leu Ser Thr Ser Ala
            370                 375                 380

His Asn Asp His Leu Ile His Ala Ala Asn Trp Leu Val Asn Asn Gln
        385                 390                 395                 400

Asp Ser Ala Gly Gly Trp Pro Thr Ser Ile Gly Met Lys Thr Gly Glu
                        405                 410                 415

Asn Ile Glu Leu Lys Pro Gly Trp Tyr Ser Ala Met Gly Gln Gly Gln
                    420                 425                 430

Ala Met Ser Thr Leu Val Arg Ala Tyr Asn Leu Thr Ala His Lys Tyr
                435                 440                 445

Tyr Leu Asp Thr Ala Val Arg Ala Leu His Leu Tyr Glu Leu Gly Ser
            450                 455                 460

Asp Val Gly Gly Val Arg Ala Arg Phe Leu Gly Gln Leu Asp Trp Tyr
        465                 470                 475                 480

Glu Glu Tyr Pro Thr Thr Pro Thr Ser Thr Phe Val Leu Asn Gly Phe
                        485                 490                 495

Ile Phe Ala Met Leu Gly Leu Tyr Asp Val Met Lys Thr Ala Asp Gly
                    500                 505                 510

Glu Gly Gln Arg Val Ala Glu Lys Leu Trp Met Ser Gly Leu His Ser
                515                 520                 525

Leu Lys Val Met Leu Gly Met Tyr Asp Ser Gly Thr Gly Thr Leu Tyr
            530                 535                 540

Asp Leu Arg His Ile Ile Asn His Glu Gln Pro Asn Arg Ala Arg Trp
        545                 550                 555                 560

Asp Tyr His Thr Thr His Ile Ala Leu Ile Gln Glu Met Ala Ile Ile
                        565                 570                 575

Asp Gly Asp Pro Leu Phe Asp Thr Thr Ala Lys Arg Trp Ile Asp Tyr
                    580                 585                 590

Phe Tyr Gly Lys Arg Ser Lys His Asn
                595                 600

<210> SEQ ID NO 3
<211> LENGTH: 617
<212> TYPE: PRT
<213> ORGANISM: Homo sapiens

<400> SEQUENCE: 3

Met Arg Cys Leu Ala Ala Arg Val Asn Tyr Lys Thr Leu Ile Ile Ile
1               5                   10                  15

Cys Ala Leu Phe Thr Leu Val Thr Val Leu Leu Trp Asn Lys Cys Ser
                20                  25                  30

Ser Asp Lys Ala Ile Gln Phe Pro Arg Arg Ser Ser Gly Phe Arg
            35                  40                  45

Val Asp Gly Phe Glu Lys Arg Ala Ala Ser Glu Ser Asn Asn Tyr
        50                  55                  60

Met Asn His Val Ala Lys Gln Gln Ser Glu Glu Ala Phe Pro Gln Glu
65                  70                  75                  80
```

```
Gln Gln Lys Ala Pro Pro Val Val Gly Gly Phe Asn Ser Asn Val Gly
                 85              90                  95
Ser Lys Val Leu Gly Leu Lys Tyr Glu Glu Ile Asp Cys Leu Ile Asn
            100                 105                 110
Asp Glu His Thr Ile Lys Gly Arg Arg Glu Gly Asn Glu Val Phe Leu
            115                 120                 125
Pro Phe Thr Trp Val Glu Lys Tyr Phe Asp Val Tyr Gly Lys Val Val
            130                 135                 140
Gln Tyr Asp Gly Tyr Asp Arg Phe Glu Phe Ser His Ser Tyr Ser Lys
145                 150                 155                 160
Val Tyr Ala Gln Arg Ala Pro Tyr His Pro Asp Gly Val Phe Met Ser
                165                 170                 175
Phe Glu Gly Tyr Asn Val Glu Val Arg Asp Arg Val Lys Cys Ile Ser
                180                 185                 190
Gly Val Glu Gly Val Pro Leu Ser Thr Gln Trp Gly Pro Gln Gly Tyr
                195                 200                 205
Phe Tyr Pro Ile Gln Ile Ala Gln Tyr Gly Leu Ser His Tyr Ser Lys
                210                 215                 220
Asn Leu Thr Glu Lys Pro Pro His Ile Glu Val Tyr Glu Thr Ala Glu
225                 230                 235                 240
Asp Arg Asp Lys Asn Lys Pro Asn Asp Trp Thr Val Pro Lys Gly Cys
                245                 250                 255
Phe Met Ala Asn Val Ala Asp Lys Ser Arg Phe Thr Asn Val Lys Gln
                260                 265                 270
Phe Ile Ala Pro Glu Thr Ser Glu Gly Val Ser Leu Gln Leu Gly Asn
                275                 280                 285
Thr Lys Asp Phe Ile Ile Ser Phe Asp Leu Lys Phe Leu Thr Asn Gly
                290                 295                 300
Ser Val Ser Val Val Leu Glu Thr Thr Glu Lys Asn Gln Leu Phe Thr
305                 310                 315                 320
Ile His Tyr Val Ser Asn Ala Gln Leu Ile Ala Phe Lys Glu Arg Asp
                325                 330                 335
Ile Tyr Tyr Gly Ile Gly Pro Arg Thr Ser Trp Ser Thr Val Thr Arg
                340                 345                 350
Asp Leu Val Thr Asp Leu Arg Lys Gly Val Gly Leu Ser Asn Thr Lys
                355                 360                 365
Ala Val Lys Pro Thr Lys Ile Met Pro Lys Lys Val Val Arg Leu Ile
                370                 375                 380
Ala Lys Gly Lys Gly Phe Leu Asp Asn Ile Thr Ile Ser Thr Thr Ala
385                 390                 395                 400
His Met Ala Ala Phe Phe Ala Ala Ser Asp Trp Leu Val Arg Asn Gln
                405                 410                 415
Asp Glu Lys Gly Gly Trp Pro Ile Met Val Thr Arg Lys Leu Gly Glu
                420                 425                 430
Gly Phe Lys Ser Leu Glu Pro Gly Trp Tyr Ser Ala Met Ala Gln Gly
                435                 440                 445
Gln Ala Ile Ser Thr Leu Val Arg Ala Tyr Leu Leu Thr Lys Asp His
                450                 455                 460
Ile Phe Leu Asn Ser Ala Leu Arg Ala Thr Ala Pro Tyr Lys Phe Leu
465                 470                 475                 480
Ser Glu Gln His Gly Val Lys Ala Val Phe Met Asn Lys His Asp Trp
                485                 490                 495
Tyr Glu Glu Tyr Pro Thr Thr Pro Ser Ser Phe Val Leu Asn Gly Phe
```

```
                500             505             510
Met Tyr Ser Leu Ile Gly Leu Tyr Asp Leu Lys Glu Thr Ala Gly Glu
            515             520             525

Lys Leu Gly Lys Glu Ala Arg Ser Leu Tyr Glu Arg Gly Met Glu Ser
            530             535             540

Leu Lys Ala Met Leu Pro Leu Tyr Asp Thr Gly Ser Gly Thr Ile Tyr
545             550             555             560

Asp Leu Arg His Phe Met Leu Gly Ile Ala Pro Asn Leu Ala Arg Trp
                565             570             575

Asp Tyr His Thr Thr His Ile Asn Gln Leu Gln Leu Leu Ser Thr Ile
            580             585             590

Asp Glu Ser Pro Val Phe Lys Glu Phe Val Lys Arg Trp Lys Ser Tyr
            595             600             605

Leu Lys Gly Ser Arg Ala Lys His Asn
            610             615

<210> SEQ ID NO 4
<211> LENGTH: 585
<212> TYPE: PRT
<213> ORGANISM: Danio rerio

<400> SEQUENCE: 4

Met Arg Cys Leu Val Ala Arg Ile Asn His Lys Thr Leu Ile Val Ile
1               5               10              15

Cys Ala Val Phe Ala Leu Ile Thr Ile Leu Leu Trp Asn Lys Cys Ser
            20              25              30

Ser Asp Lys Asp Leu Pro Ser Pro Val Arg Pro Leu Glu Phe Ala Ala
            35              40              45

Pro Thr Pro Glu Lys Glu Glu Asn Glu Gly Gln Ala Pro Glu Ala
        50              55              60

Pro Pro Gly Ser Arg Glu Val Ala Tyr Glu Gln Ile Asp Cys Leu Ile
65              70              75              80

Asn Glu Asp Val Leu Ile Lys Gly Arg Arg Glu Gly Gly Glu Val Tyr
            85              90              95

Leu Pro Phe Ser Trp Val Glu Lys Tyr Phe Asp Val Tyr Gly Arg Leu
            100             105             110

Val Gln Tyr Asp Gly Met Glu Arg Phe Glu Phe Ser His Ser Tyr Ser
            115             120             125

Arg Val Tyr Ala Gln Arg Glu Pro Tyr His Pro Asp Gly Val Phe Met
            130             135             140

Ser Phe Glu Gly Tyr Asn Val Glu Val Arg Asp Arg Val Lys Cys Ile
145             150             155             160

Ser Gly Val Glu Gly Val Pro Ile Ser Thr Gln Trp Gly Pro Gln Gly
                165             170             175

Tyr Phe Tyr Pro Ile Gln Ile Ala Gln Tyr Gly Leu Ser His Tyr Ser
            180             185             190

Lys Asn Leu Thr Glu Lys Pro Pro Asp Ile Lys Ile Tyr Gly Met Leu
            195             200             205

Glu Glu Lys Glu Gly Gly Ser Ser Gln Trp Asp Val Pro Lys Gly Cys
            210             215             220

Thr Leu Ser Lys Ile Gln Asp Gln Gly Arg Ser Gly Phe Val His His
225             230             235             240

Phe Val Thr Ala Glu Asn Ser Glu Gly Val Ser Leu Val Leu Asp Asn
                245             250             255
```

```
Ala Lys Asp Phe Val Leu Thr Phe Asp Val Lys Phe Ile Ser Asn Gly
            260                 265                 270

Ser Val Ser Val Val Leu Glu Thr Thr Glu Lys Gly Pro Tyr Phe Ile
275                 280                 285

Ile His Tyr Ile Thr Ser Pro Leu Leu Leu Ser Phe Lys Asp Arg Glu
        290                 295                 300

Val Ile Tyr Gly Ile Gly Pro Arg Ala Thr Trp Ser Thr Val Ser Arg
305                 310                 315                 320

Asp Leu Val Thr Asp Leu Arg Lys Gly Val Gly Leu Ser Asn Thr Lys
                325                 330                 335

Val Val Lys Ala Thr Lys Ile Met Pro Arg Arg Val Val Gln Leu Val
            340                 345                 350

Leu Lys Gly Ser Gly Phe Ile Ser Asn Ile Thr Val Ser Ser Thr Ala
        355                 360                 365

His Met Ala Ala Phe Phe Ala Ala Ser Asp Trp Leu Leu His Asn Gln
    370                 375                 380

Asp Glu His Gly Gly Trp Pro Ile Lys Val Thr Arg Lys Leu Gly Glu
385                 390                 395                 400

Gly Phe Lys Ser Leu Glu Pro Gly Trp Tyr Ser Ala Met Ala Gln Gly
                405                 410                 415

Gln Ala Met Ser Thr Leu Val Arg Ala Tyr Leu Val Thr His Asn Pro
            420                 425                 430

Ser Tyr Leu Gly Ala Ala Ile Arg Ala Thr Ser Pro Phe Lys Arg Thr
        435                 440                 445

Pro Glu Gln His Gly Val Lys Ala Thr Phe Met Asn Lys Phe Asp Trp
    450                 455                 460

Tyr Glu Glu Tyr Pro Thr Thr Pro Ser Ser Phe Val Leu Asn Gly Phe
465                 470                 475                 480

Ile Tyr Ser Leu Ile Gly Leu Tyr Asp Val Ala Glu Thr Ala Gly Asn
                485                 490                 495

Lys Leu Gly Arg Glu Ala Gly Ile Leu Phe Ser Gln Gly Leu Glu Ser
            500                 505                 510

Leu Lys Ala Met Leu Pro Leu Phe Asp Thr Gly Ser Gly Thr Val Tyr
        515                 520                 525

Asp Leu Arg His Phe Thr Leu Gly Val Ala Pro Asn Leu Ala Arg Trp
    530                 535                 540

Asp Tyr His Thr Thr His Ile Asn Gln Leu Gln Leu Leu Ala Ser Ile
545                 550                 555                 560

Asp Gly Ala Pro Ile Phe Arg Asp Tyr Val Lys Arg Trp Lys Thr Tyr
                565                 570                 575

Leu Lys Gly Gly Arg Ala Lys His Asn
            580                 585

<210> SEQ ID NO 5
<211> LENGTH: 616
<212> TYPE: PRT
<213> ORGANISM: Caenorhabditis elegans

<400> SEQUENCE: 5

Met Lys Cys Leu Arg Trp Arg Ser Asn Arg His Arg Ile Tyr Leu Leu
1               5                   10                  15

Val Ala Cys Gly Ala Leu Phe Leu Leu Asn Arg His Leu Thr Gln Glu
                20                  25                  30

Glu Ser Arg Ile Asp Glu Glu Asp Glu Glu Leu Thr Gln Val Asp Val
            35                  40                  45
```

```
Asn Glu Asp Asp Lys Lys Ile Glu Cys Glu Pro Pro Gly Ser Ile Glu
         50                  55                  60

Ser Lys Cys Ile Ala Asp Asn Gly Lys Ser Met Lys Cys Trp Lys Asp
 65                  70                  75                  80

Glu Glu Asp Val Tyr Phe Pro Val Ser Tyr Leu Lys Lys Arg Phe Asp
                     85                  90                  95

Met Thr Gly Lys Leu Gly Lys Asp Gly Ser Thr Phe Glu Leu Tyr Thr
                100                 105                 110

Ser Tyr Ala Lys Met Arg Ser Pro Asp Ser Thr Tyr Asp Pro Leu Gly
            115                 120                 125

Pro Phe Gly His Phe Ser Thr Tyr Ser Val Glu Thr Arg Asp Arg Val
        130                 135                 140

Arg Cys Val Ser Ala Lys Thr Asp Val Pro Met Ser Thr Gln Trp Asp
145                 150                 155                 160

Pro Ile Pro Tyr Tyr Tyr Pro Ile Gln Ile Ser Gln Tyr Gly Leu Gln
                165                 170                 175

His Tyr Ser Arg Met Lys Leu Asp Ser Ile Ser Asn Lys Ser Glu Ala
            180                 185                 190

Ser Pro Lys Asp Asp Val Ile Leu Gly Val Asn Ser Lys Glu Trp Lys
        195                 200                 205

Gly Ala Ala Gly Met His Glu Thr Thr Glu Arg Leu Phe Phe Asn Asp
210                 215                 220

Glu Gln Met Gly Lys Val Val Asn Ile Ser Ala Gly Ala Ala Leu Ala
225                 230                 235                 240

Asn Ala Gly Ala Tyr Val Tyr Leu Asp Lys Ser Pro Asp Leu His Val
                245                 250                 255

Ile Ser Phe Asp Trp Lys Pro Tyr Glu Ala Asn Ser Ser Phe Thr Val
            260                 265                 270

Leu Ala Lys Met Lys Gln Asp Asp Leu Leu Val Leu Ile Asn Tyr Val
        275                 280                 285

Tyr Ser Glu Gly Asn Gly Lys Cys Val Trp Gln Glu Glu Arg Ile
        290                 295                 300

Ser Asp Asp Tyr Ile Val Gln Lys Pro Lys Asp Gly Gln Val Ser
305                 310                 315                 320

Tyr Ser Tyr Ser Tyr Ile Gly Asn Ser Pro Ile Gly Glu Trp Ser Thr
                325                 330                 335

Val Thr Arg Asp Leu Leu Val Asp Val Ala Arg Ala Leu Ser Ser Gly
            340                 345                 350

Asp Asn Arg Lys Lys Asp Asp Asn Val Val Leu His Ala Gly Asp Leu
        355                 360                 365

Arg Leu Val Ser Leu Gly Phe Arg Gly Glu Leu Thr Val Lys Gln Lys
370                 375                 380

Ile Thr Gln Arg Arg Glu Gln His Ser His Ala Phe Tyr Ala Ala Ala
385                 390                 395                 400

Asp Trp Leu Val Lys Asn Gln Asn Asp Arg Gly Gly Trp Ser Val Pro
                405                 410                 415

Val Glu Arg Ser Ile Ala Glu Arg Lys Leu Val Leu Pro Pro Gly Trp
            420                 425                 430

His Ser Ala Met Ala Gln Gly His Gly Ile Ser Val Leu Thr Arg Ala
        435                 440                 445

Phe Lys His Phe Asn Asp Glu Lys Tyr Leu Lys Ser Ala Ala Lys Ala
450                 455                 460
```

-continued

```
Leu Lys Leu Phe Lys Ile Asn Ser Ser Asp Gly Gly Val Arg Gly Glu
465                 470                 475                 480

Phe Phe Gly Asn Ile Trp Tyr Glu Glu Tyr Pro Thr Thr Pro Gly Ser
                485                 490                 495

Phe Val Leu Asn Gly Phe Leu Tyr Ser Leu Ile Gly Leu Tyr Asp Leu
            500                 505                 510

Ser Gln Leu Glu Leu Met Ile Asp Glu Asn Asp Glu Thr Met Arg Ala
        515                 520                 525

Lys Ile Gln Glu Ala Gln Leu Tyr Ser Ala Gly Val Arg Ser Leu
    530                 535                 540

Lys Gln Leu Leu Pro Leu Tyr Asp Thr Gly Ser Gly Thr Ile Tyr Asp
545                 550                 555                 560

Leu Arg His Val Ala Leu Gly Thr Ala Pro Asn Leu Ala Arg Trp Asp
                565                 570                 575

Tyr His Ala Val His Val Tyr Leu Leu Lys Trp Ile Ala Gly Ile Glu
                580                 585                 590

Lys Asp Glu Val Leu Ser Lys Thr Ala Asp Arg Trp Ile Gly Tyr Ala
            595                 600                 605

Tyr Gly Lys Arg Ala Lys His Asn
    610                 615

<210> SEQ ID NO 6
<211> LENGTH: 50
<212> TYPE: DNA
<213> ORGANISM: Artificial Sequence
<220> FEATURE:
<223> OTHER INFORMATION: Synthetic oligo-dT primer bearinig a XhoI site
      for reverse transcription

<400> SEQUENCE: 6
gagagagaga gagagagaga actagtctcg agtttttttt tttttttttt           50

<210> SEQ ID NO 7
<211> LENGTH: 14
<212> TYPE: DNA
<213> ORGANISM: Artificial Sequence
<220> FEATURE:
<223> OTHER INFORMATION: Synthetic sense oligo-nucleotide of EcoRI
      adaptor

<400> SEQUENCE: 7
aattcggcac gagg                                                  14

<210> SEQ ID NO 8
<211> LENGTH: 10
<212> TYPE: DNA
<213> ORGANISM: Artificial Sequence
<220> FEATURE:
<223> OTHER INFORMATION: Synthetic anti-sense oligo-nucleotide of EcoRI
      adaptor

<400> SEQUENCE: 8
cctcgtgccg                                                       10

<210> SEQ ID NO 9
<211> LENGTH: 20
<212> TYPE: DNA
<213> ORGANISM: Artificial Sequence
<220> FEATURE:
<223> OTHER INFORMATION: Synthetic sense primer for PCR cloning of
      heparosan-glucuronate-5-epimerase

<400> SEQUENCE: 9
```
tggtatgagg aatatccaac                                            20

<210> SEQ ID NO 10
<211> LENGTH: 20
<212> TYPE: DNA
<213> ORGANISM: Artificial Sequence
<220> FEATURE:
<223> OTHER INFORMATION: Synthetic sense primer for PCR cloning of
      heparosan-glucuronate-5-epimerase

<400> SEQUENCE: 10
tcttttgtgc tcaatggatt                                            20

<210> SEQ ID NO 11
<211> LENGTH: 26
<212> TYPE: DNA
<213> ORGANISM: Artificial Sequence
<220> FEATURE:
<223> OTHER INFORMATION: Synthetic sense primer for PCR cloning of
      heparosan-glucuronate-5-epimerase

<400> SEQUENCE: 11
tattcactta ttggacttta tgatct                                     26

<210> SEQ ID NO 12
<211> LENGTH: 17
<212> TYPE: DNA
<213> ORGANISM: Artificial Sequence
<220> FEATURE:
<223> OTHER INFORMATION: Synthetic anti-sense primer for PCR cloning of
      heparosan-glucuronate-5-epimerase

<400> SEQUENCE: 12
ttaattatgt tttgccc                                               17

<210> SEQ ID NO 13
<211> LENGTH: 24
<212> TYPE: DNA
<213> ORGANISM: Artificial Sequence
<220> FEATURE:
<223> OTHER INFORMATION: Synthetic anti-sense primer for PCR cloning of
      heparosan-glucuronate-5-epimerase

<400> SEQUENCE: 13
atgataatcc catcttgcaa gatt                                       24

<210> SEQ ID NO 14
<211> LENGTH: 20
<212> TYPE: DNA
<213> ORGANISM: Artificial Sequence
<220> FEATURE:
<223> OTHER INFORMATION: Synthetic sense primer for insert check PCR
      named as T3 primer

<400> SEQUENCE: 14
aattaaccct cactaaaggg                                            20

<210> SEQ ID NO 15
<211> LENGTH: 20
<212> TYPE: DNA
<213> ORGANISM: Artificial Sequence
<220> FEATURE:
<223> OTHER INFORMATION: Synthetic anti-sense primer for insert check
      PCR named as T7 primer

<400> SEQUENCE: 15

```
taatacgact cactataggg                                           20
```

<210> SEQ ID NO 16
<211> LENGTH: 255
<212> TYPE: DNA
<213> ORGANISM: Achatina fulica

<400> SEQUENCE: 16

```
tggtatgagg aatatccaac cacgccgacc agtaccttcg ttctcaatgg ttttattttt   60
gccatgcttg gactttacga cgttatgaaa acagctgatg gcgaaggaca gcgagtagct  120
gagaagttat ggatgtcagg attgcactca ctaaaagtga tgttgggtat gtatgattcc  180
ggcacaggaa cgctttatga tcttcgtcac ataatcaacc acgaacagcc taatcttgca  240
agatgggatt atcat                                                  255
```

<210> SEQ ID NO 17
<211> LENGTH: 20
<212> TYPE: DNA
<213> ORGANISM: Artificial Sequence
<220> FEATURE:
<223> OTHER INFORMATION: Synthetic sense primer for inverse PCR

<400> SEQUENCE: 17

```
tggatgtcag gattgcactc                                           20
```

<210> SEQ ID NO 18
<211> LENGTH: 20
<212> TYPE: DNA
<213> ORGANISM: Artificial Sequence
<220> FEATURE:
<223> OTHER INFORMATION: Synthetic anti-sense primer for inverse PCR

<400> SEQUENCE: 18

```
cttcgccatc agctgttttc                                           20
```

<210> SEQ ID NO 19
<211> LENGTH: 20
<212> TYPE: DNA
<213> ORGANISM: Artificial Sequence
<220> FEATURE:
<223> OTHER INFORMATION: Synthetic sense primer for nested PCR

<400> SEQUENCE: 19

```
ggtatgtatg attccggcac                                           20
```

<210> SEQ ID NO 20
<211> LENGTH: 20
<212> TYPE: DNA
<213> ORGANISM: Artificial Sequence
<220> FEATURE:
<223> OTHER INFORMATION: Synthetic anti-sense primer for nested PCR

<400> SEQUENCE: 20

```
tcgtaaagtc caagcatggc                                           20
```

<210> SEQ ID NO 21
<211> LENGTH: 20
<212> TYPE: DNA
<213> ORGANISM: Artificial Sequence
<220> FEATURE:
<223> OTHER INFORMATION: Synthetic sense primer for PCR cloning of
       heparosan-glucuronate-5-epimerase

<400> SEQUENCE: 21
tgatgagggt actgtcgttc 20

<210> SEQ ID NO 22
<211> LENGTH: 23
<212> TYPE: DNA
<213> ORGANISM: Artificial Sequence
<220> FEATURE:
<223> OTHER INFORMATION: Synthetic anti-sense primer for PCR cloning of
      heparosan-glucuronate-5-epimerase

<400> SEQUENCE: 22
ttaattgtgc ttagatcttt tgc 23

<210> SEQ ID NO 23
<211> LENGTH: 1049
<212> TYPE: DNA
<213> ORGANISM: Achatina fulica

<400> SEQUENCE: 23
tgatgagggt actgtcgttc agtgctccag aatcatatac tgcccctggt cctgttcttc    60
gtttgagcac gcaagagcag acaatctgtt ttgacttaca actgactgga cctggtgggg   120
tcactgtaca aataaagacc aggaacggca gaacaggcta catacatttt atccttgatg   180
acagatacat ggaggttaac ggaagccacg tttatatgg aataggcacg aagaatcttg    240
gaaaatgggt acatctaaca agagatatct ttgtggactg gatgaaaacc ctgcataacg   300
cacaattcag ctcaccgacg caattcaaag agatagtgga tgtgacactg catggaactg   360
ggtatcttga taacttaaca ttatctacat ctgcgcacaa cgaccatctt atccatgctg   420
cgaactggct agttaataat caagacagtg ctggaggctg gccaactagc attggaatga   480
aaaccggtga aaacatcgaa ctgaaacctg gctggtactc cgctatgggt caaggccaag   540
caatgtctac acttgtccga gcatataacc tgactgcgca taaatattac ctggataccg   600
ccgtacgagc tttacattta tatgagttgg gatctgatgt tggtggtgtt cgagctcgtt   660
tcctgggaca acttgattgg tatgaggagt atccaaccac gccgaccagt accttcgttc   720
tcaatggttt tattttttgcc atgcttggac tttacgacgt tatgaaaaca gctgatggcg   780
aaggacagcg agtagctgag aagttatgga tgtcaggatt gcactcacta aaagtgatgt   840
tgggtatgta tgattccggc acaggaacgc tttatgatct tcgtcacata atcaaccacg   900
aacagcctaa tcgggccaga tgggattatc atactcacac tattgcgctt atccaggaaa   960
tggccatcat tgacggtgac cctctgtttg acaccactgc taaaagatgg atagattatt  1020
tttacggcaa aagatctaag cacaattaa                                   1049

<210> SEQ ID NO 24
<211> LENGTH: 27
<212> TYPE: DNA
<213> ORGANISM: Artificial Sequence
<220> FEATURE:
<223> OTHER INFORMATION: Synthetic sense primer for 5' RACE of
      heparosan-glucuronate-5-epimerase

<400> SEQUENCE: 24
ccatcctaat acgactcact atagggc 27

<210> SEQ ID NO 25
<211> LENGTH: 25
<212> TYPE: DNA
<213> ORGANISM: Artificial Sequence
<220> FEATURE:
<223> OTHER INFORMATION: Synthetic anti-sense primer for 5' RACE of heparosan-glucuronate-5-epimerase

<400> SEQUENCE: 25
cattgcttgg ccttgaccca tagcg                                                    25

<210> SEQ ID NO 26
<211> LENGTH: 23
<212> TYPE: DNA
<213> ORGANISM: Artificial Sequence
<220> FEATURE:
<223> OTHER INFORMATION: Synthetic sense primer for nested PCR

<400> SEQUENCE: 26
actcactata gggctcgagc ggc                                                      23

<210> SEQ ID NO 27
<211> LENGTH: 26
<212> TYPE: DNA
<213> ORGANISM: Artificial Sequence
<220> FEATURE:
<223> OTHER INFORMATION: Synthetic anti-sense primer for nested PCR

<400> SEQUENCE: 27
tctctttgaa ttgcgtcggt gagctg                                                   26

<210> SEQ ID NO 28
<211> LENGTH: 1200
<212> TYPE: DNA
<213> ORGANISM: Achatina fulica

<400> SEQUENCE: 28
actcactata gggctcgagc ggccgcccgg gcaggtattt gaatattctc acttattcca              60
ggattttcag tttttatcgc atgtttgtta caacactcac tggagaggat atgcaccttg             120
catgtgtaag aagagccttt cgtaaagtta actggctgct tcgttctgtt gttctacttt             180
tgaccggagg atgtttgaca atattggtga actggcaatg gcccaatagt agaccatatt             240
attggctcag atcagatgca gagtttgctg acagtttgt atcaacggcc gacagctctc              300
agttgttcga agatcaaaca gtctcttgtc cgccgtgtcc aagtatagac gactttcctc             360
agtcagcaca aactttggac ctgcagataa ttaactgttc gataaatgaa gcagagacaa             420
ttgaatgtag acaagacaaa ggagaagtct acatgccagt ctccttcatc aacaactatt             480
ttgaggtctt tggagatgtg aaacgtgacg gcaccagtaa actgtacaat tttcagcatg             540
cttacggcaa gatccatccg ccccagcctg tctatcaccc aggagggta ttcctaaatt              600
ttgagaagta caatgtagcg gctagagaaa agattctttg tgtgacagct tctgatggcg             660
tgccattagc caaacagtgg gatcccgctg ggtactacta cgccatttca gttgcacagt             720
atggtctgag tcatcatgcc aagggtattc tagaaggaaa cccaacgccc aggctgatgg             780
ctggtggcca ggtggaagag tcaaggtggg aaaatacagg ccctgagatg gaagttaata             840
tcgcagagac aactgtagat ggagaaatga tgagggtact gtcgttcagt gctccagaat             900
catatactgc ccctggtcct gttcttcgtt tgagcacgca agagcagaca atctgttttg             960
acttacaact gactggacct ggtggggtca ctgtacaaat aaagaccagg aacggcagaa            1020
caggctacat acatttatc cttgatgaca gatacatgga ggttaacgga agccacgttt             1080
tatatggaat aggcacgaag aatcttggaa aatgggtaca tctaacaaga gatatctttg            1140
tggactggat gaaaaccctg cataacgcac aattcagctc accgacgcaa ttcaaagaga            1200

```
<210> SEQ ID NO 29
<211> LENGTH: 30
<212> TYPE: DNA
<213> ORGANISM: Artificial Sequence
<220> FEATURE:
<223> OTHER INFORMATION: Synthetic sense primer for preparation of an
      expression vector encoding heparosan-glucuronate-5-epimerase

<400> SEQUENCE: 29
acagaattct aactggcaat ggcccaatag                                          30

<210> SEQ ID NO 30
<211> LENGTH: 34
<212> TYPE: DNA
<213> ORGANISM: Artificial Sequence
<220> FEATURE:
<223> OTHER INFORMATION: Synthetic anti-sense primer for preparation of
      an expression vector encoding heparosan-glucuronate-5-epimerase

<400> SEQUENCE: 30
tgtgcggccg cttaattgtg cttagatctt ttgc                                     34

<210> SEQ ID NO 31
<211> LENGTH: 22
<212> TYPE: PRT
<213> ORGANISM: Artificial Sequence
<220> FEATURE:
<223> OTHER INFORMATION: Synthetic sequence, secretion signal peptide of
      the kappa-chain of mouse immunoglobulin

<400> SEQUENCE: 31

Met His Phe Gln Val Gln Ile Phe Ser Phe Leu Leu Ile Ser Ala Ser
1               5                   10                  15

Val Ile Met Ser Arg Gly
            20

<210> SEQ ID NO 32
<211> LENGTH: 8
<212> TYPE: PRT
<213> ORGANISM: Artificial Sequence
<220> FEATURE:
<223> OTHER INFORMATION: Synthetic FLAG peptide

<400> SEQUENCE: 32

Asp Tyr Lys Asp Asp Asp Asp Lys
1               5

<210> SEQ ID NO 33
<211> LENGTH: 90
<212> TYPE: DNA
<213> ORGANISM: Artificial Sequence
<220> FEATURE:
<223> OTHER INFORMATION: Synthetic, recombinant DNA sequence encoding
      secretion signal peptide of the kappa-chain of mouse
      immunoglobulin and FLAG peptide
<220> FEATURE:
<221> NAME/KEY: CDS
<222> LOCATION: (1)..(90)

<400> SEQUENCE: 33 atg cat ttt caa gtg cag att ttc agc ttc ctg cta atc agt gcc tca          48
Met His Phe Gln Val Gln Ile Phe Ser Phe Leu Leu Ile Ser Ala Ser
1               5                   10                  15 gtc ata atg tca cgt gga gat tac aag gac gac gat gac aag                  90
Val Ile Met Ser Arg Gly Asp Tyr Lys Asp Asp Asp Asp Lys
            20                  25                  30
```

```
<210> SEQ ID NO 34
<211> LENGTH: 30
<212> TYPE: PRT
<213> ORGANISM: Artificial Sequence
<220> FEATURE:
<223> OTHER INFORMATION: Synthetic Construct

<400> SEQUENCE: 34

Met His Phe Gln Val Gln Ile Phe Ser Phe Leu Leu Ile Ser Ala Ser
1               5                   10                  15

Val Ile Met Ser Arg Gly Asp Tyr Lys Asp Asp Asp Lys
            20                  25                  30

<210> SEQ ID NO 35
<211> LENGTH: 36
<212> TYPE: DNA
<213> ORGANISM: Artificial Sequence
<220> FEATURE:
<223> OTHER INFORMATION: Synthetic sense primer for preparation of an
      expression vector named as pFBIF1

<400> SEQUENCE: 35
acaggatcca ccatgcattt tcaagtgcag attttc                              36

<210> SEQ ID NO 36
<211> LENGTH: 50
<212> TYPE: DNA
<213> ORGANISM: Artificial Sequence
<220> FEATURE:
<223> OTHER INFORMATION: Synthetic anti-sense primer for preparation of
      an expression vector named as pFBIF1

<400> SEQUENCE: 36
acagaattct tgtcatcgtc gtccttgtaa tctccacgtg acattatgac                50

<210> SEQ ID NO 37
<211> LENGTH: 29
<212> TYPE: DNA
<213> ORGANISM: Artificial Sequence
<220> FEATURE:
<223> OTHER INFORMATION: Synthetic sense primer for preparation of an
      expression vector encoding heparosan-glucuronate-5-epimerase

<400> SEQUENCE: 37
acagtcgaca actggcaatg gcccaatag                                      29

<210> SEQ ID NO 38
<211> LENGTH: 26
<212> TYPE: DNA
<213> ORGANISM: Artificial Sequence
<220> FEATURE:
<223> OTHER INFORMATION: Synthetic anti-sense primer for preparation of
      an expression vector encoding heparosan-glucuronate-5-epimerase

<400> SEQUENCE: 38
acaggtacct taattgtgct tagatc                                         26

<210> SEQ ID NO 39
<211> LENGTH: 23
<212> TYPE: DNA
<213> ORGANISM: Artificial Sequence
<220> FEATURE:
<223> OTHER INFORMATION: Synthetic sense primer for preparation of an
      expression vector named as pFBIF2

<400> SEQUENCE: 39
acagaattcc accatgcatt ttc                                            23
```

```
<210> SEQ ID NO 40
<211> LENGTH: 28
<212> TYPE: DNA
<213> ORGANISM: Artificial Sequence
<220> FEATURE:
<223> OTHER INFORMATION: Synthetic anti-sense primer for preparation of
      an expression vector named as pFBIF2

<400> SEQUENCE: 40
acagtcgacc ttgtcatcgt cgtccttg                                            28

<210> SEQ ID NO 41
<211> LENGTH: 17
<212> TYPE: DNA
<213> ORGANISM: Artificial Sequence
<220> FEATURE:
<223> OTHER INFORMATION: Synthetic sense primer for insert check PCR
      named as M13 Forward (-40)

<400> SEQUENCE: 41
gttttcccag tcacgac                                                        17

<210> SEQ ID NO 42
<211> LENGTH: 17
<212> TYPE: DNA
<213> ORGANISM: Artificial Sequence
<220> FEATURE:
<223> OTHER INFORMATION: Synthetic anti-sense primer for insert check
      PCR named as M13 Reverse

<400> SEQUENCE: 42
caggaaacag ctatgac                                                        17
```

HEPAROSAN-GLUCURONIC ACID-5-EPIMERASE, AND METHOD FOR PRODUCING POLYSACCHARIDE USING SAME

CROSS REFERENCE TO RELATED APPLICATIONS

This application is a National Stage of International Application No. PCT/JP2014/065533 filed Jun. 12, 2014, claiming priority based on Japanese Patent Application No. 2013-123435 filed Jun. 12, 2013, the contents of all of which are incorporated herein by reference in their entirety.

TECHNICAL FIELD

The present invention relates to a heparosan-glucuronate 5-epimerase (heparosan-glucuronic acid-5-epimerase). More specifically, the present invention relates to an enzyme derived from *Achatina fulica*, the enzyme having activity of epimerizing glucuronic acid residues of N-acetyl heparosan to iduronic acid residues, and/or activity of epimerizing iduronic acid residues of completely desulfated N-acetylated heparin to glucuronic acid residues; to a polypeptide having such activity; to a nucleic acid encoding the polypeptide; to a vector including the nucleic acid; to a host cell harboring the nucleic acid and/or the vector; to a method for producing the polypeptide; to a method for producing a polysaccharide in which hexuronic acid residues has been epimerized, the method employing the enzyme and/or the polypeptide; and to others.

BACKGROUND ART

The present specification may employ the following abbreviations.
GAG: glycosaminoglycan
PG: proteoglycan
GlcNAc: N-acetyl glucosamine
GlcNS: N-sulfated glucosamine
GlcN: glucosamine
GlcA: glucuronic acid
IdoA: iduronic acid
IdoA(2S): 2-O-sulfated iduronic acid
HexA: hexuronic acid
aMan: 2,5-anhydromannose
AS: acharan sulfate
ACH: acharan (2-O-desulfated AS)
NAH: N-acetyl heparosan
NSH: N-deacetylated N-sulfated heparosan
HEP: heparin
CDSNAc-HEP: completely desulfated N-acetylated heparin
CDSNS-HEP: completely desulfated N-resulfated heparin
HS: heparan sulfate
C5-epi: heparosan-N-sulfate-glucuronate 5-epimerase
HG-5epi: heparosan-glucuronate 5-epimerase It is known that acharan sulfate (AS) is a type of glycosaminoglycan (GAG), which is isolated from *Achatina fulica* and is known to be a linear GAG having a structure in which disaccharides formed of GlcNAc and IdoA(2S) (-[4GlcNAcα1-4IdoA(2S)α1]-), represented by the following structural formula (1), are repeatedly polymerized (Non-Patent Documents 1 and 2). Also, AS is known to have physiological activities similar to those of heparin (HEP) and heparan sulfate (HS), which are GAG having the carbohydrate backbone common to AS. Specifically, such activities include angiogenic inhibitory activity (Non-Patent Document 3), immunostimulatory activity (Non-Patent Document 4), hypoglycemic activity (Non-Patent Document 4), anti-coagulation activity (Non-Patent Document 5), anti-tumor activity (Non-Patent Document 6), and adhesion inhibitory activity against *Helicobacter pylori* (Non-Patent Document 7).

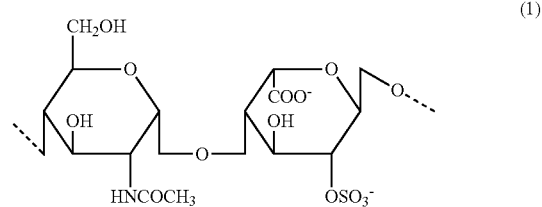

(1)

Biosynthesis of HEP and HS has been elucidated through analyses of carbohydrate structures provided by knock-out mice or mutant cells, and experiments evaluating substrate specificity of enzymes. The elucidated mechanism of the biosynthesis includes synthesis of N-acetyl heparosan (NAH), which is a GAG having a structure in which disaccharide units being formed of GlcNAc and GlcA (-[4GlcNAcα1-4GlcAβ1]-) are repeatedly polymerized; N-deacetylation and N-sulfation; epimerization of GlcA residues to IdoA residues; and O-sulfation, in this order (Non-Patent Documents 8 and 9). Among these steps, epimerization of GlcA residues to IdoA residues is catalyzed by a heparosan-N-sulfate-glucuronate 5-epimerase (C5-epi, EC: 5.1.3.17). Thus, all the known members of C5-epi involved in biosynthesis of HEP and HS are known to act on, as a substrate, N-deacetylated N-sulfated heparosan (NSH), which is a GAG generated through N-deacetylation and N-sulfation of NAH, and to not act on NAH itself (Non-Patent Documents 10 to 14 and Patent Documents 1 and 2).

Regarding *Achatina fulica*, proteome analysis has been carried out to collectively identify a group of enzymes involved in biosynthesis of proteoglycan (PG). The analysis has revealed a variety of enzymes involved in biosynthesis of PG core protein or GAG, based on the homology to a known protein (Non-Patent Document 15). Regarding synthetic pathway of HEP and HS, proteins, which are thought to serve as NAH synthase, N-deacetylase/N-sulfotransferase, and O-sulfotransferase have been found. However, no protein having a homology to C5-epi, which is a known epimerase, has been identified. In addition, regarding *Achatina fulica*, the enzymatic cascade in biosynthesis of AS has not been elucidated. Thus, the substrate on which an IdoA synthase acts and the product obtainable by the synthase reaction have not been identified.

PRIOR ART DOCUMENTS

Patent Documents

Patent Document 1: WO 1998/048006, pamphlet
Patent Document 2: WO 2002/046379, pamphlet

Non-Patent Documents

Non-Patent Document 1: Kim Y. S., Jo Y. Y., Chang I. M., Toida T, Park Y, Linhardt R. J., J. Biol. Chem., 1996 May 17; 271(20): 11750-5.

Non-Patent Document 2: Kim Y. S., Ahn M. Y., Wu S. J., Kim D. H., Toida T, Teesch L. M, Park Y., Yu G., Lin J., Linhardt R. J., Glycobiology, 1998 September; 8(9): 869-77.

Non-Patent Document 3: Ghosh A. K., Hirasawa N, Lee Y. S., Kim Y. S., Shin K. H., Ryu N., Ohuchi K., Br. J. Pharmacol., 2002 October; 137(4): 441-8.

Non-Patent Document 4: Shim J. Y., Lee Y. S., Jung S. H., Choi H. S., Shin K. H., Kim Y. S., Arch. Pharm. Res., 2002 December; 25(6): 889-94.

Non-Patent Document 5: Li D. W., Lee I. S., Sim J. S., Toida T, Linhardt R. J., Kim Y. S., Thromb Res., 2004; 113(1): 67-73.

Non-Patent Document 6: Joo E. J., Yang H., Park Y., Park N. Y., Toida T., Linhardt R. J., Kim Y. S., J. Cell Biochem., 2010 Aug. 1; 110(5): 1272-8.

Non-Patent Document 7: Sim J. S., Hahn B. S., Im A. R., Park Y., Shin J. E., Bae E. A., Kim D. H., Kim Y. S., Glycoconj. J., 2011 August; 28(6): 411-8.

Non-Patent Document 8: Lindahl U., Kusche-Gullberg M, Kjellen L., J. Biol. Chem., 1998 Sep. 25; 273(39): 24979-82.

Non-Patent Document 9: Esko J. D., Lindahl U., J. Clin. Invest., 2001 July; 108(2): 169-73.

Non-Patent Document 10: Campbell P., Hannesson H. H., Sandback D., Roden L., Lindahl U., Li J. P., J. Biol. Chem., 1994 Oct. 28; 269(43): 26953-8.

Non-Patent Document 11: Li J., Hagner-McWhirter A., Kjellen L., Palgi J., Jalkanen M., Lindahl U., J. Biol. Chem., 1997 Oct. 31; 272(44): 28158-63.

Non-Patent Document 12: Hagner-Mcwhirter A., Lindahl U., Li J. P., Biochem. J., 2000 Apr. 1; 347 Pt 1: 69-75.

Non-Patent Document 13: Li J. P., Gong F., El Darwish K., Jalkanen M., Lindahl U., J. Biol. Chem., 2001 Jun. 8; 276(23): 20069-77.

Non-Patent Document 14: Crawford B. E., Olson S. K., Esko J. D., Pinhal M. A., J. Biol. Chem., 2001 Jun. 15; 276(24): 21538-43.

Non-Patent Document 15: Gesteira T. F., Coulson-Thomas V. J., Ogata F. T., Farias E. H., Cavalheiro R. P., de Lima M. A., Cunha G. L, Nakayasu E. S., Almeida I. C., Toma L., Nader H. B., Biochim. Biophys. Acta., 2011 December; 1814(12): 1862-9.

SUMMARY OF THE INVENTION

Problems to be Solved by the Invention

An object of the present invention is to provide a heparosan-glucuronate 5-epimerase (HG-5epi). More specific objects of the present invention include to provide an enzyme derived from *Achatina fulica*, the enzyme having activity of epimerizing GlcA residues of NAH to IdoA residues, and/or activity of epimerizing IdoA residues of CDSNAc-HEP to GlcA residues (hereinafter such activities are collectively referred to as "HG-5epi activity"); a polypeptide having such activities; a nucleic acid encoding the polypeptide; a vector including the nucleic acid; a host cell harboring the nucleic acid and/or the vector; a method for producing the polypeptide; a method for producing a polysaccharide in which HexA has been epimerized, the method employing the enzyme and/or the polypeptide; and others.

Means for Solving the Problems

The present inventors have focused on AS being a GAG which includes GlcNAc and IdoA(2S) as structural components and which includes no GlcNS in the backbone thereof, and have thought that *Achatina fulica* contains a novel epimerase having substrate specificity completely different from that of a known C5-epi involved in biosynthesis of HEP and HS. In other words, the present inventors have conceived that an epimerase acting on NAH as a substrate—HG-5epi—is present in *Achatina fulica*, and the epimerase is involved in biosynthesis of AS.

The present inventors have conducted extensive studies to attain the aforementioned objects, and have found that a novel epimerase—HG-5epi—is present in *Achatina fulica*. The inventors have successfully isolated a DNA encoding HG-5epi from *Achatina fulica*. The present invention has been accomplished on the basis of the above.

Accordingly, the present invention can be exemplified as follows.

[1]

An enzyme derived from *Achatina fulica*, the enzyme having the following characteristics (A) and (B):

(A) the enzyme having activity of epimerizing glucuronic acid residues of N-acetyl heparosan to iduronic acid residues and/or activity of epimerizing iduronic acid residues of completely desulfated N-acetylated heparin to glucuronic acid residues; and (B) the enzyme having substantially no activity of epimerizing glucuronic acid residues of N-sulfated heparosan to iduronic acid residues and/or substantially no activity of epimerizing iduronic acid residues of completely desulfated N-resulfated heparin to glucuronic acid residues.

[2]

A polypeptide selected from the group consisting of the following (A) to (C):

(A) a polypeptide comprising the amino acid sequence (a1) or (a2):

(a1) the amino acid sequence defined by amino acid NOs: 1 to 601 in SEQ ID NO: 2, and (a2) the amino acid sequence defined by amino acid NOs: 34 to 601 in SEQ ID NO: 2;

(B) a polypeptide comprising the amino acid sequence equivalent to that of the polypeptide (A), except that one or a small number of amino acid residues are substituted, deleted, inserted, and/or added, and having activity of epimerizing glucuronic acid residues of N-acetyl heparosan to iduronic acid residues and/or activity of epimerizing iduronic acid residues of completely desulfated N-acetylated heparin to glucuronic acid residues; and (C) a polypeptide comprising the amino acid sequence of a fusion polypeptide formed by adding a peptide tag to the polypeptide (A) or (B), and having activity of epimerizing glucuronic acid residues of N-acetyl heparosan to iduronic acid residues and/or activity of epimerizing iduronic acid residues of completely desulfated N-acetylated heparin to glucuronic acid residues.

[3]

A polypeptide having the following characteristics (A) to (C):

(A) the polypeptide having activity of epimerizing glucuronic acid residues of N-acetyl heparosan to iduronic acid residues and/or activity of epimerizing iduronic acid residues of completely desulfated N-acetylated heparin to glucuronic acid residues;

(B) the polypeptide having an optimum pH of 5.5 to 6.0; and (C) the polypeptide substantially losing the activity in the presence of 0.1% (w/v) or more of sodium deoxycholate.

[4]

A nucleic acid encoding the aforementioned enzyme or any of the aforementioned polypeptides.

[5]

A DNA selected from the group consisting of the following (A) to (C):

(A) a DNA comprising the nucleotide sequence (a1) or (a2):
  (a1) the nucleotide sequence defined by base NOs: 1 to 1,806 in SEQ ID NO: 1, and
  (a2) the nucleotide sequence defined by base NOs: 100 to 1,806 in SEQ ID NO: 1;

(B) a DNA hybridizing with the DNA consisting of the nucleotide sequence complementary to that of the DNA (A) under a stringent condition, and encoding a polypeptide having activity of epimerizing glucuronic acid residues of N-acetyl heparosan to iduronic acid residues and/or activity of epimerizing iduronic acid residues of completely desulfated N-acetylated heparin to glucuronic acid residues; and (C) a DNA comprising the nucleotide sequence of a fusion DNA formed by adding the DNA encoding a peptide tag to the DNA (A) or (B), and encoding a polypeptide having activity of epimerizing glucuronic acid residues of N-acetyl heparosan to iduronic acid residues and/or activity of epimerizing iduronic acid residues of completely desulfated N-acetylated heparin to glucuronic acid residues.

[6]

A vector including the aforementioned nucleic acid and/or the aforementioned DNA.

[7]

A host cell harboring the aforementioned nucleic acid, the aforementioned DNA, and/or the aforementioned vector.

[8]

A method for producing a polypeptide, the method comprising the following (A) and (B):

(A) a step of expressing a polypeptide having activity of epimerizing glucuronic acid residues of N-acetyl heparosan to iduronic acid residues, and/or activity of epimerizing iduronic acid residues of completely desulfated N-acetylated heparin to glucuronic acid residues, by using the host cell; and (B) a step of recovering the polypeptide expressed in the step (A).

[9]

A polypeptide produced through the aforementioned method.

[10]

A method for producing a polysaccharide in which hexuronic acid residues has been epimerized, the method comprising a step of bringing an enzyme and/or a polypeptide having activity of epimerizing glucuronic acid residues of N-acetyl heparosan to iduronic acid residues and/or activity of epimerizing iduronic acid residues of completely desulfated N-acetylated heparin to glucuronic acid residues, into contact with a polysaccharide including a disaccharide formed of an N-acetyl glucosamine residue and a hexuronic acid residue.

[11]

A method for producing a polysaccharide in which hexuronic acid residues has been epimerized, the method comprising a step of bringing the aforementioned enzyme and/or the aforementioned polypeptide into contact with a polysaccharide including a disaccharide formed of an N-acetyl glucosamine residue and a hexuronic acid residue.

[12]

A polysaccharide produced through any of the aforementioned methods.

[13]

A polysaccharide having a structure in which glucuronic acid residues of N-acetyl heparosan has been epimerized to iduronic acid residues.

[14]

Any of the aforementioned polysaccharides, wherein the ratio of the amount of the iduronic acid residues to that of the hexuronic acid residues present in the polysaccharide backbone thereof is 20% to 75%.

BRIEF DESCRIPTION OF THE DRAWINGS

FIG. 1 A photoimage of a CBB-stained gel of a column-purified HG-5epi eluted fraction obtained by SDS-polyacrylamide gel electrophoresis (SDS-PAGE) under reducing conditions.

FIG. 2 A flow diagram showing an HPLC post column labeling method.

FIG. 3 A chromatogram of NAH or CDSNAc-HEP subjected to N-deacetylation and nitrous acid degradation, followed by the HPLC post column labeling method.

FIG. 4 A chromatogram of NAH subjected to contact with roughly purified HG-5epi and then N-deacetylation and nitrous acid degradation, followed by the HPLC post column labeling method.

FIG. 5 A chromatogram of NSH subjected to contact with roughly purified HG-5epi and then nitrous acid degradation, followed by the HPLC post column labeling method.

FIG. 6 A chromatogram of NAH subjected to contact with HG-5epi and then N-deacetylation and nitrous acid degradation, followed by the HPLC post column labeling method.

MODES FOR CARRYING OUT THE INVENTION (1) Enzyme of the Present Invention

The enzyme of the present invention is an enzyme derived from *Achatina fulica*, the enzyme having the following characteristics (A) and (B).

(A) the enzyme having activity of epimerizing GlcA residues of NAH to IdoA residues and/or activity of epimerizing IdoA residues of CDSNAc-HEP to GlcA residues; and (B) the enzyme having substantially no activity of epimerizing GlcA residues of NSH to IdoA residues and/or substantially no activity of epimerizing IdoA residues of CDSNS-HEP to GlcA residues.

As used herein, the expression "derived from *Achatina fulica*" refers to a state that a target is able to be recovered from *Achatina fulica*.

The enzyme of the present invention has HG-5epi activity. As mentioned above, the term "HG-5epi activity" refers to activity of epimerizing GlcA residues of NAH to IdoA residues, and/or activity of epimerizing IdoA residues of completely desulfated N-acetylated heparin (CDSNAc-HEP) to GlcA residues. HG-5epi activity can be determined through, for example, an HPLC post column labeling method as described in the below-mentioned <Example 14>, <Example 16>, or <Example 17>. Alternatively, HG-5epi activity may be determined through a method employing a radioisotope as described in, for example, the below-mentioned <Example 20> or <Example 21>. More specifically, the activity of epimerizing GlcA residues of NAH to IdoA residues may be determined through a method described in the below-mentioned <Example 14>, <Example 16>, <Example 20>, or <Example 21>. Also, specifically, the activity of epimerizing IdoA residues of CDSNAc-HEP to GlcA residues may be determined through a method described in the below-mentioned <Example 17>.

The enzyme of the present invention may have both of, or either one of activity of epimerizing GlcA residues of NAH to IdoA residues and activity of epimerizing IdoA residues of CDSNAc-HEP to GlcA residues. For example, the enzyme of the present invention may have activity of epimerizing GlcA residues of NAH to IdoA residues and substantially no activity of epimerizing IdoA residues of CDSNAc-HEP to GlcA residues.

NAH is a polysaccharide including disaccharides formed of a GlcNAc residue and a GlcA residue. CDSNAc-HEP is a polysaccharide including disaccharides formed of a GlcNAc residue and a GlcA residue, and disaccharides formed of a GlcNAc residue and an IdoA residue. Hereinafter, GlcA and IdoA will be collectively referred to as "HexA." That is, each of NAH and CDSNAc-HEP is a polysaccharide including disaccharides formed of a GlcNAc residue and a HexA residue.

NAH and CDSNAc-HEP are examples of the substrate on which the enzyme of the present invention acts, and no particular limitation is imposed on the substrate on which the enzyme of the present invention acts. That is, so long as the enzyme of the present invention has HG-5epi activity, the enzyme may have activity of epimerizing a HexA residue adjacent to a GlcNAc residue of another polysaccharide including a disaccharide formed of a GlcNAc residue and a HexA residue (i.e., a polysaccharide other than NAH and CDSNAc-HEP). No particular limitation is imposed on the term "another polysaccharide" as used herein, so long as the polysaccharide includes a disaccharide formed of a GlcNAc residue and a HexA residue. The concept "another polysaccharide" more specifically refers to a polysaccharide including a disaccharide formed of a GlcNAc residue and a GlcA residue, and/or a disaccharide formed of a GlcNAc residue and an IdoA residue. The "epimerization of HexA residues" refers to epimerization of GlcA residues to IdoA residues and/or epimerization of IdoA residues to GlcA residues.

As used herein, the "disaccharide formed of a GlcNAc residue and a HexA residue" refers to a disaccharide in which a GlcNAc residue is bonded to a HexA residue. No particular limitation is imposed on the sequential order of the GlcNAc residue and the HexA residue in the "disaccharide formed of a GlcNAc residue and a HexA residue." Specific examples of the "disaccharide formed of a GlcNAc residue and a HexA residue" include disaccharides represented by the structural formulas (2) to (5) given hereinbelow.

In other words, more specifically, the enzyme of the present invention may be, for example, an enzyme having activity of epimerizing a disaccharide (GlcNAcα1-4GlcA) represented by the following structural formula (2) which is formed of a GlcNAc residue and a GlcA residue and which is present in a polysaccharide backbone, to a disaccharide (GlcNAcα1-4IdoA) represented by the following structural formula (3) which is formed of a GlcNAc residue and an IdoA residue, and/or activity of epimerizing the disaccharide represented by the following structural formula (3) which is present in a polysaccharide backbone, to the disaccharide represented by the following structural formula (2).

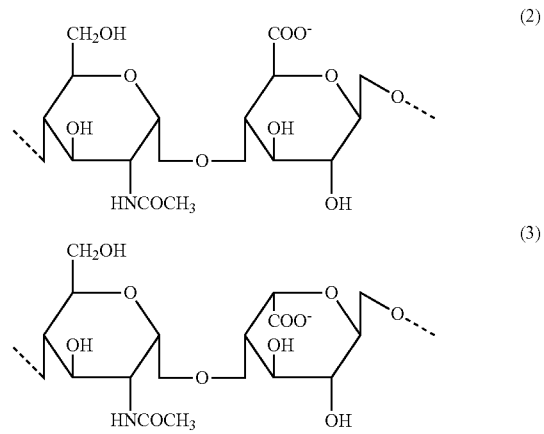

Also, more specifically, the enzyme of the present invention may be, for example, an enzyme having activity of epimerizing a disaccharide (GlcAβ1-4GlcNAc) represented by the following structural formula (4) which is formed of a GlcA residue and a GlcNAc residue and which is present in a polysaccharide backbone, to a disaccharide (IdoAα1-4GlcNAc) represented by the following structural formula (5) which is formed of an IdoA residue and a GlcNAc residue, and/or activity of epimerizing the disaccharide represented by the following structural formula (5) which is present in a polysaccharide backbone, to the disaccharide represented by the following structural formula (4).

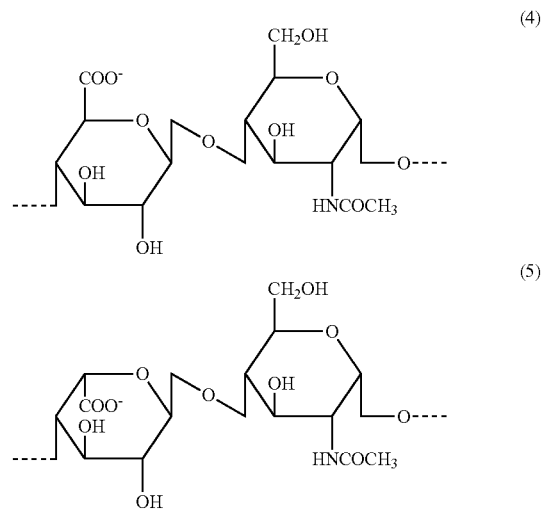

No particular limitation is imposed on the position of the GlcA residue in the polysaccharide (e.g., NAH) epimerized to the IdoA residue by the enzyme of the present invention. In the polysaccharide (e.g., NAH) backbone, such a GlcA residue is present at a reducing end, at a non-reducing end, or at a middle portion of the polysaccharide backbone. In the present invention, the position may be any of the three cases.

No particular limitation is imposed on the position of the IdoA residue in the polysaccharide (e.g., CDSNAc-HEP) epimerized to the GlcA residue by the enzyme of the present invention. In the polysaccharide (e.g., CDSNAc-HEP) backbone, such an IdoA residue is present at a reducing end, at a non-reducing end, or at a middle portion of the polysaccharide backbone. In the present invention, the position may be any of the three cases.

The enzyme of the present invention is an enzyme having substantially no C5-epi activity. As used herein, the term "C5-epi activity" refers to activity of epimerizing GlcA residues of NSH to IdoA residues, and/or activity of epimerizing IdoA residues of completely desulfated N-resulfated heparin (CDSNS-HEP) to GlcA residues. The C5-epi activity may be determined through an HPLC post column labeling method as described in, for example, the below-mentioned <Example 15> or <Example 18>. Specifically, the activity of epimerizing GlcA residues of NSH to IdoA residues may be determined through a method described in the below-mentioned <Example 15>. Also, specifically, the activity of epimerizing IdoA residues of CDSNS-HEP to GlcA residues may be determined through a method described in the below-mentioned <Example 18>.

The expression "having substantially no activity" means that no change (increase or decrease) in IdoA content or substantially no change (increase or decrease) in IdoA content is observed before and after bringing a polysaccharide corresponding to the activity into contact with an enzyme. Specifically, for example, the expression "having substantially no C5-epi activity" means that no change (increase or decrease) in IdoA content or substantially no change (increase or decrease) in IdoA content is observed before and after bringing NSH into contact with an enzyme, and/or that no change (increase or decrease) in IdoA content or substantially no change (increase or decrease) in IdoA content is observed before and after bringing CDSNS-HEP into contact with an enzyme.

As used herein, the "IdoA content" refers to a ratio of the amount of IdoA residues to that of HexA residues present in a polysaccharide backbone; i.e., the percentage equivalent derived by dividing the total number of IdoA residues by that of HexA residues (the sum of the total number of GlcA residues and that of IdoA residues). The IdoA content may be determined through a method as described in, for example, the below-mentioned <Example 14>, <Example 15>, <Example 16>, <Example 17>, or <Example 18>. Thus, the state that "substantially no change in IdoA content is observed" may refer to the case where upon determining and comparing IdoA contents through an HPLC post column labeling method before and after bringing a polysaccharide into contact with the enzyme of the present invention, a change only within an error range is observed in IdoA content. Specifically, the state that "substantially no change in IdoA content is observed" may refer to the case where the amount of the change is 5% or less, 2% or less, 1% or less, or 0.5% or less, i.e., when the IdoA content before enzymatic reaction is n (%), the IdoA content after the enzymatic reaction is n−5(%) to n+5(%), n−2(%) to n+2(%), n−1(%) to n+1(%), or n−0.5(%) to n+0.5(%).

Whether or not a protein has HG-5epi activity can be determined through a method as described in the below-mentioned <Example 14>, <Example 16>, <Example 17>, <Example 20>, or <Example 21>. Also, whether or not a protein has substantially no C5-epi activity can be determined through a method as described in the below-mentioned <Example 15> or <Example 18>. Thus, these methods may determine whether or not any protein derived from *Achatina fulica* is the enzyme of the present invention.

The enzyme of the present invention may be recovered from *Achatina fulica*. In one specific procedure, for example, the enzyme of the present invention is recovered from a cell disrupted product obtained by crushing *Achatina fulica* cells or a cell extract obtained from *Achatina fulica* cells. The "crushing (disruption or disintegration)" may be carried out through a technique appropriately selected in accordance with the cell species. Examples of the crushing technique include homogenizing, ultrasonication, freezing and thawing, and addition of a surfactant. These techniques may be appropriately employed in combination. No particular limitation is imposed on the cells from which the enzyme of the present invention is to be recovered, so long as the enzyme of the present invention is expressed in the cells. Examples of such cells include mucous gland cells.

The enzyme of the present invention may be recovered through a known technique as employed in isolation and purification of protein. Examples of such techniques include precipitation with ammonium sulfate, gel filtration chromatography, ion exchange chromatography, hydrophobic interaction chromatography, hydroxyapatite chromatography, and affinity chromatography. These techniques may be appropriately employed in combination.

The enzyme of the present invention may consist of the enzyme of the present invention as a single component or may contain an additional component other than the enzyme of the present invention. Examples of the "additional component other than the enzyme of the present invention" include alkali metal salts, surfactants, buffers, and components derived from *Achatina fulica*. No particular limitation is imposed on the form of the enzyme of the present invention, and it may be liquid or solid. In the case where the enzyme of the present invention is provided as a liquid, the liquid may be in the frozen state or the liquid state (thawed state). When the enzyme of the present invention is provided as a solid, the solid may be a lyophilized product, an immobilized enzyme (e.g., an enzyme-immobilized material in which the enzyme is immobilized on agarose beads and the like), etc.

Regarding the product of the enzyme of the present invention, the weight concentration of the enzyme of the present invention may be appropriately predetermined. Regarding the product of the enzyme of the present invention, the weight concentration of the enzyme of the present invention may be, for example, 0.001% or more, 0.01% or more, 0.1% or more, 1% or more, 5% or more, 10% or more, 25% or more, or 50% or more. Also, regarding the product of the enzyme of the present invention, the weight concentration of the enzyme of the present invention may be, for example, 100% or less, 75% or less, 50% or less, 25% or less, 10% or less, 5% or less, or 1% or less.

(2) Polypeptide of the Present Invention

The polypeptide of the present invention is a polypeptide having HG-5epi activity. So long as the polypeptide of the present invention has HG-5epi activity, no particular limitation is imposed on the type of polypeptide.

An embodiment of the polypeptide of the present invention may be an embodiment of the enzyme of the present invention.

The polypeptide of the present invention may be, for example, a polypeptide comprising a specific amino acid sequence and having HG-5epi activity.

Specifically, the polypeptide of the present invention may be, for example, a polypeptide selected from the group consisting of the following (A) to (C):

(A) A polypeptide comprising an amino acid sequence (a1) or (a2):

(a1) the amino acid sequence defined by amino acid NOs: 1 to 601 in SEQ ID NO: 2, and (a2) the amino acid sequence defined by amino acid NOs: 34 to 601 in SEQ ID NO: 2;

(B) a polypeptide comprising the amino acid sequence equivalent to that of polypeptide (A), except that one or a small number of amino acid residues are substituted, deleted, inserted, and/or added, and having HG-5epi activity; and (C) a polypeptide comprising the amino acid sequence of a fusion polypeptide formed by adding a peptide tag to the polypeptide (A) or (B), and having HG-5epi activity.

In other words, the polypeptide of the present invention provides the following three embodiments. A first embodiment is a polypeptide comprising the amino acid sequence defined by amino acid NOs: 1 to 601 or 34 to 601 in SEQ ID NO: 2. A second embodiment is a polypeptide comprising the amino acid sequence equivalent to that of the polypeptide of the first embodiment, except that one or a small number of amino acid residues are substituted, deleted, inserted, and/or added, and having HG-5epi activity. A third embodiment is a polypeptide comprising the amino acid sequence of a fusion polypeptide formed by adding a peptide tag to the polypeptide of the first or second embodiment, and having HG-5epi activity.

As used herein, the expression "comprising the amino acid sequence" also encompasses the case of "consisting of the amino acid sequence."

In the second embodiment, "a small number" refers to the number of amino acid residues that ensures HG-5epi activity, even when that number of amino acid residues are substituted, deleted, inserted, and/or added. For example, the number with respect to all the amino acid residues forming the polypeptide is preferably 10% or less, more preferably 5% or less, still more preferably 2% or less, particularly preferably 1% or less.

More specifically, in the case of the polypeptide consisting of an amino acid sequence defined by amino acid NOs: 1 to 601 in SEQ ID NO: 2, the total number of the amino acid residues is 601. Thus, "a small number" is preferably 2 to 60, more preferably 2 to 30, still more preferably 2 to 12, particularly preferably 2 to 6. In the case of the polypeptide consisting of an amino acid sequence defined by amino acid NOs: 34 to 601 in SEQ ID NO: 2, the total number of the amino acid residues is 568. Thus, "a small number" is preferably 2 to 56, more preferably 2 to 28, still more preferably 2 to 11, particularly preferably 2 to 5. In these polypeptides, "a small number" may be 2, 2 or 3, 2 to 4, or 2 to 5.

The "substitution, deletion, insertion, and/or addition" of the second embodiment is, for example, a conservative variation where HG-5epi activity is not lost. A typical conservative variation is conservative substitution. Conservative substitution is a variation among Phe, Trp, and Tyr, in the case where the substitution occurs at an aromatic amino acid residue; a variation among Leu, Ile, and Val, in the case where the substitution occurs at a hydrophobic amino acid residue; a variation between Gln and Asn, in the case where the substitution occurs at a polar amino acid residue; a variation among Lys, Arg, and His, in the case where the substitution occurs at a basic amino acid residue; a variation between Asp and Glu, in the case where the substitution occurs at an acidic amino acid residue; or a variation between Ser and Thr, in the case where the substitution occurs at an amino acid residue having a hydroxyl group. Specific examples of the substitution which can be recognized as conservative substitution include a substitution of Ala by Ser or Thr; a substitution of Arg by Gln, His, or Lys; a substitution of Asn by Glu, Gln, Lys, His, or Asp; a substitution of Asp by Asn, Glu, or Gln; a substitution of Cys by Ser or Ala; a substitution of Gln by Asn, Glu, Lys, His, Asp, or Arg; a substitution of Glu by Gly, Asn, Gln, Lys, or Asp; a substitution of Gly by Pro; a substitution of His by Asn, Lys, Gln, Arg, or Tyr; a substitution of Ile by Leu, Met, Val, or Phe; a substitution of Leu by Ile, Met, Val, or Phe; a substitution of Lys by Asn, Glu, Gln, His, or Arg; a substitution of Met by Ile, Leu, Val, or Phe; a substitution of Phe by Trp, Tyr, Met, Ile, or Leu; a substitution of Ser by Thr or Ala; a substitution of Thr by Ser or Ala; a substitution of Trp by Phe or Tyr; a substitution of Tyr by His, Phe, or Trp; and a substitution of Val by Met, Ile, or Leu.

In other words, for example, the polypeptide of the second embodiment may be a polypeptide which has a homology of 90% or higher with respect to the entire amino acid sequence of the polypeptide of the first embodiment, more preferably 95% or higher, still more preferably 98% or higher, particularly preferably 99% or higher, and which has HG-5epi activity. In the present invention, "homology" may also refer to "identity."

The "peptide tag" described in the third embodiment refers to a peptide consisting of an amino acid sequence for facilitating detection or purification of protein. No particular limitation is imposed on the length and amino acid sequence of the "peptide tag," so long as the fusion polypeptide formed by adding the peptide tag to the polypeptide of the first or second embodiment does not lose HG-5epi activity. Examples of the peptide tag include FLAG (registered trademark) peptide (FLAG tag), 6×His peptide (His.Tag (registered trademark)), c-myc peptide (myc tag), protein A, MBP (maltose-binding protein), and GST (glutathione-S-transferase). Of these, FLAG peptide (SEQ ID NO: 32) is preferred.

The "peptide tag" may be directly added to the polypeptide of the first or second embodiment, or added thereto via a peptide linker consisting of any amino acid sequence. Similar to the case of peptide tag, no particular limitation is imposed on the length and amino acid sequence of the "peptide linker," so long as the fusion polypeptide formed by adding the peptide tag to the polypeptide of the first or second embodiment does not lose HG-5epi activity. Examples of the peptide linker include the dipeptide formed of N-terminal asparagine and C-terminal serine, and the dipeptide formed of N-terminal valine and C-terminal aspartic acid.

Also, the "peptide tag" may be added to either the N-terminus or the C-terminus of the polypeptide of the first or second embodiment, or to both terminuses. Preferably, the "peptide tag" is added to only the N-terminus of the polypeptide.

The polypeptide of the present invention is a polypeptide having HG-5epi activity. Whether or not the polypeptide has HG-5epi activity can be determined through a method as described in, for example, the below-mentioned <Example 14>, <Example 16>, <Example 17>, <Example 20>, or <Example 21>. Through employment of any of these methods, the polypeptide of the second or third embodiment can be selected. Namely, the polypeptide of the second embodiment may be obtained by, for example, selecting parts of the amino acid residues into which substitution, deletion, insertion, and/or addition of one or a small number of amino acid residues can be introduced without losing HG-5epi activity from the amino acid sequence of the polypeptide of the first embodiment, based on the presence or absence of HG-5epi activity as an index. Also, the polypeptide of the third embodiment may be obtained by, for example, selecting an amino acid sequence to which a peptide tag can be added without losing HG-5epi activity from the amino acid sequence of the polypeptide of the first or second embodiment, based on the presence or absence of HG-5epi activity as an index.

So long as the polypeptide of the present invention has HG-5epi activity, the polypeptide may have an additional activity of epimerizing a HexA residue adjacent to a GlcNAc residue of another polysaccharide (i.e. polysaccharide other than NAH or CDSNAc-HEP) including a disaccharide formed of a GlcNAc residue and a HexA residue.

The polypeptide of the present invention may have C5-epi activity or may have substantially no C5-epi activity. The presence or absence of C5-epi activity may be determined through a method as described in, for example, the below-mentioned <Example 15> or <Example 18>.

The polypeptide of the present invention may have an optimum pH of 5.5 to 6.0 for HG-5epi activity. The optimum pH may be determined through a method as described in, for example, the below-mentioned <Example 22>.

The polypeptide of the present invention may substantially lose HG-5epi activity in the presence of 0.1% (w/v) or more of sodium deoxycholate.

The polypeptide of the present invention may have a feature that HG-5epi activity decreases depending on alkali metal chloride concentration and/or alkaline earth metal chloride concentration (that is, HG-5epi activity decreases as alkali metal chloride concentration and/or alkaline earth metal chloride concentration increases). Examples of "alkali metal chloride" include sodium chloride. Examples of "alkaline earth metal chloride" include magnesium chloride, calcium chloride, and manganese chloride. This feature may be significant in the case of alkaline earth metal chlorides, especially calcium chloride among them. Also, this feature may be, for example, a feature that HG-5epi activity is substantially lost in the presence of 64 mM or more of calcium chloride.

As used herein, the expression "HG-5epi activity is substantially lost" may refer to, for example, the HG-5epi activity in the presence of a target substance (e.g., sodium deoxycholate, alkali metal chloride, or alkaline earth metal chloride) being 10% or less, 5% or less, 2% or less, or 1% or less of the HG-5epi activity in the absence of the target substance.

Whether or not HG-5epi activity has been substantially lost may be determined through, for example, a method employing a radioisotope as described in the below-mentioned <Example 23> or <Example 24>. In this case, the expression "HG-5epi activity is substantially lost" may refer to, for example, the following feature. Specifically, a polypeptide is brought into contact with a target polysaccharide (e.g., [5-$^3$H]NAH) in which the hydrogen atom at 5-position of HexA residues has been substituted by $^3$H (tritium) in the presence of a target substance (e.g., sodium deoxycholate, alkali metal chloride, or alkaline earth metal chloride). The target polysaccharide (e.g., [5-$^3$H]NAH) is removed from each of the reaction mixtures before and after the contact process, and each resultant solution is fed to a scintillation counter. The radioactivity of $^3$H$_2$O of each solution, formed during the course of epimerization of HexA residues of the target polysaccharide (e.g., [5-$^3$H]NAH) by HG-5epi activity, is measured. In comparison of the two solutions, there is no significant difference between two measurements (dpm). For example, the expression "HG-5epi activity is substantially lost" may refer to the measurement of the solution obtained from the reaction mixture after the contact process being 3 times or less that of the solution obtained from the reaction mixture before the contact process. Notably, [5-$^3$H]NAH may be prepared through, for example, a method as described in the below-mentioned <Example 19>.

So long as the polypeptide of the present invention has HG-5epi activity, the polypeptide is not limited to a polypeptide having a specific amino acid sequence as described in any of the first to third embodiments. The polypeptide of the present invention, for example, may be a polypeptide having HG-5epi activity and one or more features as described above.

The polypeptide of the present invention may have the following characteristics (A) to (C):

(A) the polypeptide having HG-5epi activity;

(B) the polypeptide having an optimum pH of 5.5 to 6.0; and (C) the polypeptide substantially losing HG-5epi activity in the presence of 0.1% (w/v) or more of sodium deoxycholate.

Such a polypeptide may further have one or more features as described above. That is, such a polypeptide may, for example, have an additional activity of epimerizing a HexA residue adjacent to a GlcNAc residue of another polysaccharide (i.e. polysaccharide other than NAH or CDSNAc-HEP) including a disaccharide formed of a GlcNAc residue and a HexA residue. Also, such a polypeptide may have, for example, C5-epi activity or may have substantially no C5-epi activity. Furthermore, such a polypeptide may have, for example, a feature that the activity decreases depending on the alkali metal chloride concentration and/or the alkaline earth metal chloride concentration.

The polypeptide of the present invention may be prepared through, for example, a genetic technique by use of the below-mentioned host cell of the present invention. Examples of the "genetic technique" include a method employing insect cells as described in the below-mentioned <Example 6> to <Example 13>.

(3) Nucleic Acid of the Present Invention

The nucleic acid of the present invention is a nucleic acid encoding the enzyme of the present invention or the polypeptide of the present invention. As described above, an embodiment of the polypeptide of the present invention may be an embodiment of the enzyme of the present invention. Thus, an embodiment of the nucleic acid of the present invention may be a nucleic acid encoding the enzyme of the present invention. No particular limitation is imposed on the nucleic acid of the present invention, so long as the nucleic acid encodes the polypeptide of the present invention. So long as the nucleic acid of the present invention encodes the polypeptide of the present invention, the nucleic acid encompasses all the nucleic acids consisting of different nucleotide sequences resulting from genetic code degeneration.

The "nucleic acid" encompasses DNA and RNA. Also, the nucleic acid of the present invention may be a double strand nucleic acid or a single strand nucleic acid. In the case of the double strand, a hybrid nucleic acid formed of DNA and RNA is acceptable. So long as the nucleic acid of the present invention encodes the polypeptide of the present invention, the nucleic acid may be a nucleic acid which includes intron sequences in a domain encoding the polypeptide of the present invention, or a nucleic acid which includes no intron sequence in a domain encoding the polypeptide of the present invention. Examples of the nucleic acid of the present invention include mRNA (mRNA precursor or mature mRNA) derived from *Achatina fulica*, and cDNA synthesized through reverse transcription of mRNA. The nucleic acid of the present invention may be an isolated nucleic acid.

The nucleic acid of the present invention may be, for example, a nucleic acid which comprises a specific nucleotide sequence and which encodes a polypeptide having HG-5epi activity.

Specifically, the nucleic acid of the present invention may be, for example, a DNA selected from the group consisting of the following (A) to (C):

(A) a DNA comprising the nucleotide sequence (a1) or (a2):
(a1) the nucleotide sequence defined by base NOs: 1 to 1,806 in SEQ ID NO: 1, and
(a2) the nucleotide sequence defined by base NOs: 100 to 1,806 in SEQ ID NO: 1;

(B) a DNA hybridizing with the DNA consisting of the nucleotide sequence complementary to that of the DNA (A) under a stringent condition, and encoding a polypeptide having HG-5epi activity; and (C) a DNA comprising the nucleotide sequence of a fusion DNA formed by adding the DNA encoding a peptide tag to the DNA (A) or (B), and encoding a polypeptide having HG-5epi activity.

In other words, the nucleic acid of the present invention provides the following three embodiments. A first embodiment is a DNA comprising the nucleotide sequence defined by base NOs: 1 to 1,806 or 100 to 1,806 in SEQ ID NO: 1. A second embodiment is a DNA hybridizing with the DNA consisting of the nucleotide sequence complementary to that of the DNA of the first embodiment under a stringent condition, and encoding a polypeptide having HG-5epi activity. A third embodiment is a DNA comprising the nucleotide sequence of a fusion DNA formed by adding the DNA encoding a peptide tag to the DNA of the first or second embodiment, and encoding a polypeptide having HG-5epi activity. Such DNAs may be isolated DNAs.

As used herein, the expression "comprising the nucleotide sequence" also encompasses the case of "consisting of the nucleotide sequence."

The DNA of the first embodiment may be produced through, for example, a method as described in the below-mentioned <Example 1> to <Example 5>. Alternatively, the DNA of the first embodiment may be produced through a polymerase chain reaction (PCR) employing designed oligonucleotides based on the nucleotide sequence defined by SEQ ID NO: 1 as primers, in which DNA fragments are amplified by use of a nucleic acid (chromosomal DNA or cDNA) derived from *Achatina fulica* as a template.

In the second embodiment, the term "stringent conditions" generally refers to the conditions under which a specific hybrid is formed but a non-specific hybrid is not formed. In other words, the term "stringent conditions" refers to conditions under which a specific hybrid with a DNA having a nucleotide sequence complementary to that of the DNA of the first embodiment is formed. An example of such conditions is conditions under which DNA fragments having a high homology (e.g., a homology of 80% or higher, preferably 90% or higher, more preferably 95% or higher, still more preferably 97% or higher, particularly preferably 99% or higher) are hybridized with each other, and DNA fragments having a homology lower than the level are not hybridized with each other. Examples of such conditions include conditions generally employed in washing of southern hybridization; i.e., conditions of washing once, desirably 2 or 3 times, at a salt concentration and temperature corresponding to 60° C., 1×SSC, 0.1% SDS, desirably 60° C., 0.1×SSC, 0.1% SDS, more desirably 68° C., 0.1×SSC, 0.1% SDS. Examples of such conditions further include conditions including hybridization at 42° C. in a solution formed of 50% formamide, 4×SSC, 50 mM HEPES-NaOH (pH: 7.0), 10×Denhardt's solution, and 100 µg/mL salmon sperm DNA; washing at room temperature with a solution formed of 2×SSC and 0.1% SDS; and further washing at 50° C. with a solution formed of 0.1×SSC and 0.1% SDS (Sambrook J., et al., Molecular Cloning: A Laboratory Manual, Second Edition, Cold Spring Harbor Laboratory Press (1989)).

The DNA of the second embodiment may be prepared, for example, by introducing, into the nucleotide sequence of the DNA of the first embodiment, substitution, deletion, insertion, and/or addition of nucleic acid residues (hereinafter collectively referred to as "introduction of variation"). The "introduction of variation" may be performed through, for example, a known technique.

The "introduction of variation" may be carried out through, for example, a technique employing restriction enzymes and a T4DNA ligase. More specifically, the technique includes limitedly digesting by restriction enzymes both terminuses of a DNA fragment having a nucleotide sequence into which a variation has been introduced so as to encode a polypeptide consisting of an objective amino acid sequence; mixing the digested product with a vector into which the nucleotide sequence consisting of SEQ ID NO: 1 has been subcloned, and which has been limitedly digested with the same restriction enzymes; and ligating the two components by use of a T4DNA ligase, to thereby yield a DNA into which the variation has been introduced. The "DNA fragment having a nucleotide sequence into which a variation has been introduced" may be obtained through, for example, a PCR employing as a primer an oligonucleotide into which such a variation has been introduced. Alternatively, the above DNA fragment may also be obtained by mixing, in an aqueous solution, two complementary oligonucleotides which have been synthesized to have sequences into which a variation has been introduced at specific bases; heating the mixture at 90 to 100° C. for 1 to 2 minutes; and cooling the mixture to room temperature.

An alternative example of a method for "introduction of variation" is a site-specific variation introduction method. Examples of the site-specific variation introduction method include a PCR-based method (Higuchi, R., 61, in PCR technology, Erlich, H. A. Eds., Stockton press (1989); Carter, P., *Meth. in Enzymol.*, 154, 382 (1987)), and a method employing a phage (Kramer, W. and Frits, H. J., *Meth. in Enzymol.*, 154, 350 (1987); Kunkel, T. A. et al., *Meth. in Enzymol.*, 154, 367 (1987)). Specifically, for example, the site-specific variation introduction method may be carried out by means of KOD-Plus-Mutagenesis Kit (Product of Toyobo).

The "peptide tag" of the third embodiment is the same as the peptide tag which is described in detail in the above-mentioned "(2) polypeptide of the present invention." Thus, so long as the encoded polypeptide has HG-5epi activity, a fusion DNA to which a DNA encoding the peptide tag has been added also falls within the scope of the nucleic acid of the present invention. The "DNA encoding the peptide tag" may be a DNA encoding only a peptide tag or a fusion DNA consisting of a DNA encoding a peptide tag and another DNA encoding a linker sequence.

Alternatively, the nucleic acid of the present invention may also be yielded through total chemical synthesis of the nucleotide sequence thereof.

The polypeptide encoded by the nucleic acid of the present invention has HG-5epi activity. The polypeptide encoded by the nucleic acid of the present invention may be prepared by the method described in the above-mentioned "(2) Polypeptide of the present invention." The presence or absence of HG-5epi activity of the polypeptide encoded by the nucleic acid of the present invention may be determined through the method described in the above-mentioned "(2) Polypeptide of the present invention."

(4) Vector of the Present Invention

The vector of the present invention is a vector including the nucleic acid of the present invention. The vector of the present invention may include one type of the nucleic acid of the present invention or two or more members of the nucleic acid of the present invention. The vector of the present invention may include one copy of the nucleic acid of the present invention or two or more copies thereof.

As used herein, the term "vector" refers to a nucleic acid molecule employed for incorporating the nucleic acid of the present invention into a host cell. No particular limitation is imposed on the vector, so long as there can be attained amplification of the nucleic acid of the present invention or expression of the polypeptide encoded by the nucleic acid of the present invention, in the host cell. Examples of the vector include a phage, a plasmid, and a virus. The vector may be appropriately chosen in accordance with factors such as the type of host cells, and the desired expression level of the polypeptide encoded by the nucleic acid of the present invention. For example, when a prokaryotic cell such as a bacterium cell is used as a host cell, a phage or a plasmid can be suitably used as a vector. Also, for example, when a eukaryotic cell such as an insect cell is used as a host cell, a plasmid or a virus can be suitably used as a vector.

Examples of the phage which can be employed in bacterium cells include phage particles in which a plasmid serving as a phage DNA is packaged. Examples of the plasmid which can be employed in bacterium cells include pBlue Script II SK(+). Examples of the plasmid which can be employed in insect cells or the like include pIZ-V5 (product of Life Technologies Corporation).

Examples of the virus employable in insect cells or the like include Baculovirus. Baculovirus is preferably nuclear polyhedrosis virus (NPV). Examples of NPV include *Autographa californica* NPV (AcNPV) and *Bombyx mori* NPV (BmNPV). Of these, AcNPV is preferred. Through infecting, in a routine manner, a host cell (e.g., an insect cell) with a virus into which the nucleic acid of the present invention has been incorporated, the resultant host cell can harbor the nucleic acid of the present invention and allows expression of the polypeptide encoded by the nucleic acid of the present invention.

The nucleic acid of the present invention may be incorporated into a phage through a conventional technique. An example of the method for incorporating the nucleic acid of the present invention into a phage is a technique described in the below-mentioned <Example 2>. In one specific manner, for example, a phage DNA including the nucleic acid of the present invention is packaged in phage particles. More specifically, for example, any two of the restriction enzyme sites present in the multi-cloning site of a plasmid serving as a phage DNA are selected, and the plasmid and the nucleic acid of the present invention are limitedly digested with the restriction enzymes, followed by ligation. An example of the plasmid is Lambda ZAP II. The nucleic acid of the present invention may be a DNA prepared through PCR employing oligonucleotides in each of which a restriction enzyme site has been added to the 5' end, as primers. Alternatively, such a restriction enzyme site may be incorporated into the nucleic acid of the present invention through ligation of a DNA fragment having a structure generated by limited digestion with a restriction enzyme at the 5' end, to the nucleic acid of the present invention serving as another DNA fragment.

The nucleic acid of the present invention may be incorporated into a plasmid through a conventional technique. An example of the method for incorporating the nucleic acid of the present invention into a plasmid is a technique described in the below-mentioned <Example 6> or <Example 10>. In one specific manner, for example, any two of the restriction enzyme sites present in the multi-cloning site of a plasmid are selected, and the plasmid and the nucleic acid of the present invention are limitedly digested with the restriction enzymes, followed by ligation. The nucleic acid of the present invention may be a DNA prepared through PCR employing oligonucleotides in each of which a restriction enzyme site has been added to the 5' end, as primers. Alternatively, such a restriction enzyme site may be incorporated into the nucleic acid of the present invention through ligation of a DNA fragment having a structure generated by limited digestion with a restriction enzyme at the 5' end, to the nucleic acid of the present invention serving as another DNA fragment.

The nucleic acid of the present invention may be incorporated into a virus through a conventional technique. For example, incorporation of the nucleic acid of the present invention to a virus may be carried out by preparing a bacmid. More specifically, for example, a bacterium for preparing a bacmid is transformed by use of a donor plasmid into which the nucleic acid of the present invention has been incorporated, to thereby prepare a bacmid into which the nucleic acid of the present invention has been incorporated. Examples of the bacterium for preparing a bacmid include *E. coli* DH10Bac strain. Examples of the donor plasmid include pFastBac1. When a host cell (e.g., an insect cell) is transfected with the thus-prepared bacmid, the bacmid functions as a virus as it is.

Alternatively, for example, the nucleic acid of the present invention may be incorporated into a virus by use of a plasmid called a transfer vector. In one specific manner, for example, a host cell (e.g., an insect cell) is co-transfected with a viral genome and a transfer vector into which the nucleic acid of the present invention has been incorporated, to thereby prepare a virus into which the nucleic acid of the present invention has been incorporated. Examples of the transfer vector include pPSC8 (product of Protein Science) and pVL1393 (product of AB vector).

(5) Host Cell of the Present Invention

The host cell of the present invention is a host cell harboring the nucleic acid of the present invention and/or the vector of the present invention (hereinafter the nucleic acid and the vector are collectively referred to as "the vector or the like of the present invention"). Notably, since the vector of the present invention includes the nucleic acid of the present invention, a host cell harboring the vector of the present invention also falls within a host cell harboring the nucleic acid of the present invention. The host cell of the present invention may harbor one species of the vector or the like of the present invention or two or more species of the vector or the like of the present invention. The host cell of the present invention may harbor one copy of the vector or the like of the present invention or two or more copies of the vector or the like of the present invention. The host cell of the present invention may harbor the vector or the like of the present invention on the chromosome thereof or outside the chromosome thereof. Needless to say, the host cell of the present invention may harbor the vector or the like of the present invention on the chromosome thereof and outside the chromosome thereof. The host cell of the present invention may be a host cell transfected by use of the vector or the like of the present invention. As used herein, the term "host cell" refers to a cell for use as a host in amplification of the vector or the like of the present invention or in expression of a polypeptide encoded by the vector or the like of the present invention. No particular limitation is imposed on the host cell, so long as the host cell can be transfected by the vector or the like of the present invention. The host cell is preferably an isolated cell. The host cell may be appropriately selected in accordance with the purpose of the use of the vector or the like of the present invention.

In order to amplify the vector or the like of the present invention, the host cell is, for example, preferably a prokaryotic cell; e.g., a bacterium cell. Among such bacterium cells, *Escherichia coli* is preferred. Examples of the *Escherichia coli* strain include XL-1 Blue MRF' strain, JM109 strain, and DH5α strain.

In the expression of a polypeptide encoded by the vector or the like of the present invention, the host cell may be, for example, a host cell generally employed in heterologous expression of a protein. The host cell is, for example, preferably a eukaryotic cell; e.g., an insect cell, an animal cell, a plant cell, or a yeast cell. Of these, an insect cell is preferred. Examples of the insect cell include Sf9 cell, Sf21 cell, and SF+ cell, each derived from *Spodoptera frugiperda*, and High Five cell, derived from *Trichoplusia ni*. The insect cell is preferably a cell derived from *Spodoptera frugiperda*. Among them, Sf21 cell is preferred.

Transfection of the host cell may be carried out through a conventional technique. No particular limitation is imposed on the method for transfecting the host cell, so long as the vector or the like of the present invention can be incorporated into the host cell. Specific examples of the host cell transfection method include the calcium phosphate method, lipofection method, the DEAE dextran method, electroporation method, and micro-injection method. Of these, lipofection method is preferred. Lipofection method is preferably performed by use of Cellfectin II Reagent.

(6) Polypeptide Production Method of the Present Invention

The polypeptide of the present invention can be produced by use of, for example, the host cell of the present invention. Specifically, the polypeptide of the present invention can be produced through, for example, the method for producing a polypeptide, the method comprising the following (A) and (B) (hereinafter the production method may be referred to as "the polypeptide production method of the present invention"):

(A) a step of expressing a polypeptide having HG-5epi activity by using the host cell; and (B) a step of recovering the polypeptide expressed in the step (A).

In step (A), the host cell of the present invention is cultured, and a polypeptide which has HG-5epi activity (i.e., the polypeptide of the present invention) and which is encoded by the vector or the like of the present invention is expressed.

A specific example of step (A) may include culturing Sf21 cells obtained by the following procedures: transforming *E. coli* DH10Bac cells with pFastBac1 into which the nucleic acid of the present invention has been incorporated; extracting a bacmid from the transformant; and transfecting Sf21 cell with the bacmid by lipofection method.

No particular limitation is imposed on the culture conditions under which the host cell is cultured, so long as the polypeptide of the present invention encoded by the vector or the like of the present invention can be expressed. The culture conditions may be appropriately selected in accordance with the type of the host cell, the desired expression level of the polypeptide of the present invention encoded by the vector or the like of the present invention, etc. For example, in the case of culturing an insect cell, a culture medium generally employed in insect cells may be used. Examples of the culture medium include a commercial serum-free medium for insect cell culture; specifically, Sf900III serum-free medium. In one mode, for example, culture may be performed at 27° C. to 28° C. with shaking.

In step (B), the polypeptide of the present invention expressed by the host cell in step (A) is recovered. As used herein, the term "recovery" or "recovering" refers to obtaining a fraction containing the polypeptide of the present invention from the culture broth of the host cell. More specifically, in the case where the polypeptide of the present invention is secreted to the outside of the cells, the culture broth itself may be recovered as the polypeptide of the present invention. Alternatively, the supernatant after centrifugation of the culture broth may be recovered as the polypeptide of the present invention. Yet alternatively, the fraction obtained by purifying the culture broth through column or the like may also be recovered as the polypeptide of the present invention.

In the case where the expressed polypeptide of the present invention is accumulated inside the cells, an extract obtained by disrupting the cells may be recovered as the polypeptide of the present invention, or a fraction obtained by purifying the extract by means of a column or the like may also be recovered as the polypeptide of the present invention. In the case where the expressed polypeptide of the present invention is accumulated in the cell membrane, the cells themselves may be recovered as the polypeptide of the present invention, or a disrupted product of the cells may be recovered as the polypeptide of the present invention. The "disruption" may be performed through an appropriate technique in accordance with the type of host cells. Examples of the disruption technique include homogenization method, ultrasonication method, freezing and thawing method, and surfactant-addition method. These techniques may be appropriately employed in combination.

Purification may be performed through a known technique as employed in isolation and purification of protein. Examples of such techniques include precipitation with ammonium sulfate, gel filtration chromatography, ion exchange chromatography, hydrophobic interaction chromatography, hydroxyapatite chromatography, and affinity chromatography. Particularly when a peptide tag has been added to the polypeptide of the present invention, the polypeptide may be purified through affinity chromatography based on the affinity with respect to the tag. These techniques may be appropriately employed in combination.

The purification may be performed to a desired extent. The weight concentration of the polypeptide of the present invention in the recovered fraction may be, for example, 0.001% or higher, 0.01% or higher, 0.1% or higher, 1% or higher, 5% or higher, 10% or higher, 25% or higher, or 50% or higher. Also, the weight concentration of the polypeptide of the present invention in the recovered fraction may be, for example, 100% or lower, 75% or lower, 50% or lower, 25% or lower, 10% or lower, 5% or lower, or 1% or lower.

Whether or not the thus-recovered fraction contains the polypeptide of the present invention may be determined through the method as described in the aforementioned "(2) Polypeptide of the present invention." That is, the presence or absence of HG-5epi activity is checked. Alternatively, whether or not the thus-recovered fraction contains the polypeptide of the present invention may be determined through western blotting employing an antibody which can bind to the polypeptide of the present invention. Western blotting may be performed through a method as described in the below-mentioned <Example 9>.

(7) Polysaccharide Production Method of the Present Invention

The polysaccharide production method of the present invention is a method for producing a polysaccharide, in which HexA residues has been epimerized, comprising a step of bringing an enzyme and/or a polypeptide each having HG-5epi activity (hereinafter collectively referred to as "HG-5epi of the present invention") into contact with a polysaccharide including a disaccharide formed of a GlcNAc residue and a HexA residue. The HG-5epi of the present invention may have C5-epi activity or may have substantially no C5-epi activity. As the HG-5epi of the present invention, one species of enzyme having HG-5epi activity may be used, or two or more species of enzymes each having HG-5epi activity may be used. As the HG-5epi of the present invention, one species of polypeptide having HG-5epi activity may be used, or two or more species of polypeptides each having HG-5epi activity may be used. As the HG-5epi of the present invention, one or more species of enzymes each having HG-5epi activity and one or more species of polypeptides each having HG-5epi activity may be used in combination. Examples of the "enzyme having HG-5epi activity" include the enzyme of the present invention. Examples of the "polypeptide having HG-5epi activity" include the polypeptide of the present invention.

No particular limitation is imposed on the aforementioned "polysaccharide including a disaccharide formed of a GlcNAc residue and a HexA residue," so long as the polysaccharide serves as a substrate on which the HG-5epi of the present invention acts.

As used herein, the "disaccharide formed of a GlcNAc residue and a HexA residue" refers to a disaccharide in which a GlcNAc residue is bonded to a HexA residue. No particular limitation is imposed on the sequential order of the GlcNAc residue and the HexA residue in the "disaccharide formed of a GlcNAc residue and a HexA residue." It is sufficient that one molecule of the polysaccharide has at least one "disaccharide formed of a GlcNAc residue and a HexA residue" in the polysaccharide backbone thereof. In other words, one molecule of the polysaccharide may have one or two or more "disaccharides each formed of a GlcNAc residue and a HexA residue" in the polysaccharide backbone thereof. When one molecule of the polysaccharide has two or more "disaccharides each formed of a GlcNAc residue and a HexA residue," two or more disaccharides may be bonded together to form, in the polysaccharide backbone thereof, a glycan having a length of four or more saccharide residues, or may be bonded by the mediation of another molecule in the polysaccharide backbone of the polysaccharide. As used herein, the "another molecule" refers to, for example, a glycan formed of one or more saccharide residues, other than a disaccharide formed of a GlcNAc residue and a HexA residue.

No particular limitation is imposed on the bonding mode of the GlcNAc residue to the HexA residue in the "disaccharide formed of a GlcNAc residue and a HexA residue," so long as the HG-5epi of the present invention can act thereon. The bonding mode of the "disaccharide formed of a GlcNAc residue and a HexA residue" is preferably 1-4 glycoside bonding. Regarding anomers of the GlcNAc residue and the HexA residue in the "disaccharide formed of a GlcNAc residue and a HexA residue," the GlcNAc residue is preferably α-anomer, the GlcA residue is preferably β-anomer, and the IdoA residue is preferably α-anomer.

Specific examples of the "disaccharide formed of a GlcNAc residue and a HexA residue" include a disaccharide having a bond between the GlcNAc residue and the GlcA residue represented by [-4GlcNAcα1-4GlcAβ1-] or [-4GlcAβ1-4GlcNAcα1-]; and a disaccharide having a bond between the GlcNAc residue and the IdoA residue represented by [-4GlcNAcα1-4IdoAα1-] or [-4IdoAα1-4GlcNAcα1-]. Specific examples of the polysaccharide including such a "disaccharide formed of a GlcNAc residue and a HexA residue" include NAH, completely desulfated N-acetylated HS (CDSNAc-HS), CDSNAc-HEP, and ACH (2-0-desulfated AS). Of these, NAH and CDSNAc-HEP are preferred.

As used herein, the "epimerization of HexA residues" refers to epimerization of GlcA residues to IdoA residues and/or epimerization of IdoA residues to GlcA residues. Thus, as used herein, the "polysaccharide in which HexA residues has been epimerized" refers to a polysaccharide obtained through a step of bringing the HG-5epi of the present invention into contact with a polysaccharide including disaccharides formed of a GlcNAc residue and a HexA residue. Specifically, the procedure includes a step of epimerizing the entirety or part of GlcA residues of the disaccharides contained in the polysaccharide backbone into IdoA residues, and/or a step of epimerizing the entirety or part of IdoA residues of the disaccharides contained in the polysaccharide backbone into GlcA residues.

The polysaccharide production method of the present invention encompasses a method of epimerizing HexA residues of disaccharides contained in the polysaccharide backbone including the disaccharides formed of a GlcNAc residue and a HexA residue (i.e., a HexA residue adjacent to a GlcNAc residue), to thereby increase or decrease the IdoA content of the polysaccharide; and a method of producing a polysaccharide employing the epimerization method.

Specific examples of the "polysaccharide in which HexA residues has been epimerized" include a polysaccharide having a structure in which the entirety or part of the GlcA residues of NAH have been epimerized into IdoA residues, and a polysaccharide having a structure in which the entirety or part of the GlcA residues of CDSNAc-HEP have been epimerized into IdoA residues and/or the entirety or part of the IdoA residues of CDSNAc-HEP have been epimerized into GlcA residues.

The "polysaccharide in which HexA residues has been epimerized" may be a polysaccharide having IdoA residues. No particular limitation is imposed on the IdoA content of the "polysaccharide in which HexA residues has been epimerized," and it can be controlled to be any value in accordance with the conditions under which the HG-5epi of the present invention is brought into contact with a polysaccharide including disaccharides formed of a GlcNAc residue and a HexA residue. In one specific manner, conditions including the amount of the HG-5epi of the present invention added to the reaction and the reaction time are appropriately predetermined, so as to attain desired IdoA content. The term "IdoA content" has the same definition as described in detail in the aforementioned "(1) Enzyme of the present invention."

The "polysaccharide in which HexA residues has been epimerized" may be a polysaccharide having IdoA content different from that of HEP (IdoA content: 77%) and that of HS (IdoA content: 19%) (Hook M, Lindahl U, Iverius P. H., Biochem. J. 1974 January; 137(1): 33-43.).

The IdoA content of the "polysaccharide in which HexA residues has been epimerized" may be appropriately adjusted. The IdoA content of the "polysaccharide in which HexA residues has been epimerized" may be, for example, 0.1% or more, 1% or more, 5% or more, 10% or more, 20% or more, 25% or more, 30% or more, 35% or more, 40% or more, or 50% or more. The "IdoA content" may also be, for example, 100% or less, 99% or less, 95% or less, 90% or less, 80% or less, 75% or less, 70% or less, 65% or less, 60% or less, 50% or less, 40% or less, 30% or less, 20% or less, 10% or less, 5% or less, or 1% or less. Preferred IdoA content ranges of the "polysaccharide in which HexA residues has been epimerized" include 20% to 75%, 25% to 75%, 30% to 75%, 35% to 75%, 40% to 75%, 20% to 70%, 25% to 70%, 30% to 70%, 35% to 70%, 40% to 70%, 20% to 65%, 25% to 65%, 30% to 65%, 35% to 65%, 40% to 65%, 20% to 60%, 25% to 60%, 30% to 60%, 35% to 60%, and 40% to 60%.

The polysaccharide in which HexA residues has been epimerized and which is obtained through the polysaccharide production method of the present invention is useful as a novel material.

EXAMPLES

The present invention will next be described in detail by way of examples, which should not be construed as limiting the technical scope of the invention thereto.

CDSNAc-HEP, CDSNS-HEP, NAH, and NSH employed in the Examples were obtained through a known method described in documents.

In preparation of CDSNAc-HEP and CDSNS-HEP, completely desulfated heparin (CDS-HEP) was used as an intermediate.

CDS-HEP was produced by desulfating HEP through a known method disclosed in a document. Specifically, HEP derived from the porcine intestine (product of Sigma Aldrich) was subjected to 6-O-desulfation by use of N-methyl-N-(trimethylsilyl)-trifluoroacetamide (MTSTFA) and 2-O-desulfation by lyophilization in the presence of sodium hydroxide (Kariya Y., Herrmann J., Suzuki K., Isomura T., Ishihara M., J. Biochem. 1998 February; 123(2): 240-6.) and to N-desulfation by solvolysis in heated DMSO solvent (Ayotte L., Perlin A. S., Carbohydr. Res. 1986 Jan. 1; 145(2): 267-77.). The thus-obtained CDS-HEP has a structure in which all the sulfate groups of HEP are substantially removed.

CDSNAc-HEP was obtained by subjecting CDS-HEP to N-acetylation by use of acetic anhydride (Danishefsky I., Methods Carbohydr. Chem. 1965; 5: 407-409.).

CDSNS-HEP was obtained by subjecting CDS-HEP to N-sulfation by use of a sulfur trioxide-pyridine complex (Leali D., Belleri M., Urbinati C., Coltrini D., Oreste P., Zoppetti G., Ribatti D., Rusnati M., Presta M., J. Biol. Chem. 2001 Oct. 12; 276(41): 37900-8.).

NAH was obtained by culturing *E. coli* K5 cells (Serotype O10:K5(L):H4, ATCC 23506) and purifying the culture supernatant, in accordance with a known method described in a document (Japanese Patent Application Laid-Open (kokai) No. 2004-018840).

NSH was obtained by subjecting NAH to N-deacetylation in heated aqueous sodium hydroxide and N-sulfation by use of a sulfur trioxide-pyridine complex (Leali D., Belleri M., Urbinati C., Coltrini D., Oreste P., Zoppetti G., Ribatti D., Rusnati M., Presta M., J. Biol. Chem. 2001 Oct. 12; 276(41): 37900-8.).

Example 1

Isolation of mRNA from the *Achatina fulica* Mucous Gland

The mRNA of *Achatina fulica* was obtained through a hot phenol method (e.g., Verwoerd T. C., Dekker B. M., Hoekema A., Nucleic Acids Res. 1989 Mar. 25; 17(6): 2362.) in which the total RNA was extracted from the mucous gland, and the extracted product was purified through a method employing magnetic beads, to thereby isolate mRNA. The specific procedure is described as follows.

The mucous gland was removed through incision of an *Achatina fulica* by means of a surgical knife and the removed gland was washed with distilled water. The product was placed in a 1.5-mL tube with a screw sealable cap. The contents were frozen by immersing the tube in liquid nitrogen for one minute, and the gland was crushed by means of a homogenizer. To the crushed product, a hot extraction buffer heated at 80 deg C. in a water bath (i.e., a solution obtained by stirring phenol melted by heating in a water bath at 55° C. with a buffer (0.1M LiCl, 100 mM Tris-HCl (pH: 8.0), 10 mM EDTA, 1% SDS) at a ratio of 1:1) (0.5 mL) was added, and the mixture was stirred for 30 seconds by means of a test tube mixer. Subsequently, a chloroform solution (a solution prepared by mixing chloroform with isoamyl alcohol at a ratio of 24:1 under stirring) (0.25 mL) was added to the mixture, and the resultant mixture was further stirred for 30 seconds by means of a test tube mixer.

The thus-obtained solution was centrifuged at 20,000×g for 5 minutes, and an aliquot (0.2 mL) was removed from the supernatant (water layer). The aliquot was transferred to another tube, and 4M LiCl (0.2 mL) was added thereto. The mixture was sufficiently mixed, and the mixture was allowed to stand overnight at −20° C. Thereafter, the mixture was centrifuged at 4° C. and 20,000×g for 5 minutes, and the supernatant was removed, to thereby precipitate total RNA. The precipitated product was dissolved in distilled water (0.25 mL), and 3M CH$_3$COONa (pH: 5.2) (0.025 mL) and ethanol (0.5 mL) were added thereto, followed by mixing. Then, the mixture was centrifuged at 20,000×g for 5 minutes, and the supernatant was removed, to thereby re-precipitate total RNA. The product was washed with 70% ethanol (0.5 mL), and the supernatant was removed. The product was dried under air flow. Thus, again re-precipitated total RNA was prepared.

Distilled water (0.5 mL) was added to the precipitated total RNA, and the precipitates were dissolved by adding distilled water (0.5 mL) with mild pipetting. Then, mRNA derived from the *Achatina fulica* mucous gland was isolated from the solution by means of PolyATract (registered trademark) mRNA Isolation System (product of Promega) through a procedure in accordance with an attached protocol. Thus, mRNA derived from the *Achatina fulica* mucous gland was isolated from the solution.

Example 2

Preparation of *Achatina fulica* cDNA Phage Library cDNA was obtained from mRNA obtained in the aforementioned <Example 1> by means of AccuScript Hi-Fi cDNA Synthesis Kit (product of Agilent Technologies) through a procedure in accordance with an attached protocol. More specifically, reverse transcription was carried out by use of mRNA obtained in the above <Example 1> as a template, an oligo dT primer to which an XhoI site was added (SEQ ID NO: 6), 5-methyl dCTP, and Moloney murine leukemia virus reverse transcriptase (MMLV-RT). Then, in the presence of RNaseH, nick translation by DNA polymerase I was performed, to thereby yield a double-strand cDNA.

Both ends of the double-strand cDNA were blunted by acting Pfu DNA Polymerase attached to the kit. Then, an EcoRI adaptor (mentioned below) was ligated to the double-strand cDNA by use of DNA Ligation Kit Ver. 2.1 (product of Takara Bio Inc.), through a procedure in accordance with an attached protocol. Subsequently, the cDNA was limitedly digested with a restriction enzyme XhoI (product of Takara Bio Inc.) and purified by use of QIAEX II Gel Extraction Kit (product of Qiagen), through a procedure in accordance with an attached protocol, to thereby yield a cDNA fragment having an EcoRI cohesive end at the 5' end and an XhoI cohesive end at the 3' end.

The "EcoRI adaptor" refers to a DNA fragment having, at the 5' end, a structure which is generated by limited digestion with a restriction enzyme EcoRI. The DNA fragment may be produced by, for example, mixing a DNA fragment consisting of the nucleotide sequence defined by SEQ ID NO: 7 and a DNA fragment consisting of the nucleotide sequence defined by SEQ ID NO: 8 in a solution, heating the mixture at 90 to 100° C. for 1 to 2 minutes, and cooling the mixture to room temperature. Preferably, the 5' end of the DNA fragment consisting of the nucleotide sequence defined by SEQ ID NO: 8 is phosphorylated, and the product is used in production of the EcoRI adaptor.

Then, the above cDNA fragment and Uni-ZAP XR (a cloning vector prepared by dephosphorylating 5' end of Lambda ZAP II (product of Agilent Technologies) which was limitedly digested with EcoRI and XhoI) were ligated, by use of DNA Ligation Kit Ver. 2.1, through a procedure in accordance with an attached protocol. Subsequently, the thus-ligated vector was packaged into phage particles by use of Gigapack III Gold Packaging Extract (product of Agilent Technologies), through a procedure in accordance with an attached protocol, to thereby yield *Achatina fulica* cDNA phage library. The titer of the packaged phage solution was $1.0 \times 10^7$ pfu/mL.

Example 3

Recovery of DNA Fragment Encoding Polypeptide of HG-5Epi

As host cells (host bacterium) to which the cDNA phage library obtained in <Example 2> is to be infected, *E. coli* XL-1 Blue MRF' strain (product of Agilent Technologies) was used. Amplification and recovery of the phage were carried out through a plate lysate method, the details of which are mentioned below.

The host bacterium was inoculated to a LB medium (containing 0.2% maltose and 10 mM $MgSO_4$) (20 mL) and was subjected to shake culturing overnight at 37° C., to thereby yield a culture broth having an absorbance of about 1.5 at a wavelength of 600 nm. The cDNA phage library solution obtained in <Example 2> was dispensed in an amount of 30 μL into each of the three test tubes (capacity: 50 mL). The host bacterium culture broth (5 mL) was added to each test tube and mixed with the phage. Thereafter, the test tubes were allowed to stand in a water bath at 37° C. for 15 minutes, whereby the host bacterium was infected with the phage particles.

For forming plaques by culturing the phage-particle-infected host bacterium on a plate, the following stack structure was constructed. Specifically, LB top agar (agar concentration: 0.7%) (35 mL), heated at 45° C., was added to each test tube holding a mixture of the phage particles and the host bacterium, and the contents were rapidly mixed. The agar mixture was stacked on three LB plates (24 cm×24 cm). The plates were subjected to static culturing at 37° C. for 6 hours, for forming plaques.

To each plate on which plaques were formed, a mixture of an SM buffer (0.1M NaCl, 10 mM $MgSO_4$—$H_2O$, 50 mM Tris-HCl (pH: 7.5), and 0.01% gelatin) (50 mL) and chloroform (1 mL) was added, and the plates were allowed to stand overnight at 4° C. The supernatant (40 mL) was recovered from each plate and transferred to a centrifugation tube. Chloroform (2 mL) was added to the tube, and the contents were stirred for several seconds by means of a test tube mixer. The centrifugation tubes were subjected to centrifugation at 8,000×g for 15 minutes, and the supernatants (35 mL/tube) were recovered from the tubes and combined. The thus-obtained solution was used as a phage solution. The titer of the recovered phage solution was $3.4 \times 10^9$ pfu/mL.

Next, λDNA was obtained from the phage solution by means of Lambda Mini Kit (product of Qiagen), through a procedure in accordance with an attached protocol, and PCR was conducted by use of the λDNA (0.5 μg) as a template. In PCR, an oligonucleotide defined by SEQ ID NO: 9, SEQ ID NO: 10, or SEQ ID NO: 11 was used as a sense primer, and in combination, an oligonucleotide defined by SEQ ID NO: 12 or SEQ ID NO: 13 was used as an anti-sense primer. In PCR, gene amplification was performed by use of Ex Taq DNA Polymerase (product of Takara Bio Inc.), through a procedure in accordance with an attached protocol. PCR conditions included 94° C. for 2 minutes, (94° C. for 30 seconds, 55° C. for 1 minute, and 72° C. for 2 minutes)×40 cycles, and 72° C. for 5 minutes. As a result, a DNA fragment (about 0.3 kbp) was obtained through PCR employing primers defined by SEQ ID NO: 9 and SEQ ID NO: 13.

This DNA fragment was purified by use of QIAEX II Gel Extraction Kit, through a procedure in accordance with an attached protocol. Then, blunting of the ends of the DNA fragment and phosphorylation of the 5' ends thereof were performed by use of Blunting Kination Ligation Kit (product of Takara Bio Inc.), through a procedure in accordance with an attached protocol. The thus-treated DNA fragment was purified again. The DNA fragment was then ligated with pBlue Script II SK(+) (product of Agilent Technologies) (hereinafter abbreviated as pBS), which was limitedly digested with a restriction enzyme EcoRV (product of New England Biolabs), followed by dephosphorylation with Alkaline Phosphatase, Calf Intestinal (CIP) (product of New England Biolabs).

By use of the ligation reaction mixture, E. coli JM109 cells (product of Takara Bio Inc.) were transformed. The transformant cells were applied onto an agar layer of a LB medium containing 50 µg/mL ampicillin (hereinafter referred to as LB/Amp), and the cells were statically cultured overnight at 37° C. Any three single colonies were selected from the plate, and each colony was inoculated to a LB/Amp medium (1 mL), followed by shake culturing at 37° C. for 5 hours. An aliquot (0.5 mL) was sampled from the culture and centrifuged at 20,000×g for 1 minute. Through removal of the supernatant, pellets of E. coli were recovered. Separately, an aliquot (10 µL) was taken from the remaining culture and inoculated to a LB/Amp medium (2 mL), followed by shake culturing overnight at 37° C.

The E. coli pellets were subjected to a conventional alkaline lysis mini-prep protocol (Sambrook J., et al., Molecular Cloning: A Laboratory Manual, Second Edition, Cold Spring Harbor Laboratory Press (1989)), to thereby obtain precipitates of a plasmid. The precipitated plasmid was dried in air and dissolved in distilled water (10 µL). Then, while the plasmid was used as a template, PCR was performed by use of T3 primer (SEQ ID NO: 14) and T7 primer (SEQ ID NO: 15). In PCR, gene amplification was performed by use of Ex Taq DNA Polymerase, through a procedure in accordance with an attached protocol. PCR conditions included (94° C. for 30 seconds, 60° C. for 30 seconds, and 72° C. for 1 minutes)×25 cycles. The PCR mixtures were subjected to agarose gel electrophoresis. In all the tested PCR mixtures, a DNA fragment (about 0.4 kbp) was confirmed.

Then, the aforementioned culture (2 mL) obtained through shake culturing overnight was centrifuged at 20,000×g for 1 minute, and the supernatant was removed therefrom, to thereby obtain pellets of E. coli. Thereafter, a plasmid was obtained from the E. coli pellets by use of Wizard (registered trademark) Plus SV Minipreps DNA Purification System (product of Promega), through a procedure in accordance with an attached protocol. In order to analyze the nucleotide sequence of a DNA fragment included in the plasmid, sequencing reaction was performed by use of the plasmid as a template. Specifically, the sequencing reaction was performed by use of BigDye (registered trademark) Terminator v3.1 Cycle Sequencing Kit (product of Applied Biosystems), through a procedure in accordance with an attached protocol. Sequence analysis was performed by means of ABI PRISM (registered trademark) 310 Genetic Analyzer (product of Applied Biosystems). As a result, the DNA was found to have the nucleotide sequence defined by SEQ ID NO: 16.

Example 4

Sequence of DNA Encoding Polypeptide of HG-5Epi

In order to sequence the DNA encoding the polypeptide of HG-5epi, sequencing of 5' end and 3' end unknown regions of the DNA fragment obtained in <Example 3> was performed through inverse PCR.

Specifically, the λDNA (6 µg) obtained in the above <Example 3> was limitedly digester with a restriction enzyme BamHI (product of Takara Bio Inc.) and the subjected to agarose gel electrophoresis. A gel portion corresponding to 0.5 to 4.0 kbp was cut out by a scalpel. The gel portion was treated with QIAEX II Gel Extraction Kit, through a procedure in accordance with an attached protocol, whereby a λDNA fragment limitedly digested with BamHI was obtained. Subsequently, a fragment of the λDNA was self-ligated by use of DNA Ligation Kit Ver. 2.1, through a procedure in accordance with an attached protocol. By use of the ligation reaction mixture as a template, PCR was performed with oligonucleotides defined by SEQ ID NOs: 17 and 18 as primers. PCR was performed by use of Ex Taq DNA Polymerase. PCR reaction mixture was prepared through a procedure in accordance with an attached protocol. PCR conditions included 94° C. for 2 minutes, (94° C. for 30 seconds, 50° C. for 30 seconds, and 72° C. for 3 minutes)×40 cycles, and 72° C. for 5 minutes.

Further, nested PCR was performed by use of the reaction mixture of the inverse PCR as a template. In PCR, oligonucleotides defined by SEQ ID NOs: 19 and 20 were used as primers. PCR was performed by use of Ex Taq DNA Polymerase. PCR reaction mixture was prepared through a procedure in accordance with an attached protocol. PCR conditions included (94° C. for 30 seconds, 50° C. for 30 seconds, and 72° C. for 3 minutes)×40 cycles. As a result, a DNA fragment (about 1.8 kbp) was obtained.

Blunting of the ends of the DNA fragment and phosphorylation of the 5' ends thereof were performed by use of Blunting Kination Ligation Kit, through a procedure in accordance with an attached protocol. Then, the DNA fragment was purified by use of Micropure EZ Enzyme Removers (product of Millipore). The DNA fragment was then ligated to pBS, which was limitedly digested with EcoRV, followed by dephosphorylation with CIP.

By use of the ligation reaction mixture, E. coli JM109 cells were transformed. The transformant cells were applied onto a plate of a LB/Amp agar medium, and the cells were statically cultured overnight at 37° C., to thereby obtain a single colony. The colony was inoculated to a LB/Amp medium (4 mL), and shake culturing was performed overnight at 37° C., to thereby obtain pellets of E. coli. Thereafter, a plasmid was obtained from the E. coli pellets by use of QIAprep Spin Miniprep Kit (product of Qiagen), through a procedure in accordance with an attached protocol. In order to analyze the nucleotide sequence of a DNA fragment included in the plasmid, sequencing reaction was performed by use of the plasmid as a template. Specifically, the sequencing reaction was performed by use of BigDye Terminator v3.1 Cycle Sequencing Kit, through a procedure in accordance with an attached protocol. Sequence analysis was performed by means of ABI PRISM 310 Genetic Analyzer. The analysis has revealed that the DNA fragment obtained through nested PCR is a DNA having, at both ends thereof, a part of the nucleotide sequence obtained in <Example 3> and defined by SEQ ID NO: 16. Through the analysis, the nucleotide sequences of both ends of cDNA including the nucleotide sequence defined by SEQ ID NO: 16 in the self-ligated λDNA fragment were also determined.

Next, PCR cloning was performed by use of primers which can be annealed to the respective ends of the cDNA, so as to recover the full-length DNA encoding HG-5epi. Specifically, PCR was performed by use of oligonucleotides defined by SEQ ID NOs: 21 and 22 as primers and λDNA (0.5 µg) prepared in <Example 3> as a template. PCR was performed by use of PfuTurbo DNA Polymerase (product of Agilent Technologies). PCR reaction mixture was prepared through a procedure in accordance with an attached protocol. PCR conditions included 94° C. for 2 minutes, (94° C. for 30 seconds, 55° C. for 30 seconds, and 72° C. for 2 minutes)×40 cycles, and 72° C. for 5 minutes. As a result, a DNA fragment (about 1.1 kbp) was obtained.

This DNA fragment was purified by use of QIAEX II Gel Extraction Kit, through a procedure in accordance with an attached protocol. Subsequently, blunting of the ends of the DNA fragment and phosphorylation of the 5' ends thereof were performed by use of Blunting Kination Ligation Kit, through a procedure in accordance with an attached protocol. The thus-treated DNA fragment was purified again. The DNA fragment was then ligated with pBS, which was limitedly digested with EcoRV, followed by dephosphorylation with CIP.

By use of the ligation reaction mixture, E. coli JM109 cells were transformed. The transformant cells were applied onto a LB/Amp agar medium, and the cells were statically cultured overnight at 37° C. Three single colonies were selected, and each colony was inoculated to a LB/Amp medium (4 mL), followed by shake culturing overnight at 37° C. The culture was centrifuged at 20,000×g for 1 minute. Through removal of the supernatant, pellets of E. coli were recovered. Thereafter, a plasmid was obtained from the E. coli pellets by use of Wizard Plus SV Minipreps DNA Purification System, through a procedure in accordance with an attached protocol. In order to analyze the nucleotide sequence of a DNA fragment included in the plasmid, sequencing reaction was performed by use of the plasmid as a template. Specifically, the sequencing reaction was performed by use of BigDye Terminator v3.1 Cycle Sequencing Kit, through a procedure in accordance with an attached protocol. Sequence analysis was performed by means of ABI PRISM 310 Genetic Analyzer. As a result, the DNA obtained through PCR cloning was found to have the nucleotide sequence defined by SEQ ID NO: 23.

However, when the amino acid sequence of HG-5epi deduced from the nucleotide sequence defined by SEQ ID NO: 23 was compared with the amino acid sequence of a known C5-epi (described in Referential Example 1), the nucleotide sequence defined by SEQ ID NO: 23 was conceived to be incomplete due to lack of a region encoding the N-terminus side of HG-5epi. Thus, in order to sequence the 5'-terminal sequence of cDNA including the nucleotide sequence defined by SEQ ID NO: 23, an unknown region of DNA was amplified through the 5' RACE technique. Preparation of cDNA serving as a template of 5' RACE reaction and 5' RACE reaction itself were conducted by use of Marathon(registered trademark) cDNA Amplification Kit (product of Clontech), through a procedure in accordance with an attached protocol. As the RNA serving as a material of cDNA synthesis, mRNA (0.5 µg) purified in <Example 1> was used. Oligonucleotides defined by SEQ ID NOs: 24 and 25 were used as primers. A dilute of cDNA to which Marathon cDNA adaptor was bonded was used as a template. PCR was performed by use of Advantage (registered trademark) 2 Polymerase mix (product of Clontech). PCR reaction mixture was prepared through a procedure in accordance with an attached protocol. PCR conditions included 94° C. for 30 seconds, (94° C. for 5 seconds, 72° C. for 4 minutes)×5 cycles, (94° C. for 5 seconds, 70° C. for 4 minutes)×5 cycles, and (94° C. for 5 seconds, 68° C. for 4 minutes)×25 cycles.

Further, nested PCR was performed by use of the 5' RACE reaction mixture as a template. In PCR, oligonucleotides defined by SEQ ID NOs: 26 and 27 were used as primers. PCR was performed by use of Advantage 2 Polymerase mix. PCR reaction mixture was prepared through a procedure in accordance with an attached protocol. PCR conditions included 94° C. for 30 seconds, (94° C. for 5 seconds, 72° C. for 4 minutes)×5 cycles, (94° C. for 5 seconds, 70° C. for 4 minutes)×5 cycles, and (94° C. for 5 seconds, 68° C. for 4 minutes)×25 cycles. As a result, a DNA fragment (about 1.2 kbp) was obtained.

This DNA fragment was purified by use of QIAEX II Gel Extraction Kit, through a procedure in accordance with an attached protocol. Subsequently, blunting of the ends of the DNA fragment and phosphorylation of the 5' ends thereof were performed by use of Blunting Kination Ligation Kit, through a procedure in accordance with an attached protocol. The thus-treated DNA fragment was purified again. The DNA fragment was then ligated with pBS, which was limitedly digested with a restriction enzyme EcoRV, followed by dephosphorylation with CIP.

By use of the ligation reaction mixture, E. coli JM109 cells were transformed. The transformant cells were applied onto a LB/Amp agar medium, and the cells were statically cultured overnight at 37° C. Three single colonies were selected, and each colony was inoculated to a LB/Amp medium (4 mL), followed by shake culturing overnight at 37° C. The culture was centrifuged at 20,000×g for 1 minute. Through removal of the supernatant, pellets of E. coli were recovered. Thereafter, a plasmid was obtained from the E. coli pellets by use of Wizard Plus SV Minipreps DNA Purification System, through a procedure in accordance with an attached protocol. In order to analyze the nucleotide sequence of a DNA fragment included in the plasmid, sequencing reaction was performed by use of the plasmid as a template. Specifically, the sequencing reaction was performed by use of BigDye Terminator v3.1 Cycle Sequencing Kit, through a procedure in accordance with an attached protocol. Sequence analysis was performed by means of ABI PRISM 310 Genetic Analyzer. As a result, the DNA obtained through 5' RACE reaction was found to have the nucleotide sequence defined by SEQ ID NO: 28.

Example 5

Cloning of DNA Encoding Full-Length Polypeptide of HG-5Epi

The pBSs ligated with the DNA fragments of HG-5epi obtained in the above <Example 4> were each limitedly digested with the same restriction enzymes, followed by ligation, whereby a vector (pBS/HG-5epi), into which a DNA encoding the full-length HG-5epi was sub-cloned, was produced. The specific procedure is as follows.

The pBS ligated with a DNA consisting of the nucleotide sequence defined by SEQ ID NO: 28 was limitedly digested with EcoRI (product of Takara Bio Inc.) and EcoRV, to thereby obtain a DNA fragment (about 1.2 kbp) including a DNA encoding the N-terminal side of HG-5epi. The DNA fragment was purified by use of QIAEX II Gel Extraction Kit, through a procedure in accordance with an attached protocol.

Also, the pBS ligated with a DNA consisting of the nucleotide sequence defined by SEQ ID NO: 23 was limitedly digested with EcoRI and EcoRV, to thereby obtain a DNA fragment (about 3.7 kbp) including a DNA encoding the C-terminal side of HG-5epi and a DNA of pBS. The DNA fragment was purified by use of QIAEX II Gel Extraction Kit, through a procedure in accordance with an attached protocol. Subsequently, the DNA fragment was dephosphorylated with CIP and purified again.

Notably, EcoRI cleaves one site of pBS. EcoRV cleaves one site of an overlapping region between the DNA consisting of the nucleotide sequence defined by SEQ ID NO: 28 and the DNA consisting of the nucleotide sequence defined by SEQ ID NO: 23. Therefore, through ligation of the above-produced two DNA fragments, a DNA encoding the full-length HG-5epi sub-cloned into pBS can be yielded.

The thus-produced two DNA fragments were ligated by use of DNA Ligation Kit Ver. 2.1, through a procedure in accordance with an attached protocol. By use of the ligation reaction mixture, E. coli JM109 cells were transformed. The transformant cells were applied onto a plate of a LB/Amp agar medium, and the cells were statically cultured overnight at 37° C., to thereby obtain a single colony. The colony was inoculated to a LB/Amp medium (4 mL), and shake culturing was performed overnight at 37° C., to thereby obtain pellets of E. coli. Thereafter, a plasmid was obtained from the E. coli pellets by use of QIAprep Spin Miniprep Kit, through a procedure in accordance with an attached protocol. In order to analyze the nucleotide sequence of a DNA fragment included in the plasmid, sequencing reaction was performed by use of the plasmid as a template. Specifically, the sequencing reaction was performed by use of BigDye Terminator v3.1 Cycle Sequencing Kit, through a procedure in accordance with an attached protocol. Sequence analysis was performed by means of ABI PRISM 310 Genetic Analyzer. The analysis has revealed that a DNA sub-cloned into pBS included the nucleotide sequence defined by SEQ ID NO: 1.

Referential Example 1

Homology of Known C5-Epi to HG-5Epi

Homology of the amino acid sequence (SEQ ID NO: 2) of HG-5epi encoded by the DNA consisting of the nucleotide sequence defined by SEQ ID NO: 1 with respect to the amino acid sequence of a known C5-epi was analyzed by GENETYX (registered trademark) Ver. 11 (product of Genetyx Corp.). The homology with respect to a human-derived C5-epi (NCBI Accession No.: NP_056369, SEQ ID NO: 3) was 39%, to zebrafish-derived C5-epi (NCBI Accession No.: NP_998015, SEQ ID NO: 4) was 39%, and to nematode-derived C5-epi (NCBI Accession No.: NP_497876, SEQ ID NO: 5) was 30%.

Referential Example 2

Analysis of Hydrophobicity Profile of HG-5Epi

Hydrophobicity profile of the amino acid sequence (SEQ ID NO: 2) of HG-5epi was analyzed. The analysis has suggested that HG-5epi conceivably has a transmembrane region at the N-terminus. Thus, the region consisting of base NOs: 100 to 1,806, the nucleotide sequence defined by SEQ ID NO: 1 excepting the region possibly encoding the N-terminal transmembrane region, was employed in the below-mentioned experiments of HG-5epi expression.

Example 6

Production of Vector for HG-5Epi Expression in Insect Cells (1)

For producing a vector for HG-5epi expression in insect cells, PCR was performed by using pBS/HG-5epi obtained in the above <Example 5> as a template. In PCR, oligonucleotides defined by SEQ ID NOs: 29 and 30 were used as primers. PCR was performed by use of Accuprime Taq DNA Polymerase High Fidelity (product of Invitrogen). PCR reaction mixture was prepared through a procedure in accordance with an attached protocol. PCR conditions included 94° C. for 20 seconds, and (94° C. for 20 seconds, 58° C. for 20 seconds, 68° C. for 3 minutes)×20 cycles. As a result, a DNA fragment (about 1.7 kbp) was obtained.

This DNA fragment was purified by use of MinElute Gel Extraction Kit (product of Qiagen), through a procedure in accordance with an attached protocol. The thus-purified DNA fragment was limitedly digested with restriction enzymes EcoRI and NotI (products of Takara Bio Inc.) and purified again in a similar manner. An expression vector, pFBIF1 (mentioned below) was also subjected to limited digestion with the same restriction enzymes and purification. Then, the DNA fragment was ligated to pFBIF1 by use of T4 DNA Ligase (product of New England Biolabs), through a procedure in accordance with an attached protocol.

By use of the ligation reaction mixture, E. coli DH5α cells (product of Toyobo) were transformed. The transformant cells were applied onto a plate of a LB/Amp agar medium, and the cells were statically cultured overnight at 37° C., to thereby obtain a single colony. The colony was inoculated to a LB/Amp medium (4 mL), and shake culturing was performed overnight at 37° C., to thereby obtain pellets of E. coli. Thereafter, a vector was obtained from the E. coli pellets by use of QIAprep Spin Miniprep Kit, through a procedure in accordance with an attached protocol. Subsequently, through sequencing reaction by use of BigDye Terminator v3.1 Cycle Sequencing Kit, sequence analysis was carried out by means of Applied Biosystems 3130xl Genetic Analyzer (product of Applied Biosystems). The analysis has revealed that the nucleotide sequence of the thus-ligated DNA fragment is the same as the nucleotide sequence defined by base NOs: 100 to 1,806 of SEQ ID NO: 1. Thus, a vector for HG-5epi expression in insect cells (pFBIF1/HG-5epi) was yielded.

As used herein the "pFBIF1" refers to an insect-cell expression vector which is produced by inserting, into a multi-cloning site of pFastBac1 (product of Invitrogen), a DNA encoding the amino acid sequence (SEQ ID NO: 34) of a polypeptide consisting of the amino acid sequence (SEQ ID NO: 31) of a mouse Igκ chain secretion signal peptide and the amino acid sequence (SEQ ID NO: 32) of a FLAG tag. Specifically, pFBIF1 is a vector produced through the following procedure. Firstly, PCR is performed by use of a vector into which a DNA consisting of the nucleotide sequence defined by SEQ ID NO: 33 is sub-cloned as a template and oligonucleotides defined by SEQ ID NOs: 35 and 36 as primers, to thereby obtain a DNA fragment. The DNA fragment is inserted into a segment of having pFast-Bac1 having a BamHI end and an EcoRI end, through the same technique as the above method employing restriction enzymes and T4 DNA Ligase.

The DNA consisting of the nucleotide sequence defined by SEQ ID NO: 33 may be prepared by, for example, synthesizing oligonucleotides having the corresponding nucleotide sequence and a nucleotide complementary thereto; phosphorylating the 5' end of the each oligonucleotides with T4 Polynucleotide Kinase; mixing the oligonucleotides in a solution; heating the mixture at 90 to 100° C. for 1 to 2 minutes; and cooling the mixture to room temperature. Therefore, by sub-cloning the DNA into any vector (e.g., pBS which has been limitedly digested with EcoRV and dephosphorylated with CIP), the product may be used as a template in the aforementioned PCR.

The thus-obtained pFBIF1/HG-5epi is a vector for fusion polypeptide expression, the fusion polypeptide being consisting of a mouse Igκ chain secretion signal, a FLAG tag, a dipeptide linker formed of asparagine and serine, and a polypeptide consisting of the amino acid sequence defined by amino acid NOs: 34 to 601 of SEQ ID NO: 2.

Example 7

Preparation of Bacmid for HG-5Epi Expression (1)

Next, transgenesis was performed between pFBIF1/HG-5epi and a bacmid by use of Bac-to-Bac (registered trademark) Baculovirus expression system (product of Invitrogen), through a procedure in accordance with an attached protocol. Through the transgenesis, a DNA encoding a fusion polypeptide consisting of a mouse Igκ chain secretion signal, a FLAG tag, a dipeptide linker formed of asparagine and serine, and a polypeptide consisting of the amino acid sequence defined by amino acid NOs: 34 to 601 of SEQ ID NO: 2 was inserted into a bacmid.

More specifically, by use of pFBIF1/HG-5epi, *E. coli* DH10Bac cells (product of Invitrogen) for preparation of a bacmid were transformed. The transformant cells were applied onto a plate of a LB agar medium containing kanamycin, gentamycin, tetracycline, 5-bromoindolyl β-D-galactopyranoside (Bluo-gal), and isopropyl β-D-thiogalactopyranoside (IPTG), and the cells were statically cultured overnight at 37° C., to thereby obtain a single white colony. The colony was inoculated to a LB medium (1.5 mL), and shake culturing was performed overnight at 37° C., to thereby obtain pellets of *E. coli*. Thereafter, a bacmid was obtained from the *E. coli* pellets, through a procedure in accordance with a protocol attached to the Bac-to-Bac Baculovirus expression system. Insertion of a DNA of interest in a full-length manner into a bacmid was confirmed through agarose gel electrophoresis, by determining the dimension of a DNA fragment amplified by PCR employing M13 Forward (−40) (SEQ ID NO: 41) and M13 Reverse (SEQ ID NO: 42) as primers.

Example 8

Preparation of HG-5Epi by Use of Insect Cells (1)

The bacmid obtained in the above <Example 7> was incorporated into insect cells Sf21. Specifically, Sf21 cells ($8 \times 10^5$ cells) were seeded to Grace's Insect Medium, Unsupplemented (product of Invitrogen) (2 mL) placed in a 35-mm Petri dish, and incubated at 27° C. for 1 hour, to thereby adhere the cells onto the dish. After confirmation of cell adhesion to the dish, lipid-DNA complexes solution (mentioned below) (0.2 mL) was added thereto, and the cells were incubated at 27° C. for 5 hours. Subsequently, the medium was removed from the dish through suction, and then Sf900 III medium (product of Invitrogen) (4 mL) was added thereto, followed by incubation at 27° C. for 72 hours. Then, the cells separated from the plate through pipetting and the culture broth were collected, and the collected matter was centrifuged at 5,000×g for 5 minutes. The supernatant was recovered as a primary virus solution.

As used herein, the "lipid-DNA complexes solution" refers to a solution prepared by gently and sufficiently mixing separately prepared solution A (i.e., a mixture of Grace's Insect Medium, Unsupplemented (100 μL) and bacmid (0.1 μg/μL) (10 μL)) and separately prepared solution B (i.e., a mixture of Grace's Insect Medium, Unsupplemented (100 μL) and Cellfectin (registered trademark) II Reagent (product of Invitrogen) (8 μL)), and allowing the resultant mixture to stand at room temperature for 30 minutes.

The entirety of the above primary virus solution was added to a culture broth of Sf21 cells ($5 \times 10^7$ cells) seeded to Sf900 III medium (50 mL) placed in a Spinner flask (capacity: 100 mL), and the cells were cultured under stirring at 27° C. for 72 hours. Then, the culture broth was centrifuged at 5,000×g for 5 minutes, and the supernatant was recovered as a secondary virus solution.

The secondary virus solution (40 mL) was added to a culture broth of Sf21 cells ($1 \times 10^9$ cells) seeded to Sf900 III medium (900 mL) placed in a baffle flask (capacity: 3 L), and the cells were cultured under shaking at 27° C. for 72 hours. Then, the culture broth was centrifuged at 10,000×g for 20 minutes, and the supernatant was recovered, to thereby obtain a culture broth containing HG-5epi.

Example 9

Purification of HG-5Epi (1)

To the HG-5epi-containing culture broth (80 mL) obtained in the above <Example 8>, 10% CHAPS (3-[(3-cholamidopropyl)dimethylammonio]propanesulfonate) (1.6 mL) was added, with gentle stirring. The entirety of the resultant solution was applied to Hi Trap Heparin HP column (product of GE Healthcare) (1 mL) equilibrated with 50 mM Tris-HCl (pH: 7.4)/0.1% CHAPS (10 mL), at a flow rate of 1 mL/min. Subsequently, HG-5epi was eluted through passage of 50 mM Tris-HCl (pH: 7.4)/0.1% CHAPS (4 mL) at a flow rate of 0.2 mL/min.

An HG-5epi-eluted fraction was confirmed through western blotting employing M2 monoclonal antibody (product of Sigma Aldrich) serving as an anti-FLAG antibody. Specifically, the elution fraction obtained in the above column purification was subjected to SDS-polyacrylamide gel electrophoresis (SDS-PAGE) under reducing conditions. The proteins separated in the gel were transferred to a PVDF membrane through a semi-dry method. After transferring the proteins, the PVDF membrane was immersed in a 5% skimmed milk-containing TBS-T (20 mM Tris-HCl (pH: 7.4), 500 mM NaCl, 0.2% TritonX-100, 0.05% Tween 20), with shaking at room temperature for 1 hour, to thereby block the membrane. Subsequently, a peroxidase-labeled anti-FLAG antibody (product of Sigma Aldrich) was 2,000-fold diluted with 5% skimmed milk-containing TBS-T, to thereby provide a solution. The PVDF membrane was immersed in the solution, with shaking at room temperature for 1 hour, to thereby perform antibody staining. The PVDF membrane was washed with TBS-T and immersed in Super-Signal (registered trademark) West Dura (product of Thermo Scientific) for 1 minute. Thereafter, a luminescent signal was detected by means of Image Quant LAS4000 (product of GE Healthcare). The luminescent signal intensity (luminance) of Amino-terminal FLAG-BAP Fusion Protein (concentration-known standard sample, product of Sigma Aldrich), which was also subjected to electrophoresis, was also determined. Through comparison of the luminescent signal intensities, the HG-5epi (protein) concentration was calculated as 0.4 μg/μL.

The thus-obtained HG-5epi-eluted fraction was employed as "roughly purified recombinant HG-5epi" in the subsequent experiments.

Example 10

Production of Vector for HG-5Epi Expression in Insect Cells (2)

For producing a vector for HG-5epi expression in insect cells, PCR was performed by using pBS/HG-5epi obtained in the above <Example 5> as a template. In PCR, oligonucleotides defined by SEQ ID NOs: 37 and 38 were used as primers. PCR was performed by use of Accuprime Taq DNA Polymerase High Fidelity. PCR reaction mixture was prepared through a procedure in accordance with an attached protocol. PCR conditions included 94° C. for 20 seconds, and (94° C. for 20 seconds, 62° C. for 20 seconds, 68° C. for 4 minutes)×18 cycles. By use of TOPO (registered trademark) TA Cloning (registered trademark) Kit (product of Invitrogen), and a procedure in accordance with an attached protocol was performed, whereby a vector in which the amplified DNA fragment was inserted into pCR (registered trademark) 2.1-TOPO was obtained.

By use of the vector, E. coli DH5α cells were transformed. The transformant cells were applied onto a plate of a LB/Amp agar medium, and the cells were statically cultured overnight at 37° C., to thereby obtain a single colony. The colony was inoculated to a LB/Amp medium (2 mL), and shake culturing was performed overnight at 37° C., to thereby obtain pellets of E. coli. Thereafter, a vector was obtained from the E. coli pellets by use of QIAprep Spin Miniprep Kit, through a procedure in accordance with an attached protocol. This vector was limitedly digested with restriction enzymes SalI (product of Takara Bio Inc.) and KpnI (product of Takara Bio Inc.), and a DNA fragment (about 1.7 kbp) was purified by use of MinElute Gel Extraction Kit, through a procedure in accordance with an attached protocol. An expression vector, pFBIF2 (mentioned below) was also subjected to limited digestion with the same restriction enzymes and purification. Then, the DNA fragment was ligated to pFBIF2 by use of T4 DNA Ligase, through a procedure in accordance with an attached protocol.

By use of the ligation reaction mixture, E. coli TOP10 cells (product of Invitrogen) were transformed. The transformant cells were applied onto a plate of a LB/Amp agar medium, and the cells were statically cultured overnight at 37° C., to thereby obtain a single colony. The colony was inoculated to a LB/Amp medium (4 mL), and shake culturing was performed overnight at 37° C., to thereby obtain pellets of E. coli. Thereafter, a vector was obtained from the E. coli pellets by use of QIAprep Spin Miniprep Kit, through a procedure in accordance with an attached protocol. Subsequently, through sequencing reaction by use of BigDye Terminator v3.1 Cycle Sequencing Kit, sequence analysis was carried out by means of Applied Biosystems 3130xl Genetic Analyzer. The analysis has revealed that the nucleotide sequence of thus-ligated DNA fragment is the same as the nucleotide sequence defined by base NOs: 100 to 1,806 of SEQ ID NO: 1. Thus, a vector for HG-5epi expression in insect cells (pFBIF2/HG-5epi) was yielded.

As used herein the "pFBIF2" refers to an insect-cell expression vector which is produced by inserting, into a multi-cloning site of pFastBac1, a DNA encoding the amino acid sequence (SEQ ID NO: 34) of a polypeptide consisting of the amino acid sequence (SEQ ID NO: 31) of a mouse Igκ chain secretion signal peptide and the amino acid sequence (SEQ ID NO: 32) of a FLAG tag. Specifically, pFBIF2 is a vector produced through the following procedure. Firstly, PCR is performed by use of a vector into which a DNA consisting of the nucleotide sequence defined by SEQ ID NO: 33 is sub-cloned as a template and oligonucleotides defined by SEQ ID NOs: 39 and 40 as primers, to thereby obtain a DNA fragment. The DNA fragment is inserted into a segment of having pFastBac1 having a EcoRI end and an SalI end, through the same technique as the above method employing restriction enzymes and T4 DNA Ligase.

The thus-obtained pFBIF2/HG-5epi is a vector for fusion polypeptide expression, the fusion polypeptide being consisting of a mouse Igκ chain secretion signal, a FLAG tag, a dipeptide linker formed of valine and aspartic acid, and a polypeptide consisting of the amino acid sequence defined by amino acid NOs: 34 to 601 of SEQ ID NO: 2.

Example 11

Preparation of Bacmid for HG-5Epi Expression (2)

Next, transgenesis was performed between pFBIF2/HG-5epi and a bacmid by use of Bac-to-Bac (registered trademark) Baculovirus expression system (product of Invitrogen), through a procedure in accordance with an attached protocol. Through the transgenesis, a DNA encoding a fusion polypeptide consisting of a mouse Igκ chain secretion signal, a FLAG tag, a dipeptide linker formed of valine and aspartic acid, and a polypeptide consisting of the amino acid sequence defined by amino acid NOs: 34 to 601 of SEQ ID NO: 2 was inserted into a bacmid.

More specifically, by use of pFBIF2/HG-5epi, E. coli DH10Bac cells for preparation of a bacmid were transformed. The transformant cells were applied onto a plate of a LB agar medium containing kanamycin, gentamycin, tetracycline, 5-bromoindolyl β-D-galactopyranoside (Bluogal), and isopropyl β-D-thiogalactopyranoside (IPTG), and the cells were statically cultured overnight at 37° C., to thereby obtain a single white colony. The colony was inoculated to a LB medium (1.5 mL), and shake culturing was performed overnight at 37° C., to thereby obtain pellets of E. coli. Thereafter, a bacmid was obtained from the E. coli pellets, through a procedure in accordance with a protocol attached to the Bac-to-Bac Baculovirus expression system. Insertion of a DNA of interest in a full-length manner into a bacmid was confirmed through agarose gel electrophoresis, by determining the dimension of a DNA fragment amplified by PCR employing M13 Forward (-40) (SEQ ID NO: 41) and M13 Reverse (SEQ ID NO: 42) as primers.

Example 12

Preparation of HG-5Epi by Use of Insect Cells (2)

The bacmid obtained in the above <Example 11> was incorporated into insect cells Sf21. Specifically, Sf21 cells ($8 \times 10^5$ cells) were seeded to Grace's Insect Medium, Unsupplemented (2 mL) placed in a 35-mm Petri dish, and incubated at 27° C. for 1 hour, to thereby adhere the cells onto the dish. After confirmation of cell adhesion to the dish, lipid-DNA complexes solution (mentioned below) (0.2 mL) was added thereto, and the cells were incubated at 27° C. for 5 hours. Subsequently, the medium was removed from the dish through suction, and then Sf900 III medium (product of Invitrogen) (4 mL) was added thereto, followed by incubation at 27° C. for 72 hours. Then, the cells separated from the plate through pipetting and the culture broth were collected as a primary virus solution.

As used herein, the "lipid-DNA complexes solution" refers to a solution produced by gently and sufficiently mixing separately prepared solution A (i.e., a mixture of Grace's Insect Medium, Unsupplemented (100 μL) and bacmid (0.1 μg/μL) (10 μL)) and separately prepared solution B (i.e., a mixture of Grace's Insect Medium, Unsupplemented (100 μL) and Cellfectin II Reagent (8 μL)), and allowing the resultant mixture to stand at room temperature for 30 minutes.

The entirety of the above primary virus solution was added to a culture broth of Sf21 cells (1×10⁸ cells) seeded to Sf900 III medium (100 mL) placed in a Spinner flask (capacity: 200 mL), and the cells were cultured under stirring at 27° C. for 72 hours. Then, the culture supernatant was recovered as a secondary virus solution.

The entirety of the secondary virus solution was added to a culture broth of Sf21 cells (2×10⁹ cells) seeded to Sf900 III medium (1.8 L) placed in a baffle flask (capacity: 3 L), and the cells were cultured under shaking at 27° C. for 96 hours. Then, the culture broth was centrifuged at 10,000×g for 20 minutes, and the supernatant was recovered, to thereby obtain a culture broth containing HG-5epi.

Example 13

Purification of HG-5Epi (2)

To the HG-5epi-containing culture broth (400 mL) obtained in the above <Example 12>, 10% CHAPS (3-[(3-cholamidopropyl)dimethylammonio]propanesulfonate) (8 mL) was added, with gentle stirring. The entirety of the resultant solution was applied to Hi Trap Heparin HP column (5 mL) equilibrated with distilled water (50 mL) at a flow rate of 2 mL/min. Subsequently, HG-5epi was eluted through passage of 20 mM Tris-HCl (pH: 7.4)/0.1% CHAPS (22 mL) at a flow rate of 1 mL/min. The eluted fractions containing HG-5epi were combined, and the entirety of the combined eluate was applied to ANTI-FLAG (registered trademark) M2 Affinity Gel column (product of Sigma Aldrich) (1 mL) equilibrated with 20 mM Tris-HCl (pH: 7.4)/0.1% CHAPS (10 mL) at a flow rate of 0.2 mL/min. Next, the column was washed with 20 mM Tris-HCl (pH: 7.4)/0.1% CHAPS/0.5M NaCl (10 mL) at a flow rate of 0.2 mL/min, and then 0.4 mg/mL FLAG peptide-containing 20 mM Tris-HCl (pH: 7.4)/0.1% CHAPS/150 mM NaCl (6 mL) was passed through the column at a flow rate of 0.2 mL/min, to thereby elute HG-5epi. The thus-recovered HG-5epi-containing fractions were combined, and the entirety thereof was transferred to Slide-A-Lyzer 7.0K MWCO Dialysis Cassette (product of Thermo Scientific), where the combined eluate was dialyzed against 20 mM Tris-HCl (pH: 7.4)/0.1% CHAPS/150 mM NaCl.

In each purification step, an HG-5epi-eluted fraction was confirmed through western blotting employing M2 monoclonal antibody serving as an anti-FLAG antibody. Specifically, the elution fraction obtained in the above column purification was subjected to SDS-polyacrylamide gel electrophoresis (SDS-PAGE) under reducing conditions. The proteins separated in the gel were transferred to a PVDF membrane through a semi-dry method. After transferring the proteins, the PVDF membrane was immersed in a 5% skimmed milk-containing TBS-T (20 mM Tris-HCl (pH: 7.4), 500 mM NaCl, 0.2% TritonX-100, 0.05% Tween 20), with shaking at room temperature for 1 hour, to thereby block the membrane. Subsequently, a peroxidase-labeled anti-FLAG antibody was 2,000-fold diluted with 5% skimmed milk-containing TBS-T, to thereby provide a solution. The PVDF membrane was immersed in the solution, with shaking at room temperature for 1 hour, to thereby perform antibody staining. The PVDF membrane was washed with TBS-T and immersed in SuperSignal West Dura for 1 minute. Thereafter, a luminescent signal was detected by means of Image Quant LAS4000. The luminescent signal intensity (luminance) of Amino-terminal FLAG-BAP Fusion Protein (concentration-known standard sample), which was also subjected to electrophoresis, was also determined. Through comparison of the luminescent signal intensities, the HG-5epi (protein) concentration was calculated as 0.5 μg/μL.

As shown in FIG. 1, the HG-5epi-eluted fraction obtained through purification the above column purification exhibited only a single band corresponding to about 75 kDa, as compared to a molecular weight standard (Precision plus protein unstained standards; product of Bio-Rad), when it was subjected to SDS-PAGE under reducing conditions and to CBB staining.

The thus-obtained HG-5epi-eluted fraction was employed as "recombinant HG-5epi" in the subsequent experiments.

Referential Example 3

Determination of IdoA Content Through HPLC Post Column Labeling Method

The IdoA content was determined through a HPLC post column labeling method, according to the flow diagram shown in FIG. 2. For facilitating detection by means of a fluorometer, 2-cyanoacetamide was used as a sugar labeling agent (i.e., labeling agent). The columns employed in the analysis included CarboPac PA1 (inner diameter: 4 mm×length: 50 mm) (product of Nippon Dionex K.K.) as a guard column, and CarboPac PA1 (inner diameter: 4 mm×length: 250 mm) (product of Nippon Dionex K.K.) as a separation column, wherein both columns are connected in a linear fashion. The column temperature was maintained at room temperature.

Alliance 2695 (product of Waters) was employed as a HPLC system to feed eluents. Solvent A (distilled water) and solvent B (0.1M sodium acetate) were employed as mobile phases. Elution was performed in a linear gradient manner. Specifically, the solvent B ratio was adjusted to 0% (start to 2 minutes) and increased from 0% to 5% (2 to 5 minutes) and from 5% to 10% (5 to 65 minutes). The flow rate was adjusted to 0.8 mL/min.

600E (product of Waters) was employed as a HPLC pump to feed labeling agents. Solvent C (0.5% 2-cyanoacetamide) and solvent D (0.25M NaOH) were employed as mobile phases. Liquid feeding was performed in an isocratic manner, where a solution formed of solvent C and solvent D mixed online at a ratio of 1:1 was fed at a flow rate of 0.6 mL/min.

The eluent passed through the columns under the aforementioned conditions and the labeling agent were intermingled through a three-way joint and fed to a reaction coil (inner diameter: 0.5 mm×length: 10 m), a cooling coil (inner diameter: 0.25 mm×length: 3 m), and a fluorescence detector, in this order. For labeling the sugars eluted through the columns with 2-cyanoacetamide, the reaction coil was heated at 125° C. by means of Dry Reaction Bath DB-5 (product of Shimamura Tech). For cooling the solution heated by the reaction coil, the cooling coil was employed in a state of being immersed in distilled water at room temperature. 2475 (product of Waters) was employed as a fluorescence detector, with the excitation wavelength and fluorescence wavelength being adjusted to 346 nm and 410 nm.

FIG. 3 shows a chromatogram of NAH or CDSNAc-HEP subjected to N-deacetylation and nitrous acid degradation, followed by the HPLC post column labeling method. N-deacetylation and nitrous acid degradation were performed through methods as described in the below-mentioned <Example 14>, <Example 16>, or <Example 17>. In the case of NAH, the disaccharide obtained through N-deacetylation and nitrous acid degradation is only a disaccharide (GlcA-aMan) formed of GlcA and aMan, whereas in the case of CDSNAc-HEP, two disaccharides; a disaccharide (IdoA-aMan) formed of IdoA and aMan and a disaccharide (GlcA-aMan), are obtained. Thus, through comparison of the two chromatograms, it was found that GlcA-aMan and IdoA-aMan were successfully detected separately.

Also, a standard product of GlcA-aMan and that of IdoA-aMan were analyzed through the HPLC post column labeling method, and the peak area of each disaccharide was determined. Through comparison, the amount of IdoA-aMan by mole per peak area was found to be 1.3-fold that of GlcA-aMan. Thus, the IdoA content can be calculated through the following equation by inputting the peak area of GlcA-aMan and that of IdoA-aMan.

$IdoA$ content (%)=[(peak area of $IdoA$-$aMan$)×1.3/{(peak area of $GlcA$-$aMan$)+(peak area of $IdoA$-$aMan$)×1.3}]×100 [Equation 1]

The above-employed GlcA-aMan standard product was a product obtained in the below-mentioned <Referential Example 4>, and the above-employed IdoA-aMan standard product was a product obtained in the below-mentioned <Referential Example 5>.

Referential Example 4

Preparation of GlcA-aMan Standard Product

NAH (dry powder) (20 mg) was dissolved in a hydrazine reagent (a solution of hydrazine sulfate (40 mg) dissolved in hydrazine monohydrate (1 mL)) (4 mL), and the solution was incubated at 96° C. for 5 hours by means of a heat block. The resultant solution was diluted with distilled water (4 mL), and the entirety of the diluted product was transferred to Slide-A-Lyzer 2.0K MWCO Dialysis Cassette, where it was desalinated through dialysis overnight against distilled water. Thereafter, the solution was lyophilized to form a dry powder thereof. The dry powder was dissolved in 33% acetic acid (3 mL), and the solution was mixed with 5% aqueous sodium nitrite (3 mL), followed by allowing the product to stand for 90 minutes at room temperature. To the product solution, 12.5% aqueous ammonium sulfamate (3 mL) was added, and the product was allowed to stand at room temperature for 30 minutes. Thus, a solution containing GlcA-aMan was yielded.

The solution was concentrated by means of a centrifugal evaporator to 1 mL, and the entirety of the concentrated solution was desalinated through a gel filtration column. The gel filtration column employed was a column (inner diameter: 2 cm×length: 120 cm) filed with Bio-Gel P-4 Gel (product of Bio-Rad). The column temperature was adjusted to 4° C. The mobile phase was 0.1M ammonium acetate, and the flow rate was adjusted to 0.15 mL/min. The eluate was fractionated in 4.3 mL aliquots, and GlcA-aMan-eluted fractions were confirmed through the carbazole-sulfuric acid method (BITTER T, MUIR H. M., Anal. Biochem. 1962 October; 4: 330-4). The GlcA-aMan-eluted fractions were combined and lyophilized, to thereby provide a dry powder thereof.

The dry powder was dissolved in distilled water (0.2 mL). The entirety thereof was divided into two portions, and each portion was purified through CarboPac PA1 (inner diameter: 9 mm×length: 250 mm) (product of Nippon Dionex K.K.). Solvent A (distilled water) and solvent B (0.1M sodium acetate) were employed as mobile phases. Elution was performed in a linear gradient manner. Specifically, the solvent B ratio was adjusted to 0% (start to 5 minutes) and increased from 0% to 5% (5 to 12 minutes) and from 5% to 10% (12 to 162 minutes). The flow rate was adjusted to 1.6 mL/min. The eluate was fractionated in 0.8 mL aliquots, and each fraction was analyzed through the HPLC post column labeling method, to thereby confirm a GlcA-aMan-eluted fraction. The GlcA-aMan-eluted fractions were combined, and the GlcA-aMan concentration by mole was determined through the carbazole-sulfuric acid method.

Thus, a 256 µM GlcA-aMan standard product solution (3.2 mL) was obtained.

Referential Example 5

Preparation of IdoA-aMan Standard Product

CDSNS-HEP (dry powder) (40 mg) was dissolved in distilled water (0.4 mL), and the solution was mixed with a nitrous acid-sulfuric acid solution (3.6 mL) (the solution prepared by adding 0.5M sulfuric acid (2 mL) to ice-cooled 0.5M barium nitrite (2 mL), centrifuging the mixture at 20,000×g for 1 minute, and recovering the supernatant). The resultant solution was allowed to stand at room temperature for 20 minutes, to thereby yield a solution containing IdoA-aMan.

The solution was mixed with 1M sodium carbonate (1.1 mL). The resultant solution was concentrated by means of a centrifugal evaporator to 1 mL, and the entirety of the concentrated solution was desalinated through a gel filtration column. The gel filtration column employed was a column (inner diameter: 2 cm×length: 120 cm) filed with Bio-Gel P-4 Gel. The column temperature was adjusted to 4° C. The mobile phase was 0.1M ammonium acetate, and the flow rate was adjusted to 0.24 mL/min. The eluate was fractionated in 4 mL aliquots, and IdoA-aMan-eluted fractions were confirmed through the carbazole-sulfuric acid method. The IdoA-aMan-eluted fractions were combined and lyophilized, to thereby provide a dry powder thereof.

The dry powder was dissolved in distilled water (0.2 mL). The entirety thereof was divided into three portions, and each portion was purified through CarboPac PA1 (inner diameter: 9 mm×length: 250 mm). Solvent A (distilled water) and solvent B (0.1M sodium acetate) were employed as mobile phases. Elution was performed in a linear gradient manner. Specifically, the solvent B ratio was adjusted to 0% (start to 5 minutes) and increased from 0% to 5% (5 to 12 minutes) and from 5% to 10% (12 to 162 minutes). The flow rate was adjusted to 1.6 mL/min. The eluate was fractionated in 0.8 mL aliquots, and each fraction was analyzed through the HPLC post column labeling method, to thereby confirm an IdoA-aMan-eluted fraction. The IdoA-aMan-eluted fractions were combined, and the IdoA-aMan concentration by mole was determined through the carbazole-sulfuric acid method.

Thus, a 362 µM IdoA-aMan standard product solution (8 mL) was obtained.

Example 14

Measurement of Activity of Roughly Purified HG-5Epi to NAH as a Substrate

The roughly purified recombinant HG-5epi (5 µL (2 µg)) obtained in the above <Example 9> was used. A reaction mixture (total volume: 50 µL) thereof was prepared and incubated for 17 hours in a water bath at 30° C. The reaction mixture was prepared so that the final compositional proportions (based on concentration) thereof were adjusted to 50 mM PIPES-NaOH (pH: 7.0), 0.1% CHAPS, and 10 mg/mL NAH. Thereafter, 1.3% potassium acetate-containing ethanol (117 µL) was added to the incubated reaction mixture, and the resultant mixture was centrifuged at 20,000×g for 5 minutes, to thereby precipitate the polysaccharide. The supernatant was removed, and the precipitates were dissolved in distilled water (100 µL). To the solution, 1.3% potassium acetate-containing ethanol (234 µL) was added, and the resultant mixture was centrifuged at 20,000×g for 5 minutes, to thereby precipitate the polysaccharide again. The supernatant was removed, and the precipitates were dried in air. The dried precipitates were dissolved in distilled water (60 µL), and the solution was lyophilized, to thereby provide a freeze-dry powder thereof.

The dry powder was dissolved in a hydrazine reagent (a solution of hydrazine sulfate (40 mg) dissolved in hydrazine monohydrate (1 mL)) (0.12 mL), and the solution was incubated at 96° C. for 5 hours by means of a heat block. The resultant solution was diluted with distilled water (0.2 mL), and the entirety of the diluted product was transferred to Slide-A-Lyzer 2.0K MWCO Dialysis Cassette, where it was desalinated through dialysis overnight against distilled water. Thereafter, the solution was lyophilized to form a dry powder thereof.

The dry powder was dissolved in 33% acetic acid (80 µL), and the solution was mixed with 5% aqueous sodium nitrite (80 µl), followed by allowing the product to stand for 80 minutes at room temperature. To the product solution, 12.5% aqueous ammonium sulfamate (80 µL) was added, and the product was allowed to stand at room temperature for 30 minutes. The solution was dried by means of a centrifugal evaporator, and the dry product was dissolved in distilled water (50 µL). The entirety of the solution was desalinated through a gel filtration column. The gel filtration column employed was two columns of Superdex Peptide 10/300 GL (product of GE Healthcare) connected with each other in line. The column temperature was adjusted to room temperature. The mobile phase was 0.1M ammonium acetate, and the flow rate was adjusted to 0.6 mL/min. An eluted substance was detected by means of a spectrophotometer at an ultraviolet wavelength of 200 nm. A fraction containing a disaccharide (GlcA-aMan or IdoA-aMan) was collected, and lyophilized to provide a dry powder thereof.

Subsequently, each of the fractionated samples was analyzed through a method described in the aforementioned <Referential Example 3>. Specifically, the dry powder was dissolved in distilled water (300 µL), to thereby provide an analytical sample. The sample (50 µL) was then analyzed through the HPLC post column labeling method. FIG. 4 shows the results. As shown in the chromatogram of FIG. 4, a peak attributed to IdoA-aMan was detected, indicating that HG-5epi is an enzyme which can epimerize GlcA residues of NAH to IdoA residues. The ratio in peak area of GlcA-aMan to IdoA-aMan (GlcA-aMan peak area: IdoA-aMan peak area) was 72.7:27.3. Thus, the IdoA content was calculated to 32.8%, according to the aforementioned Equation 1.

Example 15

Measurement of Activity of Roughly Purified HG-5Epi to NSH as a Substrate

The roughly purified recombinant HG-5epi (20 µL (8 µg)) obtained in the above <Example 9> was used. A reaction mixture (total volume: 50 µL) thereof was prepared and incubated for 17 hours in a water bath at 30° C. The reaction mixture was prepared so that the final compositional proportions (based on concentration) thereof were adjusted to 50 mM PIPES-NaOH (pH: 7.0), 0.1% CHAPS, and 5 mg/mL NSH. Thereafter, 1.3% potassium acetate-containing ethanol (117 µL) was added to the incubated reaction mixture, and the resultant mixture was centrifuged at 20,000×g for 5 minutes, to thereby precipitate the polysaccharide. The supernatant was removed, and the precipitates were dissolved in distilled water (100 µL). To the solution, 1.3% potassium acetate-containing ethanol (234 µL) was added, and the resultant mixture was centrifuged at 20,000×g for 5 minutes, to thereby precipitate the polysaccharide again. The supernatant was removed, and the precipitates were dried in air, followed by dissolving the dried precipitates in distilled water (10 µL).

The thus-prepared solution was mixed with a nitrous acid-sulfuric acid solution (40 µL) (the solution prepared by adding 0.5M sulfuric acid (0.5 mL) to ice-cooled 0.5M barium nitrite (0.5 mL), centrifuging the mixture at 20,000×g for 1 minute, and recovering the supernatant), and the resultant solution was allowed to stand at room temperature for 15 minutes. Then, the solution was mixed with 1M sodium carbonate (12 µL), and the entirety of the solution was desalinated through a gel filtration column. The gel filtration column employed was two columns of Superdex Peptide 10/300 GL (product of GE Healthcare) connected with each other in line. The column temperature was adjusted to room temperature. The mobile phase was 0.1M ammonium acetate, and the flow rate was adjusted to 0.6 mL/min. An eluted substance was detected by means of a spectrophotometer at an ultraviolet wavelength of 200 nm. A fraction containing a disaccharide (GlcA-aMan or IdoA-aMan) was collected, and lyophilized to provide a dry powder thereof.

Subsequently, each of the fractionated samples was analyzed through a method described in the aforementioned <Referential Example 3>. Specifically, the dry powder was dissolved in distilled water (300 µL), to thereby provide an analytical sample. The sample (50 µL) was then analyzed through the HPLC post column labeling method. FIG. 5 shows the results. As shown in the chromatogram of FIG. 5, no peak attributed to IdoA-aMan was detected, indicating that HG-5epi is an enzyme which cannot substantially epimerize GlcA residues of NSH to IdoA residues.

Example 16

Measurement of Activity of HG-5Epi to NAH as a Substrate

The recombinant HG-5epi (10 µL (5 µg)) obtained in the above <Example 13> was used. A reaction mixture (total volume: 50 µL) thereof was prepared and incubated for 12 hours in a water bath at 30° C. The reaction mixture was prepared so that the final compositional proportions (based on concentration) thereof were adjusted to 50 mM BisTris-NaOH (pH: 6.0) and 5 mg/mL NAH. Thereafter, 1.3% potassium acetate-containing ethanol (117 µL) was added to the incubated reaction mixture, and the resultant mixture was centrifuged at 20,000×g for 5 minutes, to thereby precipitate the polysaccharide. The supernatant was removed, and the precipitates were dissolved in distilled water (100 µL). To the solution, 1.3% potassium acetate-containing ethanol (234 µL) was added, and the resultant mixture was centrifuged at 20,000×g for 5 minutes, to thereby precipitate the polysaccharide again. The supernatant was removed, and the precipitates were dried in air. The dried precipitates were dissolved in distilled water (60 μL), and the solution was lyophilized, to thereby provide a freeze-dry powder thereof.

The dry powder was dissolved in a hydrazine reagent (a solution of hydrazine sulfate (40 mg) dissolved in hydrazine monohydrate (1 mL)) (0.12 mL), and the solution was incubated at 96° C. for 5 hours by means of a heat block. The resultant solution was diluted with distilled water (0.2 mL), and the entirety of the diluted product was transferred to Slide-A-Lyzer 2.0K MWCO Dialysis Cassette, where it was desalinated through dialysis overnight against distilled water. Thereafter, the solution was lyophilized to form a dry powder thereof.

The dry powder was dissolved in 33% acetic acid (100 μl), and the solution was mixed with 5% aqueous sodium nitrite (100 μL), followed by allowing the product to stand for 80 minutes at room temperature. To the product solution, 12.5% aqueous ammonium sulfamate (100 μL) was added, and the product was allowed to stand at room temperature for 30 minutes. The solution was dried by means of a centrifugal evaporator, and the dry product was dissolved in distilled water (50 μL). The entirety of the solution was desalinated through a gel filtration column. The gel filtration column employed was two columns of Superdex Peptide 10/300 GL (product of GE Healthcare) connected with each other in line. The column temperature was adjusted to room temperature. The mobile phase was 0.1M ammonium acetate, and the flow rate was adjusted to 0.6 mL/min. An eluted substance was detected by means of a spectrophotometer at an ultraviolet wavelength of 200 nm. A fraction containing a disaccharide (GlcA-aMan or IdoA-aMan) was confirmed through the carbazole-sulfuric acid method, and such fractions were collected. The combined fractions were lyophilized to provide a dry powder thereof.

Subsequently, each of the fractionated samples was analyzed through a method described in the aforementioned <Referential Example 3>. Specifically, the dry powder was dissolved in distilled water (250 μL), to thereby provide an analytical sample. The sample (50 μL) was then analyzed through the HPLC post column labeling method. FIG. 6 shows the results. As shown in the chromatogram of FIG. 6, a peak attributed to IdoA-aMan was detected, indicating that HG-5epi is an enzyme which can epimerize GlcA residues of NAH to IdoA residues. The ratio in peak area of GlcA-aMan to IdoA-aMan (GlcA-aMan peak area:IdoA-aMan peak area) was 73.1:26.9. Thus, the IdoA content was calculated to 32.4%, according to the aforementioned Equation 1.

Example 17

Measurement of Activity of HG-5Epi to CDSNAc-HEP as a Substrate

The recombinant HG-5epi (2 to 16 μL (1.0 to 8.0 μg)) obtained in the above <Example 13> was used. A reaction mixture (total volume: 100 μL) thereof was prepared and incubated for 6 hours in a water bath at 30° C. The reaction mixture was prepared so that the final compositional proportions (based on concentration) thereof were adjusted to 50 mM BisTris-NaOH (pH: 6.0), 0.1% CHAPS, and 5 mg/mL CDSNAc-HEP. Thereafter, 1.3% potassium acetate-containing ethanol (234 μL) was added to the incubated reaction mixture, and the resultant mixture was centrifuged at 20,000×g for 5 minutes, to thereby precipitate the polysaccharide. The supernatant was removed, and the precipitates were dissolved in distilled water (100 μL). To the solution, 1.3% potassium acetate-containing ethanol (234 μL) was added, and the resultant mixture was centrifuged at 20,000×g for 5 minutes, to thereby precipitate the polysaccharide again. The supernatant was removed, and the precipitates were dried in air. The dried precipitates were dissolved in distilled water (200 μL), and the solution was lyophilized, to thereby provide a freeze-dry powder thereof.

The dry powder was dissolved in a hydrazine reagent (a solution of hydrazine sulfate (40 mg) dissolved in hydrazine monohydrate (1 mL)) (0.3 mL), and the solution was incubated at 96° C. for 7 hours by means of a heat block. The resultant solution was diluted with distilled water (0.2 mL), and the entirety of the diluted product was transferred to Slide-A-Lyzer 2.0K MWCO Dialysis Cassette, where it was desalinated through dialysis overnight against distilled water. Thereafter, the solution was lyophilized to form a dry powder thereof.

The dry powder was dissolved in 33% acetic acid (200 μl), and the solution was mixed with 5% aqueous sodium nitrite (200 μL), followed by allowing the product to stand for 90 minutes at room temperature. To the product solution, 12.5% aqueous ammonium sulfamate (200 μL) was added, and the product was allowed to stand at room temperature for 30 minutes. The solution was concentrated by means of a centrifugal evaporator to 100 μL, and the entirety of the concentrated solution was desalinated through a gel filtration column. The gel filtration column employed was two columns of Superdex Peptide 10/300 GL (product of GE Healthcare) connected with each other in line. The column temperature was adjusted to room temperature. The mobile phase was 0.1M ammonium acetate, and the flow rate was adjusted to 0.6 mL/min. An eluted substance was detected by means of a spectrophotometer at an ultraviolet wavelength of 200 nm. A fraction containing a disaccharide (GlcA-aMan or IdoA-aMan) was collected, and lyophilized to provide a dry powder thereof.

Subsequently, each of the fractionated samples was analyzed through a method described in the aforementioned <Referential Example 3>. Specifically, the dry powder was dissolved in distilled water (300 μL), to thereby provide an analytical sample. The sample (50 μL) was then analyzed through the HPLC post column labeling method. Table 1 shows the results.

TABLE 1

| HG-5epi | IdoA content |
| --- | --- |
| 0 μL | 77.4% |
| 2 μL | 59.5% |
| 4 μL | 53.0% |
| 8 μL | 48.3% |
| 16 μL | 46.3% |

As shown in Table 1, the IdoA content was decreased in response to the amount of HG-5epi added, indicating that HG-5epi is an enzyme which can epimerize IdoA residues of CDSNAc-HEP to GlcA residues.

Example 18

Measurement of Activity of HG-5Epi to CDSNS-HEP as a Substrate

The recombinant HG-5epi (5 μL (2.5 μg)) obtained in the above <Example 13> was used. A reaction mixture (total volume: 50 μL) thereof was prepared and incubated for 17 hours in a water bath at 30° C. The reaction mixture was prepared so that the final compositional proportions (based on concentration) thereof were adjusted to 50 mM PIPES-NaOH (pH: 7.0), 0.1% CHAPS, and 5 mg/mL CDSNS-HEP. Thereafter, 1.3% potassium acetate-containing ethanol (117 μL) was added to the incubated reaction mixture, and the resultant mixture was centrifuged at 20,000×g for 5 minutes, to thereby precipitate the polysaccharide. The supernatant was removed, and the precipitates were dissolved in distilled water (100 μL). To the solution, 1.3% potassium acetate-containing ethanol (234 μL) was added, and the resultant mixture was centrifuged at 20,000×g for 5 minutes, to thereby precipitate the polysaccharide again. The supernatant was removed, and the precipitates were dried in air. The dried precipitates were dissolved in distilled water (10 μL).

The thus-prepared solution was mixed with a nitrous acid-sulfuric acid solution (40 μL) (the solution prepared by adding 0.5M sulfuric acid (0.5 mL) to ice-cooled 0.5M barium nitrite (0.5 mL), centrifuging the mixture at 20,000×g for 1 minute, and recovering the supernatant), and the resultant solution was allowed to stand at room temperature for 15 minutes. Then, the solution was mixed with 1M sodium carbonate (12 μL), and the entirety of the solution was desalinated through a gel filtration column. The gel filtration column employed was two columns of Superdex Peptide 10/300 GL (product of GE Healthcare) connected with each other in line. The column temperature was adjusted to room temperature. The mobile phase was 0.1M ammonium acetate, and the flow rate was adjusted to 0.6 mL/min. An eluted substance was detected by means of a spectrophotometer at an ultraviolet wavelength of 200 nm. Disaccharide (GlcA-aMan or IdoA-aMan)-eluted fractions were confirmed through the carbazole-sulfuric acid method. The disaccharide-eluted fractions were combined and lyophilized, to thereby provide a dry powder thereof.

Subsequently, each of the fractionated samples was analyzed through a method described in the aforementioned <Referential Example 3>. Specifically, the dry powder was dissolved in distilled water (300 μL), to thereby provide an analytical sample. The sample (50 μL) was then analyzed through the HPLC post column labeling method. Table 2 shows the results.

TABLE 2

| Reaction time | IdoA content |
|---|---|
| 0 hr | 83.6% |
| 17 hrs | 83.6% |

As shown in Table 2, no substantial change was observed in IdoA content before and after the reaction, indicating that HG-5epi is an enzyme which cannot substantially epimerize IdoA residues of CDSNS-HEP to GlcA residues and which cannot substantially epimerize GlcA residues of CDSNS-HEP to IdoA residues.

Example 19

Preparation of [5-$^3$H]NAH

HG-5epi activity was determined also with respect to a radioisotope-including substrate. Thus, NAH in which the hydrogen atom of the 5 position of HexA residues is substituted by $^3$H (tritium) (hereinafter referred to as "[5-$^3$H]NAH") was prepared through the following procedure.

The roughly purified recombinant HG-5epi (0.2 mL (0.08 mg)) obtained in the above <Example 9> was used. A reaction mixture (total volume: 2.7 mL) thereof was prepared and incubated for 24 hours at 30° C. by means of a heat block. The reaction mixture was prepared by lyophilizing a mixture of 0.5M PIPES-NaOH (pH: 7.0) (0.25 mL), 10% CHAPS (0.025 mL), and 50 mg/mL NAH (1 mL), re-dissolving the lyophilized product in $^3$H$_2$O (tritium water) (2.5 mL), and mixing the solution with recombinant HG-5epi (0.2 mL). Subsequently, the reaction mixture was incubated at 95° C. for 5 minutes by means of a heat block, to thereby deactivate the enzyme.

Q Sepharose HP column (product of GE Healthcare) was equilibrated with 20 mM PIPES-NaOH (pH: 7.0)/0.1% CHAPS (100 mL). Then, the entirety of the thus-prepared solution was applied to the column (20 mL) at a flow rate of 2 mL/min. Subsequently, the column was washed through passage of 20 mM PIPES-NaOH (pH: 7.0)/0.1% CHAPS/0.1M NaCl (66 mL), and then 20 mM PIPES-NaOH (pH: 7.0)/0.1% CHAPS/0.5M NaCl (34 mL) was caused to pass through the column, to thereby elute [5-$^3$H]NAH. The corresponding fractions were collected.

A [5-$^3$H]NAH-eluded fraction was confirmed by means of a liquid scintillation counter (Tri-Carb 3110TR; product of Perkin-Elmer). The [5-$^3$H]NAH-containing fractions were combined, and the entirety thereof was transferred to Slide-A-Lyzer 2.0K MWCO Dialysis Cassette, where the combined eluate was desalinated through dialysis against distilled water. The thus-obtained solution was lyophilized, and the obtained dry powder was re-dissolved in distilled water (1.6 mL).

The procedure from the above enzymatic reaction to the recovery of [5-$^3$H]NAH was performed twice, and the obtained fractions were combined. Thus, 3.0 mL of a solution of [5-$^3$H]NAH having a radioactivity of 6.3 KBq/mL was obtained.

Example 20

HG-5Epi Activity Measurement Employing Radioisotope (1)

In HG-5epi activity measurement employing a radioisotope, [5-$^3$H]NAH was used as a substrate. Radioactivity of $^3$H$_2$O generated by epimerization of HexA residues of [5-$^3$H]NAH by HG-5epi activity was measured, to thereby determine HG-5epi activity. The specific procedure is as follows.

Specifically, the recombinant HG-5epi (0.3 to 10 μL (0.15 to 5 μg)) obtained in the above <Example 13> was used. A reaction mixture (total volume: 50 μL) thereof was prepared and incubated in a water bath at 30° C. for 4 hours. The reaction mixture was prepared so that the final compositional proportions (based on concentration) thereof were adjusted to 50 mM PIPES-NaOH (pH: 7.0), 0.1% CHAPS, and 100-kdpm/mL [5-$^3$H]NAH. After completion of reaction, [5-$^3$H]NAH was removed from the solution. In a specific procedure, the entirety of the solution was applied to a spin column filled with Q Sepharose HP (0.16 mL) equilibrated with distilled water in advance, and the contents were centrifuged at 2,000×g for 20 seconds. Subsequently, the following procedure was repeated twice: distilled water (0.1 mL) was applied to the spin column, and the contents were centrifuged at 2,000×g for 20 seconds. The whole volume of the solution eluted from the spin column was recovered, and the $^3$H concentration (dpm) of the solution was measured by means of a liquid scintillation counter. Table 3 shows the results.

TABLE 3

| HG-5epi | $^3$H (dpm) |
|---|---|
| 0 μL | 45 |
| 0.3 μL | 88 |
| 1 μL | 222 |
| 3 μL | 624 |
| 10 μL | 1,715 |

As shown in Table 3, the amount of recombinant HG-5epi added (i.e., HG-5epi activity level) was found to positively correlate to the measurements (dpm), indicating that HG-5epi activity can be determined through this method. In addition, a polysaccharide having an IdoA content of interest was found to be obtained through appropriately tuning the amount of recombinant HG-5epi added to the reaction.

Example 21

HG-5Epi Activity Measurement Employing Radioisotope (2)

The recombinant HG-5epi (0.21 to 5 μL (0.110 to 2.630 μg)) obtained in the above <Example 13> was used. A reaction mixture (total volume: 50 μL) thereof was prepared and incubated in a water bath at 30° C. for 2 to 48 hours. The reaction mixture was prepared so that the final compositional proportions (based on concentration) thereof were adjusted to 50 mM Bis-Tris-HCl (pH: 6.0), and 180-kdpm/mL [5-$^3$H]NAH. Thereafter, 0.1M Tris (0.1 mL) was added to the reaction mixture, to thereby terminate the enzymatic reaction. After completion of reaction, [5-$^3$H]NAH was removed from the solution. In a specific procedure, the entirety of the solution was applied to a spin column filled with Q Sepharose HP (0.16 mL) equilibrated with distilled water in advance, and the contents were centrifuged at 2,000×g for 20 seconds. Subsequently, the following procedure was repeated twice: 0.1M Tris (0.1 mL) was applied to the spin column, and the contents were centrifuged at 2,000×g for 20 seconds. The whole volume of the solution eluted from the spin column was recovered, and the $^3$H concentration (dpm) of the solution was measured by means of a liquid scintillation counter. Table 4 shows the results.

TABLE 4

| Reaction time | HG-5epi | $^3$H (dpm) | (dpm/μg) |
|---|---|---|---|
| 0 hr | | 15 | |
| 2 hrs | 2.630 μL | 1,630 | 614 |
| 5 hrs | 1.052 μL | 1,652 | 1,556 |
| 12 hrs | 0.438 μL | 1,498 | 3,386 |
| 26 hrs | 0.202 μL | 1,409 | 6,901 |
| 48 hrs | 0.110 μL | 1,287 | 11,564 |

Each of the values (dpm/μg) shown in Table 4 was the value calculated by subtracting a blank value from a $^3$H concentration measurement (dpm) and dividing the obtained value by the amount of HG-5epi added (μg). As shown in Table 4, reaction time was found to positively correlate to the measurement per unit enzyme amount (dpm/μg), indicating that the measurement (dpm) positively correlates to the product of the amount of HG-5epi added (i.e., HG-5epi activity level) and reaction time, in the HG-5epi activity measurement employing [5-$^3$H]NAH. Therefore, reaction time positively correlates to the measurement, whereby HG-5epi activity can be determined by measuring change-over-time in $^3$H concentration (dpm). In addition, a polysaccharide having an IdoA content of interest was found to be obtained through appropriately tuning the reaction time.

Example 22

Optimum pH of HG-5Epi Activity

In order to investigate the optimum pH of HG-5epi activity, relevant enzymatic reaction was performed in an aqueous solution having a pH of 4.5 to 7.5, to thereby measure HG-5epi activity.

Specifically, the recombinant HG-5epi (5 μL (2.5 μg)) obtained in the above <Example 13> was used. A reaction mixture (total volume: 50 μL) thereof was prepared and incubated in a water bath at 30° C. for 2 hours. The reaction mixture was prepared so that the final compositional proportions (based on concentration) thereof were adjusted to 50 mM McIlvaine Buffer (pH: 4.5 to 7.5), 0.1% CHAPS, and 180-kdpm/mL [5-$^3$H]NAH. Thereafter, 0.1M Tris (0.1 mL) was added to the reaction mixture, to thereby terminate the enzymatic reaction. After completion of reaction, [5-$^3$H]NAH was removed from the solution. In a specific procedure, the entirety of the solution was applied to a spin column filled with Q Sepharose HP (0.16 mL) equilibrated with distilled water in advance, and the contents were centrifuged at 2,000×g for 20 seconds. Subsequently, the following procedure was repeated twice: 0.1M Tris (0.1 mL) was applied to the spin column, and the contents were centrifuged at 2,000×g for 20 seconds. The whole volume of the solution eluted from the spin column was recovered, and the $^3$H concentration (dpm) of the solution was measured by means of a liquid scintillation counter. Table 5 shows the results. Notably, each of the measurements (dpm) shown in Table 5 was the value calculated by subtracting a blank value at a pH of 7.0 (i.e., the measurement of a sample employing an equiamount of water instead of recombinant HG-5epi) from the actual measurement.

TABLE 5

| pH | $^3$H (dpm) |
|---|---|
| 4.5 | 2 |
| 5.0 | 215 |
| 5.5 | 860 |
| 6.0 | 800 |
| 6.5 | 444 |
| 7.0 | 197 |
| 7.5 | 57 |

As shown in Table 5, HG-5epi activity reached the highest at a pH of 5.5. Also, HG-5epi showed an almost equivalent activity at a pH of 6.0. Therefore, HG-5epi was found to be an enzyme having an optimum pH of 5.5 to 6.0.

Example 23

Effect of Salt on HG-5Epi Activity

In order to assess the effect of a salt on HG-5epi activity, HG-5epi activity was measured in the presence of sodium chloride (NaCl), magnesium chloride (MgCl$_2$), calcium chloride (CaCl$_2$), or manganese chloride (MnCl$_2$), added to adjust the final concentration to be 1 to 64 mM.

Specifically, the recombinant HG-5epi (2 µL, (1 µg)) obtained in the above <Example 13> was used. A reaction mixture (total volume: 50 µL) thereof was prepared and incubated in a water bath at 30° C. for 5 hours. The reaction mixture was prepared so that the final compositional proportions (based on concentration) thereof were adjusted to 50 mM Bis-Tris-HCl Buffer (pH: 6.0) and 180-kdpm/mL [5-$^3$H]NAH, in addition to adding a salt to be final concentration of interest. Thereafter, 0.1M Tris (0.1 mL) was added to the reaction mixture, to thereby terminate the enzymatic reaction. After completion of reaction, [5-$^3$H]NAH was removed from the solution. In a specific procedure, the entirety of the solution was applied to a spin column filled with Q Sepharose HP (0.16 mL) equilibrated with distilled water in advance, and the contents were centrifuged at 2,000×g for 20 seconds. Subsequently, the following procedure was repeated twice: 0.1M Tris (0.1 mL) was applied to the spin column, and the contents were centrifuged at 2,000×g for 20 seconds. The whole volume of the solution eluted from the spin column was recovered, and the $^3$H concentration (dpm) of the solution was measured by means of a liquid scintillation counter. Table 6 shows the results.

TABLE 6

| Concn. | $^3$H (dpm) | | | |
|---|---|---|---|---|
| | NaCl | MgCl$_2$ | CaCl$_2$ | MnCl$_2$ |
| 0 mM | 1,932 | 1,932 | 1,932 | 1,932 |
| 1 mM | 1,927 | 1,907 | 1,932 | 1,921 |
| 4 mM | 1,901 | 1,876 | 1,936 | 1,937 |
| 16 mM | 1,809 | 1,715 | 1,597 | 1,584 |
| 64 mM | 1,337 | 800 | 73 | 364 |

As shown in Table 6, HG-5epi activity was found to be inhibited in response to NaCl concentration, MgCl$_2$ concentration, CaCl$_2$ concentration, or MnCl$_2$ concentration. Particularly when 64 mM CaCl$_2$ was present, the measurement was 3×(blank value (30 dpm)) or lower, indicating that HG-5epi activity is substantially lost in the presence of 64 mM CaCl$_2$.

Example 24

Effect of Surfactant on HG-5Epi Activity

For assessing the effect of a surfactant on HG-5epi activity, HG-5epi activity was measured in the presence of 3-[(3-cholamidopropyl)dimetylammonio]-1-propanesulfonic acid (CHAPS), sodium deoxycholate, n-octyl-β-D-glucoside, or Triton X-100, added to adjust the final concentration to be 0.01 to 0.3% (w/v).

Specifically, the recombinant HG-5epi (2 µL, (1 µg)) obtained in the above <Example 13> was used. A reaction mixture (total volume: 50 µL) thereof was prepared and incubated in a water bath at 30° C. for 5 hours. The reaction mixture was prepared so that the final compositional proportions (based on concentration) thereof were adjusted to 50 mM Bis-Tris-HCl Buffer (pH: 6.0), and 180-kdpm/mL [5-$^3$H]NAH, in addition to adding a surfactant to be final concentration of interest. Thereafter, 0.1M Tris (0.1 mL) was added to the reaction mixture, to thereby terminate the enzymatic reaction. After completion of reaction, [5-$^3$H] NAH was removed from the solution. In a specific procedure, the entirety of the solution was applied to a spin column filled with Q Sepharose HP (0.16 mL) equilibrated with distilled water in advance, and the contents were centrifuged at 2,000×g for 20 seconds. Subsequently, the following procedure was repeated twice: 0.1M Tris (0.1 mL) was applied to the spin column, and the contents were centrifuged at 2,000×g for 20 seconds. The whole volume of the solution eluted from the spin column was recovered, and the $^3$H concentration (dpm) of the solution was measured by means of a liquid scintillation counter. Table 7 shows the results.

TABLE 7

| | $^3$H (dpm) | | | |
|---|---|---|---|---|
| Concn. | CHAPS | Na deoxycholate | Octylglucoside | Triton X-100 |
| 0.00% | 1,774 | 1,774 | 1,774 | 1,774 |
| 0.01% | 1,771 | 1,477 | 1,807 | 1,795 |
| 0.03% | 1,784 | 593 | 1,815 | 1,809 |
| 0.1% | 1,722 | 4 | 1,682 | 1,847 |
| 0.3% | 1,490 | 3 | 1,408 | 1,891 |

As shown in Table 7, HG-5epi activity was found to be inhibited in response to CHAPS concentration, sodium deoxycholate concentration, or n-octyl-β-D-glucoside concentration. Particularly, HG-5epi activity was significantly inhibited by sodium deoxycholate. In the presence of sodium deoxycholate at a final concentration of 0.1% or higher, HG-5epi activity was absolutely inhibited.

INDUSTRIAL APPLICABILITY

According to the present invention, an enzyme or a polypeptide which has HG-5epi activity can be provided, and thereby a polysaccharide in which HexA residues has been epimerized can be produced. Such a HexA residues-epimerized polysaccharide is expected to be useful as a new material.

DESCRIPTION OF SEQUENCE LIST

SEQ ID NO: 1: nucleotide sequence of cDNA of *Achatina fulica* HG-5epi

SEQ ID NO: 2: amino acid sequence of *Achatina fulica* HG-5epi

SEQ ID NO: 3: amino acid sequence of human C5-epi

SEQ ID NO: 4: amino acid sequence of zebrafish C5-epi

SEQ ID NO: 5: amino acid sequence of nematode C5-epi

SEQ ID NO: 6: primer

SEQ ID NOs: 7, 8: EcoRI adaptor

SEQ ID NOs: 9 to 15: primer

SEQ ID NO: 16: partial sequence of cDNA of *Achatina fulica* HG-5epi

SEQ ID NOs: 17 to 22: primer

SEQ ID NO: 23: partial sequence of cDNA of *Achatina fulica* HG-5epi

SEQ ID NOs: 24 to 27: primer

SEQ ID NO: 28: partial sequence of cDNA of *Achatina fulica* HG-5epi

SEQ ID NOs: 29, 30: primer

SEQ ID NO: 31: amino acid sequence of mouse Igκ chain secretion signal peptide

SEQ ID NO: 32: amino acid sequence of FLAG tag
SEQ ID NO: 33: nucleotide sequence of recombinant DNA encoding mouse Igκ chain secretion signal peptide and FLAG tag
SEQ ID NO: 34: amino acid sequence of polypeptide consisting of mouse Igκ chain secretion signal peptide and FLAG tag
SEQ ID NOs: 35 to 42: primer

The invention claimed is:

1. A polypeptide selected from the group consisting of the following (A) to (D), provided that said polypeptide is not a polypeptide consisting of the amino acid sequence of residues 1 to 601 of SEQ ID NO: 2 and does not contain the amino acid sequence of residues 1 to 33 of SEQ ID NO: 2, wherein said polypeptide has an activity of epimerizing glucuronic acid residues of N-acetyl heparosan to iduronic acid residues:
(A) a polypeptide comprising the amino acid sequence of residues 34 to 601 of SEQ ID NO: 2;
(B) a polypeptide comprising the amino acid sequence of residues 1 to 601 of SEQ ID NO: 2 but in which 1 to 60 amino acid residues are substituted, deleted, inserted, and/or added;
(C) a polypeptide comprising the amino acid sequence of residues 34 to 601 of SEQ ID NO: 2 but in which 1 to 56 amino acid residues are substituted, deleted, inserted, and/or added; and
(D) a fusion polypeptide, wherein said fusion polypeptide comprises the polypeptide of (A), (B) or (C) fused to a peptide tag.

2. The polypeptide according to claim 1, wherein said polypeptide contains at least one amino acid substitution or insertion with respect to the amino acid sequence of residues 1 to 601 of SEQ ID NO: 2.

3. A polynucleotide molecule encoding a polypeptide according to claim 1.

4. A vector comprising the nucleic acid according to claim 3.

5. A host cell harboring a nucleic acid and/or a vector comprising the nucleic acid, wherein the nucleic acid is the nucleic acid according to claim 3.

6. A method for producing a polypeptide, the method comprising the following steps (A) and (B):
(A) a step of expressing a polypeptide having an activity of epimerizing glucuronic acid residues of N-acetyl heparosan to iduronic acid residues by culturing the host cell according to claim 5; and
(B) a step of recovering the polypeptide expressed in step (A).

7. A method for producing a polysaccharide in which hexuronic acid residues have been epimerized, said method comprising a step of bringing into contact a polypeptide according to claim 1 with a polysaccharide including a disaccharide formed of an N-acetyl glucosamine residue and a hexuronic acid residue.

8. The method according to claim 7, wherein said polysaccharide is N-acetyl heparosan.

* * * * *